US007858613B2

(12) United States Patent
Hinze et al.

(10) Patent No.: US 7,858,613 B2
(45) Date of Patent: Dec. 28, 2010

(54) SUBSTITUTED BENZO-CONDENSED CYCLOHEPTANONE DERIVATIVES AND THEIR USE FOR PRODUCING DRUGS

(75) Inventors: Claudia Hinze, Aachen (DE); Robert Frank, Aachen (DE); Ruth Jostock, Stolberg (DE); Klaus Schiene, Duesseldorf (DE); Michael Haurand, Aachen (DE); Hagen-Heinrich Hennies, Simmerath (DE)

(73) Assignee: Gruenenthal GmbH, Aachen (DE)

( * ) Notice: Subject to any disclaimer, the term of this patent is extended or adjusted under 35 U.S.C. 154(b) by 35 days.

(21) Appl. No.: 11/915,116

(22) PCT Filed: May 17, 2006

(86) PCT No.: PCT/EP2006/004665

§ 371 (c)(1),
(2), (4) Date: Aug. 8, 2008

(87) PCT Pub. No.: WO2006/122776

PCT Pub. Date: Nov. 23, 2006

(65) Prior Publication Data

US 2009/0215858 A1 Aug. 27, 2009

(30) Foreign Application Priority Data

May 20, 2005 (DE) .................... 10 2005 023 944

(51) Int. Cl.
| | | |
|---|---|---|
| C07D 223/16 | (2006.01) | |
| C07D 223/08 | (2006.01) | |
| C07D 223/04 | (2006.01) | |
| C07D 337/00 | (2006.01) | |
| C07D 313/00 | (2006.01) | |
| A01N 43/00 | (2006.01) | |
| A01N 43/22 | (2006.01) | |
| A01N 43/02 | (2006.01) | |
| A61K 31/55 | (2006.01) | |
| A61K 31/335 | (2006.01) | |

(52) U.S. Cl. ................ 514/213.01; 514/431; 514/450; 540/593; 540/604; 540/611; 549/9; 549/355

(58) Field of Classification Search ............ 514/213.01, 514/217.11, 431, 437, 460, 450; 549/9, 354, 549/355; 540/593, 604, 611
See application file for complete search history.

(56) References Cited

U.S. PATENT DOCUMENTS 6,384,072 B1  5/2002  Hattori et al.

FOREIGN PATENT DOCUMENTS

| DE | 1 913 199 | 9/1970 |
| EP | 0 383 318 A2 | 8/1990 |
| EP | 0 567 138 A2 | 10/1993 |
| GB | 1 218 778 | 1/1971 |
| GB | 1 249 261 | 10/1971 |
| JP | 61-129179 A | 6/1986 |
| WO | WO 98/36749 A1 | 8/1998 |
| WO | WO99/24397 | * 5/1999 |
| WO | WO 2004/052845 A1 | 6/2004 |
| WO | WO 2005/044802 A2 | 5/2005 |

OTHER PUBLICATIONS

Vippagunta et. al., Advanced Drug Delivery Reviews, 2001, Elsevier Science, 48, pp. 3-26.*
Corresponding German Search Report dated Jan. 17, 2006 with English translation of relevant portion (Nine (9) pages).
Written Opinion of the International Searching Authority (Form PCT/ISA/237) along with Form PCT/IB/338 and Form PCT/IB/373 with English translation of relevant portion (Fourteen (14) pages).
Corresponding International Search Report dated Oct. 6, 2006 (Form PCT/ISA/210) with English translation of relevant portion (Seven (7) pages).
John J. Sciarra, PhD et al., "Aerosols", Remington's Pharmaceutical Sciences, 1985, pp. 1662-1677, Chapter 93, 17th Edition, Mack Publishing Company, Easton, Pa.
Mark A. Longer et al., "Sustained-Release Drug Delivery Systems", Remington's Pharmaceutical Sciences, 1985, pp. 1644-1661, Chapter 92, 17th Edition, Mack Publishing Company, Easton, Pa.
Stuart C. Porter, Ph.D., "Coating of Pharmaceutical Dosage Forms", Remington's Pharmaceutical Sciences, 1985, pp. 1633-1643, Chapter 91, 17th Edition, Mack Publishing Company, Easton, Pa.
Robert E. King, Ph.D. et al., "Oral Solid Dosage Forms", Remington's Pharmaceutical Sciences, 1985, pp. 1603-1632, Chapter 90, 17th Edition, Mack Publishing Company, Easton, Pa.
Edward G. Rippie, Ph.D. et al., "Powders", Remington's Pharmaceutical Sciences, 1985, pp. 1585-1602, Chapter 89, 17th Edition, Mack Publishing Company, Easton, Pa.
Lawrence H. Block, Ph.D., "Medicated Applications", Remington's Pharmaceutical Sciences, 1985, pp. 1567-1584, Chapter 88, 17th Edition, Mack Publishing Company, Easton, Pa.
John D. Mullins, Ph.D., "Ophthalmic Preparations", Remington's Pharmaceutical Sciences, 1985, pp. 1553-1566, Chapter 87, 17th Edition, Mack Publishing Company, Easton, Pa.
Salvatore J. Turco, Pharm.D. et al., "Intravenous Admixtures", Remington's Pharmaceutical Sciences, 1985, pp. 1542-1552, Chapter 86, 17th Edition, Mack Publishing Company, Easton, Pa.
Kenneth E. Avis, DSC, "Parenteral Preparations", Remington's Pharmaceutical Sciences, 1985, pp. 1518-1541, Chapter 85, 17th Edition, Mack Publishing Company, Easton, Pa.

(Continued)

*Primary Examiner*—Sreeni Padmanabhan
*Assistant Examiner*—Sarah Pihonak
(74) *Attorney, Agent, or Firm*—Crowell & Moring LLP

(57) ABSTRACT

The invention relates to substituted benzo-condensed cycloheptanone derivatives, to methods for producing them, to drugs containing said compounds and to the use of said compounds for producing drugs.

19 Claims, No Drawings

OTHER PUBLICATIONS

J. G. Nairn, Ph.D., "Solutions, Emulsions, Suspensions and Extractives", Remington's Pharmaceutical Sciences, 1985, pp. 1492-1517, Chapter 84, 17th Edition, Mack Publishing Company, Easton, Pa.

Clyde R. Erskine, Jr, "Quality Assurance and Control", Remington's Pharmaceutical Sciences, 1985, pp. 1487-1491, Chapter 83, 17th Edition, Mack Publishing Company, Easton, Pa.

Carl J. Lintner Ph.D., "Stability of Pharmaceutical Products", Remington's Pharmaceutical Sciences, 1985, pp. 1478-1486, Chapter 82, 17th Edition, Mack Publishing Company, Easton, Pa.

Robert L. Giles, BA, et al., "Plastic Packaging Materials", Remington's Pharmaceutical Sciences, 1985, pp. 1473-1477, Chapter 81, 17th Edition, Mack Publishing Company, Easton, Pa.

Frederick P. Siegel Ph.D., "Tonicity, Osmoticity, Osmolality, and Osmolarity" Remington's Pharmaceutical Sciences, 1985, pp. 1455-1472, Chapter 80, 17th Edition, Mack Publishing Company, Easton, Pa.

G. Briggs Phillips, Ph.D. "Sterilization", Remington's Pharmaceutical Sciences, 1985, pp. 1443-1454, Chapter 79, 17th Edition, Mack Publishing Company, Easton, Pa.

Adelbert M. Knevel, Ph.D., "Separation", Remington's Pharmaceutical Sciences, 1985, pp. 1432-1442, Chapter 78, 17th Edition, Mack Publishing Company, Easton, Pa.

Anthony R. Disanto, Ph.D., "Bioavailability and Bioequivalency Testing", Remington's Pharmaceutical Sciences, 1985, pp. 1424-1431, Chapter 77, 17th Edition, Mack Publishing Company, Easton, Pa.

Louis J. Ravin, Ph.D., "Preformulation", Remington's Pharmaceutical Sciences, 1985, pp. 1409-1423, Chapter 76, 17th Edition, Mack Publishing Company, Easton, Pa.

Terence J. Coderre et al., "Contribution of Central Neuroplasticity to Pathological Pain: Review of Clinical and Experimental Evidence", Pain, 1993, pp. 259-285, vol. 52, Elsevier Science Publishers B.V.

L. C. Hendershot et al., Antagonism of the Frequency of Phenylquinone-Induced Writhing in the Mouse by Weak Analgesics and Nonanalgesics:, J. Pharmacol. Exp. Ther., Sep. 19, 1958, pp. 237-240, vol. 125.

Bernd Eistert et al., "Weitere Umsetzungen von Phenanthrenchinon mit Aliphatischen Diazoverbindungen". Chem. Ber., 1968, pp. 84-33, vol. 101.

B.D. Astill et al., "The Synthesis of 1-Benzazepine Derivatives as Model Compounds Related to Apo-β-Erythroidine[1,2]", Journal of the American Chemical Society, Aug. 5, 1955, pp. 4079-4084, vol. 77, XP-002397577.

Christopher S.J. Walpole et al., "The Discovery of Capsazepine, the First Competitive Antagonist of the Sensory Neuron Excitants Capsaicin and Resiniferatoxin", Journal of Medicinal Chemistry, 1994, pp. 1942-1954, vol. 37, American Chemical Society, XP-002397578.

* cited by examiner

SUBSTITUTED BENZO-CONDENSED CYCLOHEPTANONE DERIVATIVES AND THEIR USE FOR PRODUCING DRUGS

The present invention relates to substituted benzofused cycloheptanone derivatives, to processes for their preparation, to medicaments comprising these compounds and to the use of these compounds for producing medicaments.

The treatment of pain, especially of neuropathic pain, has great significance in medicine. There is a global demand for effective pain therapies. The urgent need for research into patient-oriented and targeted treatment of chronic and non-chronic states of pain, which is understood to mean the successful and satisfactory treatment of pain for the patient, is also documented in a large number of scientific studies which have recently appeared in the field of applied analgesics and fundamental research into nociception.

A suitable starting point for the treatment of pain, especially of neuropathic pain, is the vanilloid receptor of subtype 1 (VR1/TRPV1), which is frequently also referred to as the capsaicin receptor. This receptor is stimulated, inter alia, by vanilloids, for example capsaicin, heat and protons, and plays a central role in the development of pain. Furthermore, it is of significance for a multitude of further physiological and pathophysiological processes, for example migraines; depressions; neurodegenerative disorders; cognitive disorders; states of anxiety; epilepsy; coughing; diarrhea; pruritus; disorders of the cardiovascular system; disorders of food uptake; medicament dependence; medicament abuse and especially urine incontinence.

It was therefore an object of the present invention to provide novel compounds which are suitable especially as active pharmaceutical ingredients in medicaments, preferably in medicaments for the treatment of disorders or diseases which are mediated at least partly by vanilloid receptors 1 (VR1/TRPV1 receptors).

It has now been found that, surprisingly, substituted benzofused cycloheptanone derivatives of the general formula I specified below are suitable for treating pain and have an excellent affinity for the vanilloid receptor of subtype 1 (VR1/TRPV1 receptor). Furthermore, these inventive benzofused cycloheptanone derivatives also exhibit a high affinity for cannabinoid receptors CB1 (CB1 receptors) and/or cannabinoid receptors CB2 (CB2 receptors). The inventive benzofused cycloheptanone compounds are therefore suitable especially for prophylaxis and/or treatment of disorders or diseases which are mediated at least partly by vanilloid receptors 1 (VR1/TRPV1) and/or cannabinoid receptors CB1 (CB1 receptors) and/or cannabinoid receptors CB2 (CB2 receptors).

The present invention therefore provides substituted benzofused cycloheptanone derivatives of the general formula I

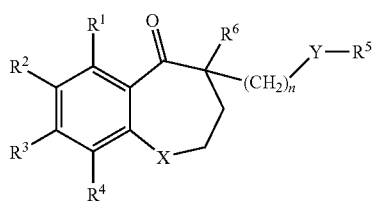

I in which
n is 1, 2 or 3;

X is $CH_2$, O, S, S(=O), $S(=O)_2$, N(H), N($R^7$), N[C(=O)—$R^8$] or N[C(=O)—O—$R^9$];

Y is O, O—C(=O), O—C(=O)—O, O—S(=O)$_2$, O—C(=O)—N(H), O—C(=S)—N(H), N(H)—C(=O)—N(H) or N(H)—C(=S)—N(H); where the atom which binds to the $R^5$ radical is always stated last;

$R^1$, $R^2$, $R^3$ and $R^4$ are each independently

H, F, Cl, Br, I, —$SF_5$, —CN, —NC, —$NO_2$, —$SO_3H$, —$NH_2$, —OH, —SH, —$OR^{10}$, —$SR^{11}$, —$NR^{12}R^{13}$, —NH—$R^{14}$, —NH—C(=O)—$R^{15}$, —$NR^{16}$—C(=O)—$R^{17}$, —C(=O)—$NH_2$, —C(=O)—NH—$R^{18}$, —C(=O)—$NR^{19}R^{20}$, —C(=O)—H, —C(=O)—$R^{21}$, —C(=O)—OH, —C(=O)—$OR^{22}$, —O—C(=O)—$R^{23}$ or a linear or branched, saturated or unsaturated, unsubstituted or at least monosubstituted aliphatic radical;

$R^5$ is a —C(=O)—$R^{24}$ group;
is a —$S(=O)_2$—$R^{25}$ group;
is a linear or branched, saturated or unsaturated, unsubstituted or at least monosubstituted aliphatic radical;
is an unsubstituted or at least monosubstituted, unsaturated or saturated cycloaliphatic radical optionally having at least one heteroatom as a ring member;
or an unsubstituted or at least monosubstituted aryl or heteroaryl radical which may be bonded via a linear or branched, unsubstituted or at least monosubstituted alkylene, alkenylene or alkynylene group, and/or fused to an unsubstituted or at least monosubstituted mono- or polycyclic ring system;

$R^6$ is a hydrogen radical;
is —$(CH_2)_p$—Z—$R^{26}$ where p=1, 2 or 3;
or is —$(CH_2)_q$—$OR^{27}$ where q=1, 2 or 3;

$R^7$, $R^8$ and $R^9$ are each independently
a linear or branched, saturated or unsaturated, unsubstituted or at least monosubstituted aliphatic radical;
or an unsubstituted or at least monosubstituted aryl or heteroaryl radical which is bonded via a linear or branched, unsubstituted or at least monosubstituted alkylene, alkenylene or alkynylene group;

$R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ are each independently
a linear or branched, saturated or unsaturated, unsubstituted or at least monosubstituted aliphatic radical;
an unsubstituted or at least monosubstituted, unsaturated or saturated cycloaliphatic radical optionally having at least one heteroatom as a ring member;
or an unsubstituted or at least monosubstituted aryl or heteroaryl radical which may be bonded via a linear or branched, unsubstituted or at least monosubstituted alkylene, alkenylene or alkynylene group and/or may be fused to an unsubstituted or at least monosubstituted mono- or polycyclic ring system;

Z is O, O—C(=O), O—C(=O)—O, O—$S(=O)_2$, O—C(=O)—N(H), O—C(=S)—N(H), N(H)—C(=O)—N(H) or N(H)—C(=S)—N(H); where the atom which binds to the $R^{26}$ radical is always stated last;

$R^{24}$, $R^{25}$, $R^{28}$ and $R^{29}$ are each independently
an unsubstituted or at least monosubstituted, unsaturated or saturated cycloaliphatic radical optionally having at least one heteroatom as a ring member;
or an unsubstituted or at least monosubstituted aryl or heteroaryl radical which may be fused to an unsubstituted or at least monosubstituted mono- or polycyclic ring system;

$R^{26}$ is a —C(=O)—$R^{28}$ group;
is a —$S(=O)_2$—$R^{29}$ group;

is an unsubstituted or at least monosubstituted, unsaturated or saturated cycloaliphatic radical optionally having at least one heteroatom as a ring member;

is a linear or branched, saturated or unsaturated, unsubstituted or at least monosubstituted aliphatic radical;

is an unsubstituted or at least monosubstituted aryl or heteroaryl radical which may be bonded via a linear or branched, unsubstituted or at least monosubstituted alkylene, alkenylene or alkynylene group and/or may be fused to an unsubstituted or at least monosubstituted mono- or polycyclic ring system;

and $R^{27}$ is a hydrogen radical;

in each case, as appropriate, in the form of one of their pure stereoisomers, especially enantiomers or diastereomers, of its racemates or in the form of a mixture of stereoisomers, especially of the enantiomers and/or diastereomers, in any mixing ratio, or in each case in the form of corresponding salts, or in each case in the form of corresponding solvates.

Preference may be given to excluding benzofused cycloheptanone derivatives of the general formula I in which X is $CH_2$; $R^6$ is a hydrogen radical or —$(CH_2)_p$—Z—$R^{26}$ where p=1, 2 or 3; Z is O or O—C(=O); $R^{26}$ is a linear or branched, saturated or unsaturated, unsubstituted or at least monosubstituted aliphatic radical; n is 1, 2 or 3; Y is O or O—C(=O); $R^5$ is a linear or branched, saturated or unsaturated, unsubstituted or at least monosubstituted aliphatic radical, and $R^1$, $R^2$, $R^3$ and $R^4$ are each any of the aforementioned substituents.

Aliphatic radicals in the context of this invention include acyclic saturated or unsaturated hydrocarbon radicals which may be branched or straight-chain and also unsubstituted or monosubstituted or polysubstituted identically or differently, having preferably from 1 to 20 (i.e. 1, 2, 3, 4, 5, 6, 7, 8, 9, 10, 11, 12, 13, 14, 15, 16, 17, 18, 19 or 20), more preferably from 1 to 12 (i.e. 1, 2, 3, 4, 5, 6, 7, 8, 9, 10, 11 or 12), most preferably from 1 to 6 (i.e. 1, 2, 3, 4, 5 or 6) carbon atoms, i.e. $C_{1-20}$-, $C_{1-12}$-, $C_{1-6}$-alkyls, $C_{2-20}$-, $C_{2-12}$-, $C_{2-6}$-alkenyls and $C_{2-20}$-, $C_{2-12}$-, $C_{2-6}$-alkynyls. Alkenyls have at least one C—C double bond and alkynyls have at least one C—C triple bond. Advantageously, aliphatic radicals may be selected from the group which comprises methyl, ethyl, n-propyl, isopropyl, n-butyl, isobutyl, sec-butyl, tert-butyl, n-pentyl, isopentyl, neo-pentyl, n-hexyl, 2-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-eicosanyl, ethenyl(vinyl), ethynyl, propenyl (—$CH_2CH=CH_2$, —$CH=CH—CH_3$, —$C(=CH_2)$—$CH_3$), 2-methylpropenyl, propynyl (—$CH_2$—C≡CH, —C≡C—$CH_3$), butenyl, butynyl, pentenyl, pentynyl, hexenyl, hexynyl, octenyl and octynyl.

In connection with aliphatic radicals, the term "substituted"—unless defined differently—in the context of this invention is understood to mean single or multiple substitution, preferably mono-, di-, tri-, tetra-, penta-, hexa-, hepta-, octa- or nonasubstitution, of one or more hydrogen atoms by, for example, F, Cl, Br, I, —CN, —$NO_2$, —OH, —SH and —$NH_2$, where the multiple substitution is multiple, for example double or triple, either on different or on the same atoms, for example triple on the same carbon atom as in the case of —$CF_3$ or —$CH_2CF_3$, or on different positions as in the case of —CH(OH)—CH=CCl—$CH_2Cl$. Multiple substitution can be effected with the same or different substituents. Preferred substituted aliphatic radicals are —$CH_2$—Cl, —$CH_2$—Br, —$CH_2$—$CH_2$—Cl, —$CH_2$—$CH_2$—Br, —$CH_2$—$CH_2$—$CH_2$—Br, —$CH_2$—$CH_2$—$CH_2$—Cl, —$CF_3$, —$CHF_2$, —$CH_2F$, —$CCl_3$, —$CBr_3$, —$CH_2$—CN, —$CH_2$—$NO_2$, —$CF_2$—$CF_3$, —$CH_2$—$CF_3$, —$CCl_2$-$CCl_3$, —$CF_2$—$CH_3$, —$CH_2$—$CH_2$—CN, —$CH_2$—$CH_2$—$NO_2$, —$CF_2$—$CF_2$—$CF_3$, —$CH_2$—$CH_2$—$CH_2$—CN and —$CH_2$—$CH_2$—$CH_2$—$NO_2$.

For the purposes of the present invention, the term "aryl radical" should preferably be understood to mean a radical which is selected from the group which comprises phenyl, naphthyl, phenanthrenyl and anthracenyl, and is unsubstituted or mono- or polysubstituted identically or differently. Aryl is preferably an unsubstituted or monosubstituted or identically or differently polysubstituted, for example bi-, tri-, tetra- or pentasubstituted, phenyl, 1-naphthyl or 2-naphthyl.

In the context of the present invention, heteroaryl radicals are those heterocycles which are heteroaromatic. Heteroaryl radicals are preferably 5- to 14-membered, i.e. 5-, 6-, 7-, 8-, 9-, 10-, 11-, 12-, 13- or 14-membered, and have preferably 1, 2, 3, 4 or heteroatoms selected independently from the group comprising oxygen, nitrogen and sulfur. Each heteroaryl radical may be present unsubstituted or monosubstituted or polysubstituted, for example bi-, tri-, tetra- or pentasubstituted, identically or differently.

Examples of heteroaryl radicals in the context of the present invention include thiophenyl, furanyl, pyrrolyl, pyrazolyl, pyranyl, pyridinyl, imidazolyl, indolyl, Isoindolyl, benzo[b]furanyl, benzo[b]thiophenyl, thiazolyl, oxazolyl, isoxazolyl, pyridazinyl, pyrazinyl, pyrimidinyl, indazolyl, quinazolinyl, quinolinyl, isoquinolinyl, benzimidazolinyl, benzoxazolyl, benzisoxazolyl, benzothiazolyl, benzo[2,1,3]thiadiazolyl, [1,2,3]-benzothiadiazolyl, [2,1,3]-benzoxadiazolyl and [1,2,3]-benzoxadiazolyl.

In relation to aryl and heteroaryl radicals, "substituted" in the context of this invention is understood to mean the single or multiple substitution, for example mono-, di-, tri-, tetra- or pentasubstitution, of one or more hydrogen atoms of the ring system by suitable substituents. When the definition of these suitable substituents in connection with aryl or heteroaryl radicals is not defined elsewhere in the description or in the claims, suitable substituents are F, Cl, Br, I, —CN, —$CF_3$, —$SF_5$, —OH, —O—$C_{1-10}$-alkyl, —$NH_2$, —$NO_2$, —O—$CF_3$, —S—$CF_3$, —SH, —S—$C_{1-5}$-alkyl, —$C_{1-5}$-alkyl, —C(=O)—OH, —C(=O)—O—$C_{1-5}$-alkyl, —O—C(=O)—$C_{1-5}$-alkyl, —NH—$C_{1-5}$-alkyl, —N($C_{1-5}$-alkyl)$_2$, —NH—C(=O)—O—$C_{1-5}$-alkyl, —C(=O)—H, —C(=O)—$C_{1-5}$-alkyl, —C(=O)—$NH_2$, —C(=O)—NH—$C_{1-5}$-alkyl, C(=O)—N—($C_{1-5}$-alkyl)$_2$, —S(=O)$_2$—$C_{1-5}$-alkyl, —S(=O)$_2$-phenyl, —NH—S(=O)$_2$—$C_{1-5}$-alkyl, —S(=O)$_2$—NH—$C_{1-5}$-alkyl, cyclohexyl, cyclopentyl, pyridinyl, pyridazinyl, —($CH_2$)-benzo[b]furanyl, —O-phenyl, —O-benzyl, phenyl and benzyl, where the cyclic moiety of the pyridinyl, cyclopentyl, cyclohexyl, pyridazinyl, —S(=O)$_2$-phenyl, —O-phenyl, —O-benzyl, phenyl, —($CH_2$)— benzo[b]furanyl and benzyl radicals may in each case be substituted by 1, 2, 3, 4 or 5 substituents selected independently from the group consisting of F, Cl, Br, —OH, —$CF_3$, —$SF_5$, —CN, —$NO_2$, —$C_{1-5}$-alkyl, —O—$C_{1-5}$-alkyl, —O—$CF_3$, —S—$CF_3$, phenyl and —O-benzyl.

The multiple substitution is effected with the same or with different substituents.

The aforementioned linear or branched alkylene, alkenylene or alkynylene groups preferably have from 1 to 5 carbon atoms, i.e. they are $C_{1-5}$-alkylene, $C_{2-5}$-alkenylene or $C_{2-5}$-alkynylene groups, each of which may be unsubstituted or substituted by 1, 2, 3, 4 or 5 substituents selected independently from the group consisting of F, Cl, Br, —OH, —SH, —$NH_2$, —CN, —$NO_2$ and phenyl, where the phenyl radical may be substituted by 1, 2, 3, 4 or 5 substituents selected independently from the group consisting of methyl, ethyl, n-propyl, isopropyl, n-butyl, isobutyl, sec-butyl, tert-butyl, n-pentyl, isopentyl and neopentyl.

Alkylene may preferably be selected from the group consisting of —(CH$_2$)—, —(CH$_2$)$_2$—, —C(H)(CH$_3$)—, —C(CH$_3$)$_2$—, —(CH$_2$)$_3$—, —(CH$_2$)$_4$—, —(CH$_2$)$_5$—, —C(H)(CH$_3$)—(CH$_2$)—, —C(H)(C$_2$H$_5$)—(CH$_2$)—, —C(phenyl)$_2$- and —C(H)(phenyl).

Alkenylene groups may preferably be selected from the group consisting of —CH=CH—, —C(CH$_3$)=CH—, —C(C$_2$H$_5$)=CH—, —CH=C(CH$_3$)—, —CH=C(C$_2$H$_5$)—, —CH=C(phenyl)-, —CH=C(p-tolyl), —C(phenyl)=CH— and —C(p-tolyl)=CH—.

An alkynylene group is preferably a —C≡C— group.

Cycloaliphatic radicals in the context of this invention are cyclic saturated or unsaturated hydrocarbon radicals having preferably 3, 4, 5, 6, 7, 8, 9, 10, 11, 12, 13, 14, 15 or 16, more preferably 3, 4, 5, 6, 7 or 8 carbon atoms, where each radical may be unsubstituted or monosubstituted or polysubstituted identically or differently. Cycloaliphatic radicals may preferably have 1, 2, 3, 4 or 5 heteroatoms selected independently from the group consisting of oxygen, nitrogen (NH) and sulfur.

Examples of cycloaliphatic radicals include cyclopropyl, cyclobutyl, cyclopentyl, cyclohexyl, cyclooctyl, cyclononyl, cyclodecyl, cycloundecyl, cyclododecyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl, thiomorpholinyl, tetrahydropyranyl, azepanyl, diazepanyl and dithiolanyl.

A mono- or polycyclic ring system is understood in the context of the present invention to mean mono- or polycyclic hydrocarbon radicals which may be saturated or unsaturated and optionally have 1, 2, 3, 4 or 5 heteroatom(s) as ring member(s), which are each independently selected from the group consisting of oxygen, nitrogen and sulfur.

Such a mono- or polycyclic ring system may, for example, be fused to an aryl radical or a heteroaryl radical.

When a polycyclic ring system, for example a bicyclic ring system, is present, the different rings may each independently have a different degree of saturation, i.e. be saturated or unsaturated. A polycyclic ring system is preferably a bicyclic ring system.

Examples of aryl radicals which are fused to a mono- or polycyclic ring system include [1,3]-benzodioxolyl, [1,4]-benzodioxanyl, [1,2,3,4]-tetrahydronaphthyl, [1,2,3,4]-tetrahydroquinolinyl, [1,2,3,4]-tetrahydroquinazolinyl and [3,4]-dihydro-2H-1,4-benzoxazinyl.

In connection with cycloaliphatic radicals and mono- or polycyclic ring systems, the term "substituted"—unless defined differently—in the context of this invention is understood to mean the single or multiple substitution, for example the mono-, di-, tri-, tetra-, penta-, hexa-, hepta-, octa- or nonasubstitution, of one or more hydrogen atoms by, for example, oxo (=O), thioxo (=S), F, Cl, Br, I, —CN, —CF$_3$, —SF$_5$, —OH, —O—C$_{1-5}$-alkyl, —NH$_2$, —NO$_2$, —O—CF$_3$, —S—CF$_3$, —SH, —S—C$_{1-5}$-alkyl, —C$_{1-5}$-alkyl, —C(=O)—OH, —C(=O)—O—C$_{1-5}$-alkyl, —O—C(=O)—C$_{1-5}$-alkyl, —NH—C$_{1-5}$-alkyl, —N(C$_{1-5}$-alkyl)$_2$, —NH—C(=O)—O—C$_{1-5}$-alkyl, —C(=O)—H, —C(=O)—C$_{1-5}$-alkyl, —C(=O)—NH$_2$, —C(=O)—NH—C$_{1-5}$-alkyl, C(=O)—N—(C$_{1-5}$-alkyl)$_2$, —S(=O)$_2$—C$_{1-5}$-alkyl, —S(=O)$_2$-phenyl, —NH—S(=O)$_2$—C$_{1-5}$-alkyl, —S(=O)$_2$—NH—C$_{1-5}$-alkyl, cyclohexyl, cyclopentyl, pyridinyl, pyridazinyl, —(CH$_2$)-benzo[b]furanyl, —O-phenyl, —O-benzyl, phenyl and benzyl, where the cyclic moiety of the pyridinyl, cyclopentyl, cyclohexyl, pyridazinyl, —S(=O)$_2$-phenyl, —O-phenyl, —O-benzyl, phenyl, —(CH$_2$)-benzo[b]furanyl and benzyl radicals may in each case be substituted by 1, 2, 3, 4 or 5 substituents selected independently from the group consisting of F, Cl, Br, —OH, —CF$_3$, —SF$_5$, —CN, —NO$_2$, —C$_{1-5}$-alkyl, —O—C$_{1-5}$-alkyl, —O—CF$_3$, —S—CF$_3$, phenyl and —O-benzyl. The polysubstitution can be effected multiply, for example doubly or triply, either on different or on the same atoms. The polysubstitution can be effected with identical or different substituents.

Particular preference is given to substituted benzofused cycloheptanone derivatives of the general formula I specified above in which n is 1;

X is CH$_2$, O, S, S(=O), S(=O)$_2$, N(H), N(R$^7$), N[C(=O)—R$^8$] or N[C(=O)—O—R$^9$];

Y is O, O—C(=O), O—C(=O)—O, O—S(=O)$_2$, O—C(=S)—N(H) or O—C(=O)—N(H);

R$^1$, R$^2$, R$^3$ and R$^4$ are each independently

H, F, Cl, Br, I, —SF$_5$, —CN, —NC, —NO$_2$, —OH, —SH, —OR$^{10}$, —SR$^{11}$, —NR$^{12}$R$^{13}$, or a radical selected from the group consisting of methyl, —CF$_3$, —CHF$_2$, —CH$_2$F, —CCl$_3$, —CBr$_3$, —CH$_2$—CN, —CH$_2$—NO$_2$, ethyl, —CF$_2$—CF$_3$, —CH$_2$—CF$_3$, —CCl$_2$-CCl$_3$, —CF$_2$—CH$_3$, —CH$_2$—CH$_2$—CN, —CH$_2$—CH$_2$—NO$_2$, n-propyl, —CF$_2$—CF$_2$—CF$_3$, —CH$_2$—CH$_2$—CH$_2$—CN, —CH$_2$—CH$_2$—CH$_2$—NO$_2$, isopropyl, n-butyl, sec-butyl, isobutyl, tert-butyl, 1,1-dimethylpropyl, n-pentyl, sec-pentyl, n-hexyl and n-heptyl;

R$^5$ is a —C(=O)—R$^{24}$ group;

is a —S(=O)$_2$—R$^{25}$ group;

is a radical selected from the group consisting of methyl, ethyl, n-propyl, isopropyl, n-butyl, sec-butyl, isobutyl, tert-butyl, 1,1-dimethylpropyl, n-pentyl, sec-pentyl, n-hexyl and n-heptyl;

is a radical selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl and thiomorpholinyl;

or is a radical selected from the group consisting of phenyl, benzyl, phenethyl, naphthyl, (1,3)-benzodioxolyl, (1,4)-benzodioxanyl, thiophenyl, furanyl, pyrrolyl, pyrazolyl, pyranyl, pyridinyl, imidazolyl, indolyl, isoindolyl, benzo[b]furanyl, benzo[b]thiophenyl, thiazolyl, oxazolyl, isoxazolyl, pyridazinyl, pyrazinyl, pyrimidinyl, indazolyl, quinazolinyl, quinolinyl, isoquinolinyl, benzimidazolinyl, benzoxazolyl, benzisoxazolyl and benzothiazolyl, where the radical may be bonded via a —(CH$_2$)—, —(CH$_2$)—(CH$_2$)— or —(CH$_2$)—(CH$_2$)—(CH$_2$)— group and may in each case optionally be substituted by 1, 2, 3, 4 or 5 substituents selected independently from the group consisting of F, Cl, Br, I, —CN, —CF$_3$, —SF$_5$, —OH, —O—CH$_3$, —O—C$_2$H$_5$, —NH$_2$, —NO$_2$, —O—CF$_3$, —S—CF$_3$, —SH, —S—CH$_3$, —S—C$_2$H$_5$, methyl, ethyl, n-propyl, isopropyl, n-butyl, sec-butyl, isobutyl, tert-butyl, —C(=O)—OH, —C(=O)—O—CH$_3$, —C(=O)—O—C$_2$H$_5$, —C(=O)—O—C(CH$_3$)$_3$, —O—C(=O)—CH$_3$, —O—C(=O)—C$_2$H$_5$, —O—C(=O)—C(CH$_3$)$_3$, —N(CH$_3$)$_2$, —N(C$_2$H$_5$)$_2$, —NH—CH$_3$, —NH—C$_2$H$_5$, —NH—C(=O)—O—CH$_3$, —NH—C(=O)—O—C$_2$H$_5$, —NH—C(=O)—O—C(CH$_3$)$_3$, —C(=O)—H, —C(=O)—CH$_3$, —C(=O)—C$_2$H$_5$, —C(=O)—C(CH$_3$)$_3$, —C(=O)—NH$_2$, —C(=O)—NH—CH$_3$, —C(=O)—NH—C$_2$H$_5$, —C(=O)—N(CH$_3$)$_2$, —C(=O)—N—(C$_2$H$_5$)$_2$, —S(=O)$_2$—CH$_3$, —S(=O)$_2$—C$_2$H$_5$, —NH—S(=O)$_2$—CH$_3$, —NH—S(=O)$_2$—C$_2$H$_5$, —S(=O)$_2$—NH—CH$_3$ and —S(=O)$_2$—NH—C$_2$H$_5$;

$R^6$ is a hydrogen radical;
  is —(CH$_2$)—Z—R$^{26}$;
  or is —(CH$_2$)—OR$^7$;

$R^7$, $R^8$ and $R^9$ are each independently
  a radical selected from the group consisting of methyl, ethyl, n-propyl, isopropyl, n-butyl, sec-butyl, isobutyl, tert-butyl, 1,1-dimethylpropyl, n-pentyl, sec-pentyl, n-hexyl and n-heptyl;
  or a radical selected from the group consisting of benzyl and phenethyl, where the radical may in each case optionally be substituted by 1, 2, 3, 4 or 5 substituents selected independently from the group consisting of F, Cl, Br, I, —CN, —CF$_3$, —SF$_5$, —OH, —O—CH$_3$, —O—C$_2$H$_5$, —NH$_2$, —NO$_2$, —O—CF$_3$, —S—CF$_3$, —SH, —S—CH$_3$, —S—C$_2$H$_5$, methyl, ethyl, n-propyl, isopropyl, n-butyl, sec-butyl, isobutyl and tert-butyl;

$R^{10}$, $R^{11}$, $R^{12}$ and $R^{13}$, are each independently
  a radical selected from the group consisting of methyl, —CF$_3$, —CHF$_2$, —CH$_2$F, —CCl$_3$, —CBr$_3$, —CH$_2$—CN, —CH$_2$—NO$_2$, ethyl, —CF$_2$—CF$_3$, —CH$_2$—CF$_3$, —CCl$_2$-CCl$_3$, —CF$_2$—CH$_3$, —CH$_2$—CH$_2$—CN, —CH$_2$—CH$_2$—NO$_2$, n-propyl, isopropyl, n-butyl, sec-butyl, isobutyl, tert-butyl, 1,1-dimethylpropyl, n-pentyl, sec-pentyl, n-hexyl and n-heptyl;
  or a radical selected from the group consisting of phenyl, benzyl and phenethyl, where the radical may in each case optionally be substituted by 1, 2, 3, 4 or 5 substituents selected independently from the group consisting of F, Cl, Br, I, —CN, —CF$_3$, —SF$_5$, —OH, —O—CH$_3$, —O—C$_2$H$_5$, —NH$_2$, —NO$_2$, —O—CF$_3$, —S—CF$_3$, —SH, —S—CH$_3$, —S—C$_2$H$_5$, methyl, ethyl, n-propyl, isopropyl, n-butyl, sec-butyl, isobutyl and tert-butyl;

Z is O, O—C(=O), O—C(=O)—O, O—S(=O)$_2$, O—C(=S)—N(H) or O—C(=O)—N(H);

$R^{24}$ and $R^{25}$ are each independently
  a radical selected from the group consisting of phenyl, naphthyl, thiophenyl, furanyl and pyridinyl, where the radical may in each case optionally be substituted by 1, 2, 3, 4 or 5 substituents selected independently from the group consisting of F, Cl, Br, I, —CN, —CF$_3$, —SF$_5$, —OH, —O—CH$_3$, —O—C$_2$H$_5$, —NH$_2$, —NO$_2$, —O—CF$_3$, —S—CF$_3$, —SH, —S—CH$_3$, —S—C$_2$H$_5$, methyl, ethyl, n-propyl, isopropyl, n-butyl, sec-butyl, isobutyl, tert-butyl, —N(CH$_3$)$_2$, —N(C$_2$H$_5$)$_2$, —NH—CH$_3$ and —NH—C$_2$H$_5$;

$R^{26}$ is a —C(=O)—R$^{28}$ group;
  is a —S(=O)$_2$—R$^{29}$ group;
  is a radical selected from the group consisting of methyl, ethyl, n-propyl, isopropyl, n-butyl, sec-butyl, isobutyl, tert-butyl, 1,1-dimethylpropyl, n-pentyl, sec-pentyl, n-hexyl and n-heptyl;
  is a radical selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl and thiomorpholinyl;
  or is a radical selected from the group consisting of phenyl, benzyl, phenethyl, naphthyl, (1,3)-benzodioxolyl, (1,4)-benzodioxanyl, thiophenyl, furanyl, pyrrolyl, pyrazolyl, pyranyl, pyridinyl, imidazolyl, indolyl, isoindolyl, benzo[b]furanyl, benzo[b]thiophenyl, thiazolyl, oxazolyl, isoxazolyl, pyridazinyl, pyrazinyl, pyrimidinyl, indazolyl, quinazolinyl, quinolinyl, isoquinolinyl, benzimidazolinyl, benzoxazolyl, benzisoxazolyl and benzothiazolyl, where the radical may be bonded via a —(CH$_2$)—, —(CH$_2$)—(CH$_2$)— or —(CH$_2$)—(CH$_2$)—(CH$_2$)— group and may in each case optionally be substituted by 1, 2, 3, 4 or 5 substituents selected independently from the group consisting of F, Cl, Br, I, —CN, —CF$_3$, —SF$_5$, —OH, —O—CH$_3$, —O—C$_2$H$_5$, —NH$_2$, —NO$_2$, —O—CF$_3$, —S—CF$_3$, —SH, —S—CH$_3$, —S—C$_2$H$_5$, methyl, ethyl, n-propyl, isopropyl, n-butyl, sec-butyl, isobutyl, tert-butyl, —C(=O)—OH, —C(=O)—O—CH$_3$, —C(=O)—O—C$_2$H$_5$, —C(=O)—O—C(CH$_3$)$_3$, —O—C(=O)—CH$_3$, —O—C(=O)—C$_2$H$_5$, —O—C(=O)—C(CH$_3$)$_3$, —N(CH$_3$)$_2$, —N(C$_2$H$_5$)$_2$, —NH—CH$_3$, —NH—C$_2$H$_5$, —NH—C(=O)—O—CH$_3$, —NH—C(=O)—O—C$_2$H$_5$, —NH—C(=O)—O—C(CH$_3$)$_3$, —C(=O)—H, —C(=O)—CH$_3$, —C(=O)—C$_2$H$_5$, —C(=O)—C(CH$_3$)$_3$, —C(=O)—NH$_2$, —C(=O)—NH—CH$_3$, —C(=O)—NH—C$_2$H$_5$, —C(=O)—N—(CH$_3$)$_2$, —C(=O)—N—(C$_2$H$_5$)$_2$, —S(=O)$_2$—CH$_3$, —S(=O)$_2$—C$_2$H$_5$, —NH—S(=O)$_2$—CH$_3$, —NH—S(=O)$_2$—C$_2$H$_5$, —S(=O)$_2$—NH—CH$_3$ and —S(=O)$_2$—NH—C$_2$H$_5$;

$R^{27}$ is a hydrogen radical;
and
$R^{28}$ and $R^{29}$ are each independently
  a radical selected from the group consisting of phenyl, naphthyl, thiophenyl, furanyl and pyridinyl, where the radical may in each case optionally be substituted by 1, 2, 3, 4 or 5 substituents selected independently from the group consisting of F, Cl, Br, I, —CN, —CF$_3$, —SF$_5$, —OH, —O—CH$_3$, —O—C$_2$H$_5$, —NH$_2$, —NO$_2$, —O—CF$_3$, —S—CF$_3$, —SH, —S—CH$_3$, —S—C$_2$H$_5$, methyl, ethyl, n-propyl, isopropyl, n-butyl, sec-butyl, isobutyl, tert-butyl, —N(CH$_3$)$_2$, —N(C$_2$H$_5$)$_2$, —NH—CH$_3$ and —NH—C$_2$H$_5$;

excluding benzofused cycloheptanone derivatives of the general formula I in which X is CH$_2$; $R^6$ is a hydrogen radical or is —(CH$_2$)—Z—R$^{26}$; Z is O or O—C(=O); $R^{26}$ is an aliphatic radical; n is 1; Y is O or O—C(=O); $R^5$ is an aliphatic radical and $R^1$, $R^2$, $R^3$ and $R^4$ are each any of the aforementioned substituents;

in each case, as appropriate, in the form of one of their pure stereoisomers, especially enantiomers or diastereomers, of its racemates or in the form of a mixture of stereoisomers, especially of the enantiomers and/or diastereomers, in any mixing ratio, or in each case in the form of corresponding salts, or in each case in the form of corresponding solvates.

Very particular preference is given to substituted benzofused cycloheptanone derivatives of the above-specified general formula I in which n is 1;

X is CH$_2$, O, S, S(=O) or S(=O)$_2$;

Y is O, O—C(=O), O—C(=O)—O, O—S(=O)$_2$, O—C(=S)—N(H) or O—C(=O)—N(H);

$R^1$, $R^2$, $R^3$ and $R^4$, are each independently
  H, F, Cl, Br, —SF$_5$, —OH, —OR$^{10}$, —SR$^{11}$, —NR$^{12}$R$^{13}$,
  or a radical selected from the group consisting of methyl, —CF$_3$, —CHF$_2$, —CH$_2$F, —CCl$_3$, —CBr$_3$, —CH$_2$—CN, —CH$_2$—NO$_2$, ethyl, —CF$_2$—CF$_3$, —CH$_2$—CF$_3$, n-propyl, isopropyl, n-butyl, sec-butyl, isobutyl, tert-butyl, 1,1-dimethylpropyl and n-pentyl;

$R^5$ is a —C(=O)—$R^{24}$ group;
  is a —S(=O)$_2$—$R^{25}$ group;
  is a radical selected from the group consisting of methyl, ethyl, n-propyl, isopropyl, n-butyl, sec-butyl, isobutyl, tert-butyl, 1,1-dimethylpropyl, n-pentyl, sec-pentyl, n-hexyl and n-heptyl;
  is a radical selected from the group consisting of cyclopropyl, cyclobutyl, cyclopentyl, cyclohexyl, cycloheptyl, cyclopentenyl, cyclohexenyl and cycloheptenyl;
  or is a radical selected from the group consisting of phenyl, naphthyl, thiophenyl, furanyl, pyridinyl, indolyl, thiazolyl and oxazolyl, where the radical may in each case optionally be substituted by 1, 2, 3, 4 or 5 substituents selected independently from the group consisting of F, Cl, Br, —SF$_5$, —CF$_3$, —O—CH$_3$, —O—C$_2$H$_5$, —SCH$_3$, —SC$_2$H$_5$, —O—CF$_3$, —S—CF$_3$, methyl, ethyl, n-propyl, isopropyl, n-butyl, sec-butyl, isobutyl and tert-butyl;

$R^6$ is a hydrogen radical;
  is —(CH$_2$)—Z—$R^{26}$;
  or is —(CH$_2$)—O$R^{27}$;

$R^{10}$, $R^{11}$, $R^{12}$ and $R^{13}$ are each independently
  a radical selected from the group consisting of methyl, —CF$_3$, —CH$_2$F, —CF$_2$H, ethyl, —C$_2$F$_5$, n-propyl, isopropyl, n-butyl, sec-butyl, isobutyl, tert-butyl, 1,1-dimethylpropyl, n-pentyl, sec-pentyl, n-hexyl and n-heptyl;

Z is O, O—C(=O), O—C(=O)—O, O—S(=O)$_2$, O—C(=S)—N(H) or O—C(=O)—N(H);

$R^{24}$ and $R^{25}$ are each independently
  a radical selected from the group consisting of phenyl, naphthyl, thiophenyl, furanyl and pyridinyl, where the radical may in each case optionally be substituted by 1, 2, 3, 4 or 5 substituents selected independently from the group consisting of F, Cl, Br, I, —CF$_3$, —SF$_5$, —O—CH$_3$, —O—C$_2$H$_5$, —S—CF$_3$, methyl, ethyl, n-propyl, isopropyl, n-butyl, sec-butyl, isobutyl and tert-butyl;

$R^{26}$ is a —C(=O)—$R^{28}$ group;
  is a —S(=O)$_2$—$R^{29}$ group;
  is a radical selected from the group consisting of methyl, ethyl, n-propyl, isopropyl, n-butyl, sec-butyl, isobutyl, tert-butyl, 1,1-dimethylpropyl, n-pentyl, sec-pentyl, n-hexyl and n-heptyl;
  is a radical selected from the group consisting of cyclopropyl, cyclobutyl, cyclopentyl, cyclohexyl, cycloheptyl, cyclopentenyl, cyclohexenyl and cycloheptenyl;
  or is a radical selected from the group consisting of phenyl, naphthyl, thiophenyl, furanyl, pyridinyl, indolyl, thiazolyl and oxazolyl, where the radical may in each case optionally be substituted by 1, 2, 3, 4 or 5 substituents selected independently from the group consisting of F, Cl, Br, —SF$_5$, —CF$_3$, —O—CH$_3$, —O—C$_2$H$_5$, —SCH$_3$, —SC$_2$H$_5$, —O—CF$_3$, —S—CF$_3$, methyl, ethyl, n-propyl, isopropyl, n-butyl, sec-butyl, isobutyl and tert-butyl;

$R^{27}$ is a hydrogen radical;

and $R^{28}$ and $R^{29}$ are each independently a radical selected from the group consisting of phenyl, naphthyl, thiophenyl, furanyl and pyridinyl, where the radical may in each case optionally be substituted by 1, 2, 3, 4 or 5 substituents selected independently from the group consisting of F, Cl, Br, I, —CF$_3$, —SF$_5$, —O—CH$_3$, —O—C$_2$H$_5$, —S—CF$_3$, methyl, ethyl, n-propyl, isopropyl, n-butyl, sec-butyl, isobutyl and tert-butyl;

excluding benzofused cycloheptanone derivatives of the general formula I in which X is CH$_2$; $R^6$ is a hydrogen radical or is —(CH$_2$)—Z—$R^{26}$; Z is O or O—C(=O); $R^{26}$ is an aliphatic radical; n is 1; Y is O or O—C(=O); $R^5$ is an aliphatic radical and $R^1$, $R^2$, $R^3$ and $R^4$ are each any of the aforementioned substituents;

in each case, as appropriate, in the form of one of their pure stereoisomers, especially enantiomers or diastereomers, of its racemates or in the form of a mixture of stereoisomers, especially of the enantiomers and/or diastereomers, in any mixing ratio, or in each case in the form of corresponding salts, or in each case in the form of corresponding solvates.

Even more preferred are substituted benzofused cycloheptanone derivatives of the above-specified general formula I selected from the group consisting of

[1] pentylcarbamic acid 5-oxo-2,3,4,5-tetrahydrobenzo[b]thiepin-4-ylmethyl ester

[2] phenylcarbamic acid 4-(phenylcarbamoyloxymethyl)-5-oxo-2,3,4,5-tetrahydrobenzo[b]thiepin-4-ylmethyl ester

[3] phenylcarbamic acid 5-oxo-2,3,4,5-tetrahydrobenzo[b]thiepin-4-ylmethyl ester

[4] (3-trifluoromethylphenyl)carbamic acid 5-oxo-2,3,4,5-tetrahydro-benzo[b]thiepin-4-ylmethyl ester

[5] (4-bromophenyl)carbamic acid 5-oxo-2,3,4,5-tetrahydro-benzo[b]thiepin-4-ylmethyl ester

[6] cyclohexylcarbamic acid 4-hydroxymethyl-5-oxo-2,3,4,5-tetrahydro-benzo[b]thiepin-4-ylmethyl ester

[7] cyclohexylcarbamic acid 5-oxo-2,3,4,5-tetrahydrobenzo[b]thiepin-4-ylmethyl ester

[8] cyclohexylcarbamic acid 6-(cyclohexylcarbamoyloxymethyl)-5-oxo-6,7,8,9-tetrahydro-5H-benzocyclohepten-6-ylmethyl ester

[9] phenylthiocarbamic acid O-(4-hydroxymethyl-5-oxo-2,3,4,5-tetrahydro-benzo[b]thiepin-4-ylmethyl)ester

[10] N-(4-methylphenylsulfonyl)carbamic acid 5-oxo-2,3,4,5-tetrahydro-benzo[b]thiepin-4-ylmethyl ester

[11] naphthalen-1-ylthiocarbamic acid O-(4-hydroxymethyl-5-oxo-2,3,4,5-tetrahydrobenzo[b]thiepin-4-ylmethyl)ester

[12] pentylcarbamic acid 4-hydroxymethyl-5-oxo-2,3,4,5-tetrahydro-benzo[b]oxepin-4-ylmethyl ester

[13] pentylcarbamic acid 4-hydroxymethyl-5-oxo-2,3,4,5-tetrahydro-benzo[b]thiepin-4-ylmethyl ester

[14] pentylcarbamic acid 4-(pentylcarbamoyloxymethyl)-5-oxo-2,3,4,5-tetrahydrobenzo[b]thiepin-4-ylmethyl ester

[15] phenylthiocarbamic acid O-(4-hydroxymethyl-5-oxo-2,3,4,5-tetrahydro-benzo[b]oxepin-4-ylmethyl)ester

[16] 2,4-difluorophenylcarbamic acid 4-(2,4-difluorophenylcarbamoyloxy-methyl)-5-oxo-2,3,4,5-tetrahydrobenzo[b]oxepin-4-ylmethyl ester

[17] (3-trifluoromethylphenyl)thiocarbamic acid O-(4-hydroxymethyl-5-oxo-2,3,4,5-tetrahydrobenzo[b]thiepin-4-ylmethyl)ester

[18] (3-trifluoromethylphenyl)thiocarbamic acid O-(4-hydroxymethyl-5-oxo-2,3,4,5-tetrahydrobenzo[b]oxepin-4-ylmethyl)ester

[19] benzoylcarbamic acid 4-benzoylcarbamoyloxymethyl-5-oxo-2,3,4,5-tetrahydrobenzo[b]oxepin-4-ylmethyl ester

[20] (2,4-difluorophenyl)carbamic acid 4-hydroxymethyl-5-oxo-2,3,4,5-tetrahydrobenzo[b]thiepin-4-ylmethyl ester

[21] (2,4-difluorophenyl)thiocarbamic acid O-(4-hydroxymethyl-5-oxo-2,3,4,5-tetrahydrobenzo[b]thiepin-4-ylmethyl)ester

[22] (3-trifluoromethylphenyl)thiocarbamic acid O-(6-hydroxymethyl-5-oxo-6,7,8,9-tetrahydro-5H-benzocyclohepten-6-ylmethyl)ester

[23] (2,4-difluorophenyl)thiocarbamic acid O-(4-hydroxymethyl-5-oxo-2,3,4,5-tetrahydrobenzo[b]oxepin-4-ylmethyl)ester

[24] (2,4-difluorophenyl)thiocarbamic acid O-(6-hydroxymethyl-5-oxo-6,7,8,9-tetrahydro-5H-benzocyclohepten-6-ylmethyl)ester

[25] (3-trifluoromethylphenyl)carbamic acid 4-(3-trifluoromethylphenyl)-carbamoyloxymethyl-5-oxo-2,3,4,5-tetrahydrobenzo[b]oxepin-4-ylmethyl ester

[26] butylcarbamic acid 4-hydroxymethyl-5-oxo-2,3,4,5-tetrahydro-benzo[b]thiepin-4-ylmethyl ester

[27] butylcarbamic acid 4-(butylcarbamoyloxymethyl)-5-oxo-2,3,4,5-tetrahydrobenzo[b]thiepin-4-ylmethyl ester and

[28] (4-trifluoromethoxyphenyl)carbamic acid 4-hydroxymethyl-5-oxo-2,3,4,5-tetrahydrobenzo[b]thiepin-4-ylmethyl ester;

in each case, as appropriate, in the form of one of its pure stereoisomers, especially enantiomers or diastereomers, of its racemates or in the form of a mixture of stereoisomers, especially of the enantiomers and/or diastereomers, in any mixing ratio, or in each case in the form of corresponding salts, or in each case in the form of corresponding solvates.

Preference may likewise be given to inventive compounds which, in the FLIPR assay, in a concentration of 10 μM, have an inhibition of the $Ca^{2+}$ ion current in dorsal root ganglia of rats of at least 10%, preferably of at least 30%, more preferably of at least 50%, even more preferably of at least 70%, even more preferably of at least 90%, compared to the maximum achievable inhibition of the $Ca^{2+}$ ion current with capsaicin in a concentration of 10 μM.

In the FLIPR assay, the $Ca^{2+}$ current is quantified with the aid of a $Ca^{2+}$-sensitive dye (Fluo-4 type, Molecular Probes Europe BV, Leiden, the Netherlands) in the fluorescent imaging plate reader (FLIPR, Molecular Devices, Sunnyvale, USA), as described below.

The present invention further provides a process for preparing inventive compounds of the above-specified general formula I, according to which at least one compound of the general formula II

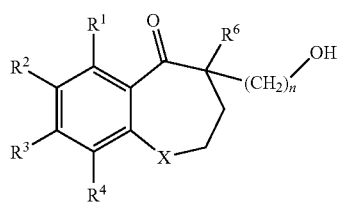

II in which X, n and $R^1$ to $R^4$ are each as defined above and $R^6$ is a hydrogen radical, $—(CH_2)_q—NH_2$ or $—(CH_2)_q—OR^{27}$, where q and $R^{27}$ are each as defined above, in a reaction medium, optionally in the presence of at least one base, preferably in the presence of at least one organic base, is reacted with at least one compound of the general formula $R^5—N=C=O$ and optionally at least one compound of the general formula $R^{26}—N=C=O$, where $R^5$ and $R^{26}$ may be defined identically as above, to give at least one compound of the general formula Ia

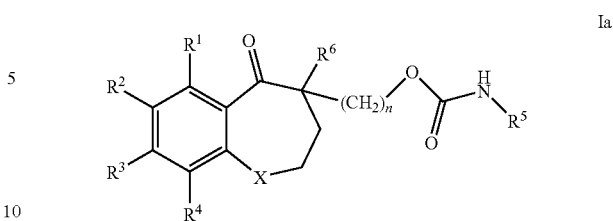

Ia in which X, n and $R^1$ to $R^5$ are each as defined above and $R^6$ is a hydrogen radical, is $—(CH_2)_p—O—C(=O)—N(H)—R^{26}$, is $—(CH_2)_p—N(H)—C(=O)—N(H)—R^{26}$ or is $—(CH_2)_q—OR^{27}$;

where p, q, $R^{26}$ and $R^{27}$ are each as defined above; and the latter is optionally purified and/or isolated;

or at least one compound of the general formula II in which X, n and $R^1$ to $R^4$ are each as defined above and $R^6$ is a hydrogen radical or $—(CH_2)_q—OR^{27}$, where q and $R^{27}$ are each as defined above; in a reaction medium, optionally in the presence of at least one base, preferably in the presence of at least one organic base, is reacted with at least one compound of the general formula $R^5—S(=O)_2$-LG and optionally at least one compound of the general formula $R^{26}—S(=O)_2$—

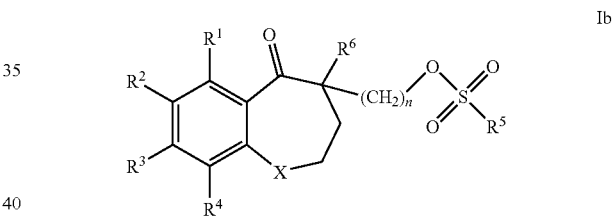

Ib

LG, where $R^5$ and $R^{26}$ may be defined identically as above and LG is a leaving group, preferably a halogen atom, more preferably a chlorine atom, to give at least one compound of the general formula Ib, in which X, n and $R^1$ to $R^5$ are each as defined above and $R^6$ is a hydrogen radical, is $—(CH_2)_p—O—S(=O)_2—R^{26}$ or is $—(CH_2)_q—OR^{27}$; where p, q, $R^{26}$ and $R^{27}$ may each be as defined above; and the latter is optionally purified and/or isolated;

or at least one compound of the general formula II in which X, n and $R^1$ to $R^4$ are each as defined above and $R^6$ is a hydrogen radical or $—(CH_2)_q—OR^{27}$ where q and $R^{27}$ are each as defined above; in a reaction medium, optionally in the presence of a base, preferably in the presence of at least one organic base, is reacted with at least one compound of the general formula $R^5—C(=O)$-LG and optionally at least one compound of the general formula $R^{26}—C(=O)$-LG, where $R^5$ and $R^{26}$ are optionally defined identically as above and LG is a leaving group, preferably a halogen atom, more preferably a chlorine atom, to give at least one compound of the general formula Ic

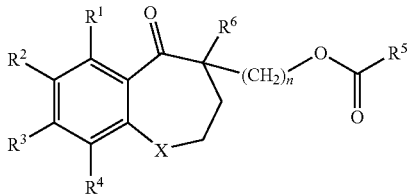

Ic in which X, n and $R^1$ to $R^5$ are each as defined above and $R^6$ is a hydrogen radical, is $-(CH_2)_p-O-C(=O)-R^{26}$ or is $-(CH_2)_q-OR^{27}$; where p, q, $R^{26}$ and $R^{27}$ are each as defined above; and the latter is optionally purified and/or isolated;

or at least one compound of the general formula II in which X, n and $R^1$ to $R^4$ are each as defined above and $R^6$ is a hydrogen radical or $-(CH_2)_q-OR^{27}$ where q and $R^{27}$ are each as defined above; in a reaction medium, optionally in the presence of at least one base, preferably in the presence of at least one organic base, is reacted with at least one compound of the general formula $R^5-O-C(=O)$-LG and optionally at least one compound of the general formula $R^{26}-O-C(=O)$-LG, where $R^5$ and $R^{26}$ may be defined identically as above and LG is a leaving group, preferably a halogen atom, more preferably a chlorine atom, to give at least one compound of the general formula Id

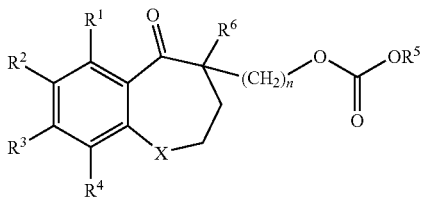

Id in which X, n and $R^1$ to $R^5$ are each as defined above and $R^6$ is a hydrogen radical, is $-(CH_2)_p-O-C(=O)-O-R^{26}$ or is $-(CH_2)_q-OR^{27}$; where p, q, $R^{26}$ and $R^{27}$ are each as defined above; and the latter is optionally purified and/or isolated;

or at least one compound of the general formula II in which X, n and $R^1$ to $R^4$ are each as defined above and $R^6$ is a hydrogen radical, $-(CH_2)_q-NH_2$ or $-(CH_2)_q-OR^{27}$, where q and $R^{27}$ are each as defined above; in a reaction medium, in the presence of at least one base, preferably in the presence of at least one metal hydride salt, more preferably in the presence of potassium hydride and/or sodium hydride, is reacted with at least one compound of the general formula $R^5$-LG and optionally at least one compound of the general formula $R^{26}$-LG, where $R^5$ and $R^{26}$ may be defined identically as above and LG is a leaving group, preferably a halogen atom, more preferably a chlorine atom, to give at least one compound of the general formula Ie,

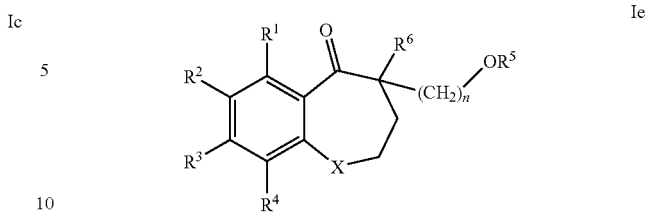

Ie in which X, n and $R^1$ to $R^5$ are each as defined above and $R^6$ is a hydrogen radical, is $-(CH_2)_p-OR^{26}$, is $-(CH_2)_p-NHR^{26}$ or is $-(CH_2)_q-OR^{27}$; where p, q, $R^{26}$ and $R^{27}$ are each as defined above; and the latter is optionally purified and/or isolated;

or at least one compound of the general formula II in which X, n and $R^1$ to $R^4$ are each as defined above and $R^6$ is a hydrogen radical, $-(CH_2)_q-NH_2$ or $-(CH_2)_q-OR^{27}$, where q and $R^{27}$ are each as defined above, in a reaction medium, optionally in the presence of at least one base, preferably in the presence of at least one organic base, is reacted with at least one compound of the general formula $R^5-N=C=S$ and optionally at least one compound of the general formula $R^{26}-N=C=S$, where $R^5$ and $R^{26}$ may be defined identically as above, to give at least one compound of the general formula If

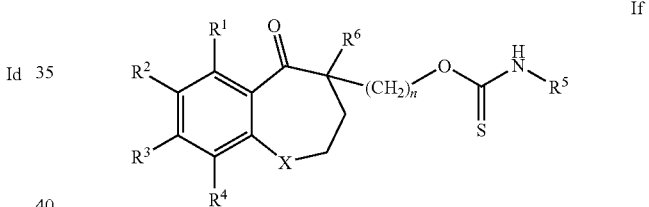

If in which X, n and $R^1$ to $R^5$ are each as defined above and $R^6$ is a hydrogen radical, is $-(CH_2)_p-O-C(=S)-N(H)-R^{26}$, is $-(CH_2)_p-N(H)-C(=S)-N(H)-R^{26}$ or is $-(CH_2)_q-OR^{27}$; where p, q, $R^{26}$ and $R^{27}$ are each as defined above; and the latter is optionally purified and/or isolated;

and optionally at least one compound of the general formula Ia, Ib, Ic, Id, Ie or If in which X, n and $R^1$ to $R^5$ are each as defined above and Y is O, $O-C(=O)$, $O-C(=O)-O$, $O-S(=O)_2$, $O-C(=S)-N(H)$ or $O-C(=O)-N(H)$ and $R^6$ is $-(CH_2)_q-OR^{27}$ where $R^{27}$ is a hydrogen radical; in a reaction medium, optionally in the presence of at least one base, preferably in the presence of at least one organic base, is reacted with at least one compound of the general formula $R^{26}-N=C=O$ to give at least one compound of the general formula Ia, Ib, Ic, Id or Ie in which X, n and $R^1$ to $R^5$ are each as defined above and Y is O, $O-C(=O)$, $O-C(=O)-O$, $O-S(=O)_2$, $O-C(=S)-N(H)$ or $O-C(=O)-N(H)$ and $R^6$ is $-(CH_2)_p-O-C(=O)-N(H)-R^{26}$; and the latter is optionally purified and/or isolated;

or optionally at least one compound of the general formula Ia, Ib, Ic, Id, Ie or If in which X, n and $R^1$ to $R^5$ are each as defined above and Y is O, $O-C(=O)$, $O-C(=O)-O$, $O-S(=O)_2$, $O-C(=S)-N(H)$ or $O-C(=O)-N(H)$ and $R^6$ is —$(CH_2)_q$—$OR^{27}$ where $R^{27}$ is a hydrogen radical; in a reaction medium, optionally in the presence of at least one base, preferably in the presence of at least one organic base, is reacted with at least one compound of the general formula $R^{26}$—$S(=O)_2$-LG to give at least one compound of the general formula Ia, Ib, Ic, Id or Ie in which X, n and $R^1$ to $R^5$ are each as defined above and Y is O, O—C(=O), O—C(=O)—O, O—S(=O)$_2$, O—C(=S)—N(H) or O—C(=O)—N(H) and $R^6$ is —$(CH_2)_p$—O—S(=O)$_2$—$R^{26}$; and the latter is optionally purified and/or isolated;

or optionally at least one compound of the general formula Ia, Ib, Ic, Id, Ie or If in which X, n and $R^1$ to $R^5$ are each as defined above and Y is O, O—C(=O), O—C(=O)—O, O—S(=O)$_2$, O—C(=S)—N(H) or O—C(=O)—N(H) and $R^6$ is —$(CH_2)_q$—$OR^{27}$ where $R^{27}$ is a hydrogen radical; in a reaction medium, optionally in the presence of at least one base, preferably in the presence of at least one organic base, is reacted with at least one compound of the general formula $R^{26}$—C(=O)-LG to give at least one compound of the general formula Ia, Ib, Ic, Id or Ie in which X, n and $R^1$ to $R^5$ are each as defined above and Y is O, O—C(=O), O—C(=O)—O, O—S(=O)$_2$, O—C(=S)—N(H) or O—C(=O)—N(H) and $R^6$ is —$(CH_2)_p$—O—C(=O)—$R^{26}$; and the latter is optionally purified and/or isolated;

or optionally at least one compound of the general formula Ia, Ib, Ic, Id, Ie or If in which X, n and $R^1$ to $R^5$ are each as defined above and Y is O, O—C(=O), O—C(=O)—O, O—S(=O)$_2$, O—C(=S)—N(H) or O—C(=O)—N(H) and $R^6$ is —$(CH_2)_q$—$OR^{27}$ where $R^{27}$ is a hydrogen radical; in a reaction medium, optionally in the presence of at least one base, preferably in the presence of at least one organic base, is reacted with at least one compound of the general formula $R^{26}$—O—C(=O)-LG to give at least one compound of the general formula Ia, Ib, Ic, Id or Ie in which X, n and $R^1$ to $R^5$ are each as defined above and Y is O, O—C(=O), O—C(=O)—O, O—S(=O)$_2$, O—C(=S)—N(H) or O—C(=O)—N(H) and $R^6$ is —$(CH_2)_p$—O—C(=O)—O—$R^{26}$; and the latter is optionally purified and/or isolated;

or optionally at least one compound of the general formula Ia, Ib, Ic, Id, Ie or If in which X, n and $R^1$ to $R^5$ are each as defined above and Y is O, O—C(=O), O—C(=O)—O, O—S(=O)$_2$, O—C(=S)—N(H) or O—C(=O)—N(H) and $R^6$ is —$(CH_2)_q$—$OR^{27}$ where $R^{27}$ is a hydrogen radical; in a reaction medium, in the presence of at least one base, preferably in the presence of at least one metal hydride salt, more preferably in the presence of potassium hydride and/or sodium hydride, is reacted with at least one compound of the general formula $R^{26}$-LG to give at least one compound of the general formula Ia, Ib, Ic, Id or Ie in which X, n and $R^1$ to $R^5$ are each as defined above and Y is O, O—C(=O), O—C(=O)—O, O—S(=O)$_2$, O—C(=S)—N(H) or O—C(=O)—N(H) and $R^6$ is —$(CH_2)_p$—O—$R^{26}$; and the latter is optionally purified and/or isolated;

or optionally at least one compound of the general formula Ia, Ib, Ic, Id, Ie or If in which X, n and $R^1$ to $R^5$ are each as defined above and Y is O, O—C(=O), O—C(=O)—O, O—S(=O)$_2$, O—C(=S)—N(H) or O—C(=O)—N(H) and $R^6$ is —$(CH_2)_q$—$OR^{27}$ where $R^{27}$ is a hydrogen radical; in a reaction medium, optionally in the presence of at least one base, preferably in the presence of at least one organic base, is reacted with at least one compound of the general formula $R^{26}$—N=C=S to give at least one compound of the general formula Ia, Ib, Ic, Id or Ie; in which X, n and $R^1$ to $R^5$ are each as defined above and Y is O, O—C(=O), O—C(=O)—O, O—S(=O)$_2$, O—C(=S)—N(H) or O—C(=O)—N(H) and $R^6$ is —$(CH_2)_p$—O—C(=S)—N(H)—$R^{26}$; and the latter is optionally purified and/or isolated;

or optionally at least one compound of the general formula Ia, Ib, Ic, Id, Ie or If in which X, n and $R^1$ to $R^5$ are each as defined above and Y is O, O—C(=O), O—C(=O)—O, O—S(=O)$_2$, O—C(=S)—N(H) or O—C(=O)—N(H) and $R^6$ is —$(CH_2)_p$—$NH_2$; in a reaction medium, optionally in the presence of at least one base, preferably in the presence of at least one organic base, is reacted with at least one compound of the general formula $R^{26}$—N=C=S to give at least one compound of the general formula Ia, Ib, Ic, Id or Ie in which X, n and $R^1$ to $R^5$ are each as defined above and Y is O, O—C(=O), O—C(=O)—O, O—S(=O)$_2$, O—C(=S)—N(H) or O—C(=O)—N(H) and $R^6$ is —$(CH_2)_p$—N—C(=S)—N(H)—$R^{26}$; and the latter is optionally purified and/or isolated;

or optionally at least one compound of the general formula Ia, Ib, Ic, Id, Ie or If in which X, n and $R^1$ to $R^5$ are each as defined above and Y is O, O—C(=O), O—C(=O)—O, O—S(=O)$_2$, O—C(=S)—N(H) or O—C(=O)—N(H) and $R^6$ is —$(CH_2)_p$—$NH_2$; in a reaction medium, optionally in the presence of at least one base, preferably in the presence of at least one organic base, is reacted with at least one compound of the general formula $R^{26}$—N=C=O to give at least one compound of the general formula Ia, Ib, Ic, Id or Ie in which X, n and $R^1$ to $R^5$ are each as defined above and Y is O, O—C(=O), O—C(=O)—O, O—S(=O)$_2$, O—C(=S)—N(H) or O—C(=O)—N(H) and $R^6$ is —$(CH_2)_p$—N—C(=O)—N(H)—$R^{26}$; and the latter is optionally purified and/or isolated;

or optionally at least one compound of the general formula Ia, Ib, Ic, Id, Ie or If in which X, n and $R^1$ to $R^5$ are each as defined above and Y is O, O—C(=O), O—C(=O)—O, O—S(=O)$_2$, O—C(=S)—N(H) or O—C(=O)—N(H) and $R^6$ is —$(CH_2)_p$—$NH_2$; in a reaction medium, in the presence of at least one base, preferably in the presence of at least one metal hydride salt, more preferably in the presence of potassium hydride and/or sodium hydride, is reacted with at least one compound of the general formula $R^{26}$-LG to give at least one compound of the general formula Ia, Ib, Ic, Id or Ie; in which X, n and $R^1$ to $R^5$ are each as defined above and Y is O, O—C(=O), O—C(=O)—O, O—S(=O)$_2$, O—C(=S)—N(H) or O—C(=O)—N(H) and $R^6$ is —$(CH_2)_p$—N(H)—$R^{26}$; and the latter is optionally purified and/or isolated;

and optionally at least one compound of the general formula Ia, Ib, Ic, Id, Ie or If in which n, $R^1$ to $R^6$ and Y are each as defined above and X is S in a reaction medium, in the presence of sodium metaperiodate, is converted to at least one compound of the general formula Ia, Ib, Ic, Id or Ie in which n, $R^1$ to $R^6$ and Y are each as defined above and X is S(=O); and the latter is optionally purified and/or isolated;

and optionally at least one compound of the general formula Ia, Ib, Ic, Id, Ie or If, in which n, $R^1$ to $R^6$ and Y are each as defined above and X is S in a reaction medium, in the presence of hydrogen peroxide and acetic acid, is converted to at least one compound of the general formula Ia, Ib, Ic, Id or Ie in which n, $R^1$ to $R^6$ and Y are each as defined above and X is S(=O)$_2$; and the latter is optionally purified and/or isolated.

The present invention further provides a process for preparing inventive compounds of the above-specified formula I, according to which at least one compound of the general formula II

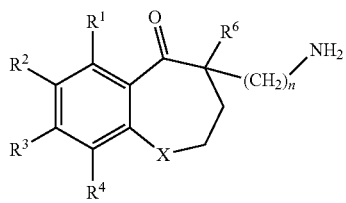

II in which X, n and R¹ to R⁴ are each as defined above and R⁶ is a hydrogen radical or is —(CH₂)$_p$—NH₂ where q is as defined above in a reaction medium, optionally in the presence of at least one base, preferably in the presence of at least one organic base, is reacted with at least one compound of the general formula R⁵—N═C═O and optionally at least one compound of the general formula R²⁶—N═C═O, where R⁵ and R²⁶ may be defined identically as above to give at least one compound of the general formula Ig

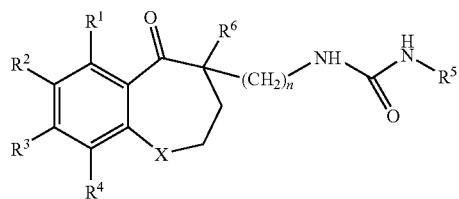

Ig in which X, n and R¹ to R⁵ are each as defined above and R⁶ is a hydrogen radical or is —(CH₂)$_p$—N(H)—C(═O)—N(H)—R²⁶ where p and R²⁶ are each as defined above; and the latter is optionally purified and/or isolated;

or at least one compound of the general formula III in a reaction medium, optionally in the presence of at least one base, preferably in the presence of at least one organic base, is reacted with at least one compound of the general formula R⁵—N═C═S and optionally at least one compound of the general formula R²⁶—N═C═S, where R⁵ and R²⁶ may be defined identically as above, to give at least one compound of the general formula Ih

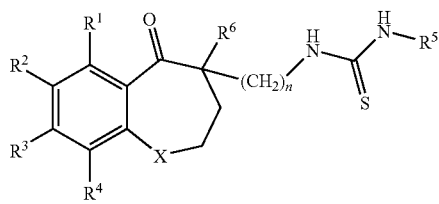

Ih in which X, n and R¹ to R⁵ are each as defined above and R⁶ is a hydrogen radical or is —(CH₂)$_p$—N(H)—C(═S)—N(H)—R²⁶ where p and R²⁶ are each as defined above; and the latter is optionally purified and/or isolated;

or at least one compound of the general formula III in a reaction medium, in the presence of at least one base, preferably in the presence of at least one metal hydride salt, more preferably in the presence of sodium hydride and/or potassium hydride, is reacted with a least one compound of the general formula R⁵-LG and optionally at least one compound of the general formula R²⁶-LG, where R⁵ and R²⁶ may be defined identically as above and LG is a leaving group, preferably a halogen atom, more preferably a chlorine atom, to give at least one compound of the general formula Ik

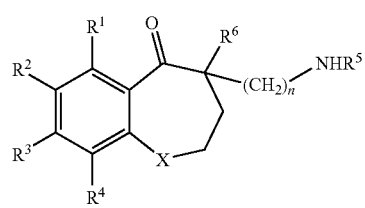

Ik in which X, n and R¹ to R⁵ are each as defined above and R⁶ is a hydrogen radical or is —(CH₂)$_p$—R²⁶ where p and R²⁶ are each as defined above; and the latter is optionally purified and/or isolated;

or optionally at least one compound of the general formula Ig, Ih or Ik in which X, n and R¹ to R⁵ are each as defined above and Y is N(H)—C(═O)—N(H) or N(H)—C(═S)—N(H) and R⁶ is —(CH₂)$_p$—NH₂; in a reaction medium, optionally in the presence of at least one base, preferably in the presence of at least one organic base, is reacted with at least one compound of the general formula R²⁶—N═C═O to give at least one compound of the general formula Ig, Ih or Ik in which X, n and R¹ to R⁵ are each as defined above and Y is N(H)—C(═O)—N(H) or N(H)—C(═S)—N(H) and R⁶ is —(CH₂)$_p$—N(H)—C(═O)—N(H)—R²⁶; and the latter is optionally purified and/or isolated;

or optionally at least one compound of the general formula Ig, Ih or Ik in which X, n and R¹ to R⁵ are each as defined above and Y is N(H)—C(═O)—N(H) or N(H)—C(═S)—N(H) and R⁶ is —(CH₂)$_p$—NH₂; in a reaction medium, optionally in the presence of at least one base, preferably in the presence of at least one organic base, is reacted with at least one compound of the general formula R²⁶—N═C═S to give at least one compound of the general formula Ig, Ih or Ik in which X, n and R¹ to R⁵ are each as defined above and Y is N(H)—C(═O)—N(H) or N(H)—C(═S)—N(H) and R⁶ is —(CH₂)$_p$—N(H)—C(═S)—N(H)—R²⁶; and the latter is optionally purified and/or isolated;

or optionally at least one compound of the general formula Ig, Ih or Ik in which X, n and R¹ to R⁵ are each as defined above and Y is N(H)—C(═O)—N(H) or N(H)—C(═S)—N(H) and R⁵ is —(CH₂)$_p$—NH₂; in a reaction medium, in the presence of at least one base, preferably in the presence of at least one metal hydride salt, more preferably in the presence of potassium hydride and/or sodium hydride, is reacted with at least one compound of the general formula R²⁶-LG to give at least one compound of the general formula Ig, Ih or Ik in which X, n and R¹ to R⁵ are each as defined above and Y is N(H)—C(═O)—N(H) or N(H)—C(═S)—N(H) and R⁶ is —(CH₂)$_p$—N(H)—R²⁶; and the latter is optionally purified and/or isolated;

and optionally at least one compound of the general formula Ig, Ih or Ik in which n, R¹ to R⁶ and Y are each as defined above and X is S in a reaction medium in the presence of sodium metaperiodate is converted to at least one compound of the general formula Ia, Ib, Ic, Id or Ie in which n, R¹ to R⁵ and Y are each as defined above and X is S(═O); and the latter is optionally purified and/or isolated;

and optionally at least one compound of the general formula Ig, Ih or Ik in which n, $R^1$ to $R^6$ and Y are each as defined above and X is S in a reaction medium in the presence of hydrogen peroxide and acetic acid is converted to at least one compound of the general formula Ia, Ib, Ic, Id or Ie in which n, $R^1$ to $R^6$ and Y are each as defined above and X is $S(=O)_2$; and the latter is optionally purified and/or isolated.

The reaction of compounds of the general formulae II, III, Ia, Ib, Ic, Id, Ie, If, Ig, Ih and Ik with isocyanates or isothiocyanates of the general formulae $R^5$—N=C=O, $R^5$—N=C=S, $R^{26}$—N=C=O and $R^{26}$—N=C=S is effected in a reaction medium, preferably selected from the group consisting of acetonitrile, dichloromethane, chloroform, tetrahydrofuran, diethyl ether, toluene, benzene, ethanol, methanol, water and corresponding mixtures, optionally in the presence of at least one base, preferably in the presence of at least one base selected from the group consisting of triethylamine, N-methylmorpholine, pyridine, 4,4-dimethylaminopyridine and diisopropylethylamine, at temperatures between 0° C. and 100° C. Preference is given to effecting the reaction in a reaction medium selected from the group consisting of diethyl ether, tetrahydrofuran, dichloromethane and chloroform with irradiation by microwaves.

The reaction of compounds of the general formulae II, III, Ia, Ib, Ic, Id, Ie, If, Ig, Ih and Ik with carboxylic acid derivatives, carbonic acid derivatives or sulfonic acid derivatives of the general formulae $R^5$—C(=O)-LG, $R^{26}$—C(=O)-LG, $R^5$—O—C(=O)-LG, $R^{26}$—O—C(=O)-LG, $R^5$—S(=O)$_2$-LG and $R^{26}$—S(=O)$_2$-LG is effected in a reaction medium, preferably selected from the group consisting of diethyl ether, pyridine, tetrahydrofuran, acetonitrile, methanol, ethanol, dimethylformamide, dichloromethane and corresponding mixtures, optionally in the presence of an organic base, preferably selected from the group consisting of triethylamine, 4,4-dimethylaminopyridine, pyridine and diisopropylethylamine, or of an inorganic base, at temperatures of preferably from −70° C. to 100° C.

The reaction of compounds of the general formulae II, III, Ia, Ib, Ic, Id, Ie, If, Ig, Ih and Ik with compounds of the general formulae $R^5$-LG and $R^{26}$-LG is effected in a reaction medium, preferably selected from the group consisting of dichloromethane, toluene, tetrahydrofuran, acetonitrile, diethyl ether, dioxane and corresponding mixtures, optionally in the presence of at least one base, preferably in the presence of at least one metal hydride salt, more preferably in the presence of sodium hydride and/or potassium hydride.

The compounds of the general formula II can be obtained as described in scheme 1.

Scheme 1.

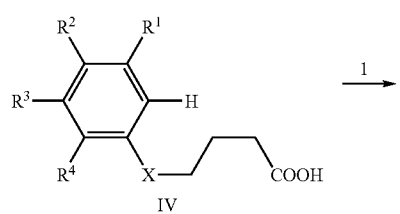

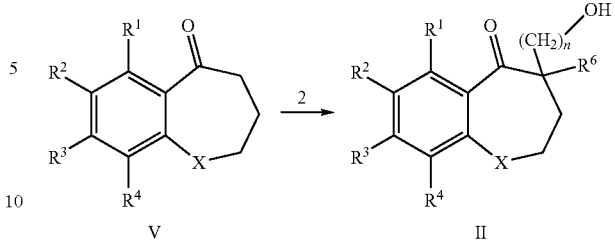

In stage 1, compounds of the general formula IV in which $R^1$ to $R^4$ are each as defined above and X is O, S, N(H), N($R^7$), N[C(=O)—$R^8$] or N[C(=O)—O—$R^9$] are converted in an acidic reaction medium, preferably in an acidic reaction medium selected from the group consisting of sulfuric acid and polyphosphoric acid, more preferably in polyphosphoric acid, at temperatures between 20° C. and 100° C., to compounds of the general formula VI in which $R^1$ to $R^4$ are each as defined above and X is O, S, N(H), N($R^7$), N[C(=O)—$R^8$] or N[C(=O)—O—$R^9$].

The synthesis of 3,4-dihydro-2H-benzo[b]thiepin-5-one (general formula V, $R^1$ to $R^4$ are each H and X is S) is described by V. J. Traynelis et al. in Journal of Organic Chemistry 1961, 26, 2728-2733. The synthesis of 3,4-dihydro-2H-benzo[b]oxepine (general formula V, $R^1$ to $R^4$ are each H and X is O) is described by G. Fontaine et al. in Annales de Chimie 1968, 3, 179-191. The corresponding descriptions are hereby included as a reference and form part of the present disclosure.

In stage 2, compounds of the general formula VI in which $R^1$ to $R^4$ are each as defined above and X is $CH_2$, O, S, N(H), N($R^7$), N[C(=O)—$R^8$] or N[C(=O)—O—$R^9$] from tetrahydrofuran, methanol, ethanol, isopropanol, water, dimethylformamide, dichloromethane, toluene, diethyl ether and corresponding mixtures in the presence of at least one base, preferably in the presence of at least one inorganic base, more preferably in the presence of potassium carbonate, sodium carbonate, lithium carbonate and magnesium carbonate, are reacted with formaldehyde, a formaldehyde equivalent or aqueous formalin solution at temperatures between 20° C. and 80° C. to give compounds of the general formula II in which $R^1$ to $R^4$ and $R^6$ are each as defined above, n is 1 and X is $CH_2$, O, S, N(H), N($R^7$), N[C(=O)—$R^8$] or N[C(=O)—O—$R^9$].

Optionally, compounds of the general formula II in which $R^1$ to $R^4$ and $R^6$ are each as defined above, n is 1 and X is S, in a reaction medium, preferably in a reaction medium selected from the group consisting of methanol, ethanol, isopropanol, water and corresponding mixtures, at temperatures between 0° C. and 50° C., are reacted with sodium metaperiodate to give compounds of the general formula II in which $R^1$ to $R^4$ and $R^6$ are each as defined above, n is 1 and X is S(=O).

Optionally, compounds of the general formula II in which $R^1$ to $R^4$ and $R^6$ are each as defined above, n is 1 and X is S, in a reaction medium, preferably in a reaction medium selected from the group consisting of methanol, ethanol, isopropanol, water and corresponding mixtures, at temperatures between 0° C. and 100° C., are reacted with acetic acid and with aqueous hydrogen peroxide solution to give compounds of the general formula II in which $R^1$ to $R^4$ and $R^6$ are each as defined above, n is 1 and X is $S(=O)_2$.

The compounds of the above-specified formulae IV, V, $R^5$—N=C=O, $R^5$—N=C=S, $R^{26}$—N=C=O, $R^{26}$—N=C=S, $R^5$—C(=O)-LG, $R^{26}$—C(=O)-LG, $R^5$—O—C (=O)-LG, $R^{26}$—O—C(=O)-LG, $R^5$—S(=O)$_2$-LG, $R^{26}$—S(=O)$_2$-LG, $R^5$-LG and $R^{26}$-LG may in each case be available on the market and may also be prepared by customary processes known to those skilled in the art.

The above-described reactions may each be carried out under the customary conditions familiar to those skilled in the art, for example with regard to pressure or sequence of addition of the components. Optionally, the process regime which is optimal under the particular conditions can be determined by the person skilled in the art by simple preliminary experiments. The intermediates and end products obtained by the above-described reactions may in each case, if desired and/or necessary, be purified and/or isolated by customary methods known to those skilled in the art. Suitable purification processes are, for example, extraction processes and chromatographic processes such as column chromatography or preparative chromatography. All of the aforementioned process steps, and in each case also the purification and/or isolation of intermediates or end products, can be performed partly or completely under an inert gas atmosphere, preferably under a nitrogen atmosphere.

The inventive substituted benzofused cycloheptanone derivatives of the aforementioned general formulae I, Ia Ib, Ic, Id, Ie, If, Ig, Ih and Ik, referred to hereinafter only as benzofused cycloheptanone derivatives of the general formula I, and corresponding stereoisomers, may be obtained in the form of their free bases, of their free acids or else in the form of corresponding salts, especially physiologically compatible salts. The free bases of the particular inventive substituted benzofused cycloheptanone derivatives of the aforementioned general formula I and corresponding stereoisomers may, for example, be converted to the corresponding salts, preferably physiologically compatible salts, by reaction with an inorganic or organic acid, preferably with hydrochloric acid, hydrobromic acid, sulfuric acid, phosphoric acid, methanesulfonic acid, p-toluenesulfonic acid, carbonic acid, formic acid, acetic acid, oxalic acid, succinic acid, tartaric acid, mandelic acid, fumaric acid, lactic acid, citric acid, glutamic acid or aspartic acid. The free bases of the particular benzofused cycloheptanone derivatives of the aforementioned general formula I and corresponding stereoisomers can likewise be converted to the corresponding physiologically compatible salts with the free acid or a salt of a sugar substitute, for example saccharin, cyclamate or acesulfame.

Accordingly, the free acids of the substituted benzofused cycloheptanone derivatives of the aforementioned general formula I and corresponding stereoisomers can be converted to the corresponding physiologically compatible salts by reaction with a suitable base. Examples include the alkali metal salts, alkaline earth metal salts or ammonium salts $[NH_xR_{4-x}]^+$ in which x=0, 1, 2, 3 or 4 and R is a linear or branched $C_{1-4}$-alkyl radical.

The inventive substituted benzofused cycloheptanone derivatives of the aforementioned general formula I and corresponding stereoisomers may optionally, just like the corresponding acids, the corresponding bases or salts of these compounds, also be obtained in the form of their solvates, preferably in the form of their hydrates, by customary methods known to those skilled in the art.

When the inventive substituted benzofused cycloheptanone derivatives of the aforementioned general formula I, after they have been prepared, are obtained in the form of a mixture of their stereoisomers, preferably in the form of their racemates or other mixtures of their different enantiomers and/or diastereomers, they can be separated and optionally isolated by customary processes known to those skilled in the art. Examples include chromatographic separation processes, especially liquid chromatography processes under standard pressure or under elevated pressure, preferably MPLC and HPLC processes, and processes for fractional crystallization. It is possible especially to separate individual enantiomers from one another, for example by means of HPLC on a chiral stationary phase, or, by means of crystallization with diastereomeric salts formed with chiral acids, for instance (+)-tartaric acid, (−)-tartaric acid or (+)-10-camphorsulfonic acid.

The inventive substituted benzofused cycloheptanone derivatives of the aforementioned general formula I and corresponding stereoisomers, and also in each case the corresponding acids, bases, salts and solvates, are toxicologically safe and are therefore suitable as active pharmaceutical ingredients in medicaments. The present invention therefore further provides a medicament comprising at least one substituted benzofused cycloheptanone derivative of the above-specified general formula I, in each case optionally in the form of its pure stereoisomers, especially enantiomers or diastereomers, of its racemates or in the form of a mixture of stereoisomers, especially of the enantiomers and/or diastereomers, in any mixing ratio, or in each case in the form of a corresponding salt, or in each case in the form of a corresponding solvate, and optionally one or more pharmaceutically compatible assistants.

These inventive medicaments are suitable especially for vanilloid receptor 1 (VR1/TRPV1) regulation, especially for vanilloid receptor 1 (VR1/TRPV1) inhibition and/or for vanilloid receptor 1 (VR1/TRPV1) stimulation. In addition, the inventive medicaments are suitable for CB1 receptor regulation and/or for CB2 receptor regulation.

The inventive medicaments are likewise suitable with preference for prophylaxis and/or treatment of disorders or diseases which are mediated at least partly by vanilloid receptors 1, CB1 receptors and/or CB2 receptors.

The inventive medicament is suitable with preference for treatment and/or prophylaxis of one or more disorders selected from the group consisting of pain, preferably of pain selected from the group consisting of acute pain, chronic pain, neuropathic pain and visceral pain; joint pain; migraine; depression; neuropathy; neural injuries; neurodegenerative disorders, preferably selected from the group consisting of multiple sclerosis, Alzheimer's disease, Parkinson's disease and Huntington's disease; cognitive dysfunctions, preferably cognitive deficiencies, more preferably memory impairments; epilepsy; respiratory pathway disorders, preferably selected from the group consisting of asthma and lung inflammation; coughing; urine incontinence; an overactive bladder (OAB); stomach ulcers; irritable bowel syndrome; stroke; eye irritations; skin irritations; neurotic skin disorders; inflammation disorders, preferably inflammation of the intestine; diarrhea; pruritus; disorders of food uptake, preferably selected from the group consisting of bulimia, cachexia, anorexia and obesity; medicament dependence; medicament abuse; withdrawal symptoms in the case of medicament dependence; evolution of tolerance to medicaments, preferably to natural or synthetic opioids; drug dependence; drug abuse; withdrawal symptoms in the case of drug dependence; alcohol dependence; alcohol abuse and withdrawal symptoms in the case of alcohol dependence; for diuresis; for antinatriuresis; to influence the cardiovascular system; to enhance vigilance; to enhance libido; to modulate movement activity; for anxiolysis; for local anesthesia and/or to inhibit undesired side effects, preferably selected from the group consisting of hyperthermia, hypertension and narrowing of thebronchia, triggered by the administration of vanilloid receptor 1 (VR1/TRPV1 receptors) agonists, preferably selected from the group consisting of capsaicin, resiniferatoxin, olvanil, arvanil, SDZ-249665, SDZ-249482, nuvanil and capsavanil.

The inventive medicament is particularly suitable for treatment and/or prophylaxis of one or more disorders selected from the group consisting of pain, preferably from pain selected from the group consisting of acute pain, chronic pain, neuropathic pain and visceral pain; migraine; depression; neurodegenerative disorders, preferably selected from the group consisting of multiple sclerosis, Alzheimer's disease, Parkinson's disease and Huntington's disease; cognitive dysfunctions, preferably cognitive deficiencies, more preferably memory impairments; urine incontinence; an overactive bladder (OAB); medicament dependence, medicament abuse; withdrawal symptoms in the case of medicament dependence; evolution of tolerance to medicaments, preferably evolution of tolerance to natural or synthetic opioids; drug dependence; drug abuse; withdrawal symptoms in the case of drug dependence; alcohol dependence; alcohol abuse and withdrawal symptoms in the case of alcohol dependence.

The inventive medicament is very particularly suitable for treatment and/or prophylaxis of pain, preferably of pain selected from the group consisting of acute pain, chronic pain, neuropathic pain and visceral pain, and/or urine incontinence.

The present invention further provides for the use of at least one substituted benzofused cycloheptanone derivative and optionally of one or more pharmaceutically compatible assistants for producing a medicament for vanilloid receptor 1 (VR1/TRPV1) regulation, preferably for vanilloid receptor 1 (VR1/TRPV1) inhibition and/or for vanilloid receptor 1 (VR1/TRPV1) stimulation, for CB1 receptor regulation and/or for CB2 receptor regulation.

Preference is given to the use of at least one substituted benzofused cycloheptanone derivative and optionally of one or more pharmaceutically compatible assistants for producing a medicament for prophylaxis and/or treatment of disorders or diseases which are mediated at least partly by vanilloid receptors 1, CB1 receptors and/or CB2 receptors.

Particular preference is given to the use of at least one substituted benzofused cycloheptanone derivative and optionally of one or more pharmaceutically compatible assistants for producing a medicament for treatment and/or prophylaxis of one or more disorders selected from the group consisting of pain, preferably of pain selected from the group consisting of acute pain, chronic pain, neuropathic pain and visceral pain; joint pain; migraine; depression; neuropathy; neural injuries; neurodegenerative disorders, preferably selected from the group consisting of multiple sclerosis, Alzheimer's disease, Parkinson's disease and Huntington's disease; cognitive dysfunctions, preferably cognitive deficiencies, more preferably memory impairments; epilepsy; respiratory pathway disorders, preferably selected from the group consisting of asthma and lung inflammation; coughing; urine incontinence; an overactive bladder (OAB); stomach ulcers; irritable bowel syndrome; stroke; eye irritations; skin irritations; neurotic skin disorders; inflammation disorders, preferably inflammation of the intestine; diarrhea; pruritus; disorders of food uptake, preferably selected from the group consisting of bulimia, cachexia, anorexia and obesity; medicament dependence; medicament abuse; withdrawal symptoms in the case of medicament dependence; evolution of tolerance to medicaments, preferably to natural or synthetic opioids; drug dependence; drug abuse; withdrawal symptoms in the case of drug dependence; alcohol dependence; alcohol abuse and withdrawal symptoms in the case of alcohol independence; for diuresis; for antinatriuresis; to influence the cardiovascular system; to enhance vigilance; to enhance libido; to modulate movement activity; for anxiolysis; for local anesthesia and/or to inhibit undesired side effects, preferably selected from the group consisting of hyperthermia, hypertension and narrowing of the bronchia, triggered by the administration of vanilloid receptor 1 (VR1/TRPV1 receptors) agonists, preferably selected from the group consisting of capsaicin, resiniferatoxin, olvanil, arvanil, SDZ-249665, SDZ-249482, nuvanil and capsavanil.

Very particular preference is given to the use of at least one substituted benzofused cycloheptanone derivative and optionally of one or more pharmaceutically compatible assistants for producing a medicament for treatment and/or prophylaxis of one or more disorders selected from the group consisting of pain, preferably from pain selected from the group consisting of acute pain, chronic pain, neuropathic pain and visceral pain; migraine; depression; neurodegenerative disorders, preferably selected from the group consisting of multiple sclerosis, Alzheimer's disease, Parkinson's disease and Huntington's disease; cognitive dysfunctions, preferably cognitive deficiencies, more preferably memory impairments; urine incontinence; an overactive bladder (OAB); medicament dependence; medicament abuse; withdrawal symptoms in the case of medicament dependence; evolution of tolerance to medicaments, preferably evolution of tolerance to natural or synthetic opioids; drug dependence; drug abuse; withdrawal symptoms in the case of drug dependence; alcohol dependence; alcohol abuse and withdrawal symptoms in the case of alcohol dependence.

Ever more preferred is the use of at least one substituted benzofused cycloheptanone derivative and optionally of one or more pharmaceutically compatible assistants for producing a medicament for treatment and/or prophylaxis of pain, preferably selected from the group consisting of acute pain, chronic pain, neuropathic pain and visceral pain, and/or urine incontinence.

The inventive medicament is suitable for administration to adults and children, including infants and babies. The inventive medicament may be present as a liquid, semisolid or solid medicament form, for example in the form of injection solutions, drops, juices, syrups, sprays, suspensions, tablets, patches, capsules, plasters, suppositories, ointments, creams, lotions, gels, emulsions, aerosols or in multiparticulate form, for example in the form of pellets or granules, optionally compressed to tablets, filled into capsules or suspended in a liquid, and may also be administered as such.

In addition to at least one substituted benzofused cycloheptanone derivative of the above-specified general formula I, optionally in the form of its pure stereoisomers, especially enantiomers or diastereomers, of its racemates or in the form of mixtures of the stereoisomers, especially of the enantiomers or diastereomers, in any mixing ratio, or optionally in the form of a corresponding salt or in each case in the form of a corresponding solvate, the inventive medicament typically comprises further physiologically compatible pharmaceutical assistants which may, for example, be selected from the group consisting of carrier materials, fillers, solvents, diluents, surfactants, dyes, preservatives, disintegrants, lubricants, aromas and binders.

The selection of the physiologically compatible assistants and the amounts thereof to be used depends upon whether the medicament is to be administered orally, subcutaneously, parenterally, intravenously, intraperitoneally, intradermally, intramuscularly, intranasally, buccally, rectally or locally, for example to infections on the skin, the mucous membranes and in the eyes. For oral application, suitable formulations are preferably those in the form of tablets, coated tablets, capsules, granules, pellets, drops, juices and syrups; suitable formulations for parenteral, topical and inhalative application are preferably solutions, suspensions, readily reconstitutable dry formulations and sprays. The inventive substituted benzofused cycloheptanone derivatives used in the inventive medicament may, in a depot, in dissolved form or in a plaster, optionally with addition of skin penetration-promoting agents, are suitable percutaneous administration formulations. Orally or percutaneously applicable formulation forms may also release the particular inventive substituted benzofused cyclohexanone derivative in a retarded manner.

The inventive medicaments are produced with the aid of conventional means, apparatus, methods and processes known from the prior art, as described, for example, in "Remington's Pharmaceutical Sciences", editor A. R. Gennaro, 17th edition, Mack Publishing Company, Easton, Pa., 1985, more particularly in part 8, chapter 76 to 93. The corresponding description is hereby included as a reference and forms part of the disclosure. The amount of the particular inventive benzofused cycloheptanone derivatives of the above-specified general formula I to be administered to the patient may vary and is, for example, dependent on the weight or age of the patient and on the administration method, the indication and the severity of the disorder. Typically, from 0.001 to 100 mg/kg, preferably from 0.05 to 75 mg/kg, more preferably from 0.05 to 50 mg/kg, of body weight of the patient of at least one such inventive compound are administered.

Pharmacological Methods:

I. Functional Study on the Vanilloid Receptor 1 (VR1/TRPV1 Receptor)

The agonistic or antagonistic action of the substances to be studied on the vanilloid receptor 1 (VR1/TRPV1) of the rat species can be determined with the following assay. In this assay, the $Ca^{2+}$ current through the receptor channel is quantified with the aid of a $Ca^{2+}$-sensitive dye (Fluo-4 type, Molecular Probes Europe BV, Leiden the Netherlands) in a fluorescent imaging plate reader (FLIPR, Molecular Devices, Sunnyvale, USA).

Method:

Complete medium: 50 ml HAMS F12 Nutrient Mixture (Gibco Invitrogen GmbH, Karlsruhe, Germany) with 10% by volume of FCS (fetal calf serum, Gibco Invitrogen GmbH, Karlsruhe, Germany, heat-inactivated);

2 mM L-glutamine (Sigma, Munich, Germany);

1% by weight of AA solution (antibiotic/antimycotic solution, PAA, Pasching, Austria) and 25 ng/ml of NGF medium (2.5 S, Gibco Invitrogen GmbH, Karlsruhe, Germany)

Cell culture plate: poly-D-lysine-coated, black 96-hole plates with a clear bottom (96 well black/clear plate, BD Biosciences, Heidelberg, Germany) are additionally coated with laminin (Gibco Invitrogen GmbH, Karlsruhe, Germany) by diluting laminin to a concentration of 100 µg/ml with PBS (Ca—Mg-free PBS, Gibco Invitrogen GmbH, Karlsruhe, Germany). Aliquots having a concentration of 100 µg/ml of laminin are withdrawn and stored at −20° C. The aliquots are diluted with PBS in a ratio of 1:10 to 10 µg/ml of laminin and in each case 50 µl of the solution are pipetted into a well of the cell culture plate. The cell culture plates are incubated at 37° C. for at least two hours, the supernatant solution is removed by suction and the wells are each washed twice with PBS. The coated cell culture plates are stored with supernatant PBS which is not removed until directly before the application of the cells.

Preparation of the Cells:

The spinal column is removed from beheaded rats and placed directly into cold HBSS buffer (Hank's buffered saline solution, Gibco Invitrogen GmbH, Karlsruhe, Germany), i.e. placed in an ice bath, which has been admixed with 1% by volume of an AA solution (antibiotic/antimycotic solution, PAA, Pasching, Austria). The spinal column is severed longitudinally and removed from the spinal canal together with fasciae. Subsequently, the dorsal root ganglia (DRGs) are removed and in turn stored in cold HBSS buffer admixed with 1% by volume of an AA solution. The DRGs freed completely of blood residues and spinal nerves are in each case transferred to 500 µl of cold type 2 collagenase (PAA, Pasching, Austria) and incubated at 37° C. for 35 minutes. After addition of 2.5% by volume of trypsin (PAA, Pasching, Austria), incubation is continued at 37° C. for a further 10 minutes. After complete incubation, the enzyme solution is cautiously pipetted off and the remaining DRGs are each admixed with 500 µl of complete medium.

The DRGs are each suspended repeatedly, drawn through cannulas No. 1, No. 12 and No. 16 by means of a syringe and transferred to 50 ml Falcon tubes which are made up to 15 ml with complete medium. The contents of each Falcon tube are in each case filtered through a 70 µm Falcon filter insert and centrifuged at 1200 revolutions and room temperature for 10 minutes. The resulting pellet is in each case taken up in 250 µl of complete medium and the cell count is determined.

The number of cells in the suspension is adjusted to 3 times $10^5$ per ml and in each case 150 µl of this suspension are added to one well of the cell culture plates coated as described above. In the incubator, the plates are left to stand at 37° C., 5% by volume of $CO_2$ and 95% relative air humidity for two to three days.

Subsequently, the cells are laden with 2 µM Fluo-4 and 0.01% by volume of Pluronic F127 (Molecular Probes Europe BV, Leiden, the Netherlands) in HBSS buffer (Hank's buffered saline solution, Gibco Invitrogen GmbH, Karlsruhe, Germany) at 37° C. for 30 min, washed 3× with HBSS buffer and, after a further incubation of 15 minutes, used in the FLIPR assay at room temperature for $Ca^{2+}$ measurement. The $Ca^{2+}$-dependent fluorescence is measured beforehand after addition of substances ($\lambda_{ex}$=488 nm, $\lambda_{em}$=540 nm). The quantification is effected by the measurement of the highest fluorescence intensity (FC, fluorescence counts) over the time.

FLIPR Assay:

The FLIPR protocol consists of 2 substance additions. First, the compounds to be tested (10 µM) are pipetted onto the cells and the $Ca^{2+}$ current is compared with the control (capsaicin 10 µM). This gives rise to the result in % activation based on the $Ca^{2+}$ signal after addition of 10 µM capsaicin (CP). After incubation for 5 minutes, 100 nM capsaicin is applied and the current of $Ca^{2+}$ is likewise determined.

Desensitizing agonists and antagonists lead to a suppression in the $Ca^{2+}$ current. % inhibition is calculated compared to the maximum achievable inhibition with 10 µM capsaicin.

Triple determinations (n=3) are performed and they are repeated in at least 3 independent experiments (N=4).

II. Functional Studies on the Vanilloid Receptor (VR1)

The agonistic or antagonistic action of the substances to be tested on vanilloid receptor (VR1) can also be determined with the assay which follows. In this assay, the $Ca^{2+}$ current through the channel is quantified with the aid of a $Ca^{2+}$-sensitive dye (Fluo-4 type, Molecular Probes, Europe BV, Leiden, the Netherlands) in a fluorescent imaging plate reader (FLIPR, Molecular Devices, Sunnyvale, USA).

Method:

Chinese hamster ovary cells (CHO K1 cells, European Collection of Cell Cultures (ECACC) Great Britain) are transfected stably with the VR1 gene. For functional studies, these cells are plated out onto poly-D-lysine-coated black 96-well plates with a clear bottom (BD Biosciences, Heidelberg, Germany) in a density of 25 000 cells/well. The cells are incubated overnight at 37° C. and 5% $CO_2$ in a culture medium (Ham's Nutrient Mixture F12, 10% by volume of FCS (fetal calf serum), 18 µg/ml of L-proline). The next day, the cells are incubated with Fluo-4 (Fluo-4 2 µM, Pluronic F127 0.01% by volume, Molecular Probes in HBSS (Hank's buffered saline solution), Gibco Invitrogen GmbH, Karlsruhe, Germany) at 37° C. for 30 minutes. Subsequently, the plates are washed 3 times with HBSS buffer and, after a further incubation of 15 minutes at room temperature, used for $Ca^{2+}$ measurement in FLIPR. The $Ca^{2+}$-dependent fluorescence is measured before and after addition of the substances to be studied (wavelength $\lambda_{ex}$=488 nm, $\lambda_{em}$=540 nm). The quantification is effected by measuring the highest fluorescence intensity (FC, fluorescence counts) over the time.

FLIPR Assay:

The FLIPR protocol consists of 2 substance additions. First, the substances to be tested (10 µM) are pipetted onto the cells and the $Ca^{2+}$ current is compared with the control (capsaicin 10 µM) (% activation based on the $Ca^{2+}$ signal after addition of 10 µM capsaicin). After incubation for 5 minutes, 100 nM capsaicin is applied and the current of $Ca^{2+}$ is likewise determined.

Desensitizing agonists and antagonists led to a suppression of the $Ca^{2+}$ current. % inhibition is calculated compared to the maximum achievable inhibition with 10 µM capsazepine.

III. Formalin Test on Mice

The test to determine the antinociceptive action of the inventive compounds is carried out in the formalin test on male mice (NMRI, body weight from 20 to 30 g, Iffa, Credo, Belgium).

In the formalin test, according to D. Dubuisson et al., Pain 1977, 4, 161-174, a distinction is drawn between the first (early) phase (from 0 to 15 minutes after the formalin injection) and the second (late) phase (from 15 to 60 minutes after the formalin injection). The early phase, as a direct reaction to the formalin injection, constitutes a model for acute pain, while the late phase is considered to be a model for persistent (chronic) pain (T. J. Coderre et al., Pain 1993, 52, 259-285). The corresponding literature descriptions are hereby included as a reference and form part of the disclosure.

The inventive compounds are tested in the second phase of the formalin test in order to obtain statements regarding substance effects on chronic/inflammatory pain.

According to the administration type of the inventive compounds, the administration time of the inventive compounds before the formalin injection is selected. The intravenous administration of 10 mg/kg of body weight of the test substances is effected 5 minutes before the formalin injection. This is done by a single subcutaneous formalin injection (20 µl, 1% aqueous solution) into the dorsal side of the right hind paw, such that a nociceptive reaction is induced in freely mobile test animals, which is manifested in obvious licking and biting of the paw affected.

Subsequently, for a test period of three minutes in the second (late) phase of the formalin test (from 21 to 24 minutes after the formalin injection), the nociceptive behavior is registered continuously by observing the animals. The pain behavior is quantified by summation of the seconds in which the animals exhibit licking and biting of the paw affected within the test period.

The comparison is in each case with control animals which, instead of the inventive compounds, receive vehicle (0.9% aqueous sodium chloride solution) before formalin administration. Based on the quantification of the pain behavior, the substance action in the formalin test is determined as the change relative to the corresponding control in percent.

After injection of substances which have antinociceptive activity in the formalin test, the behavior of the animals described, i.e. licking and biting, is reduced or eliminated.

IV. Test for Analgesic Activity in the Writhing Test

The test of the inventive compounds of the general formula I for analgesic activity was carried out in phenylquinone-induced writhing in mice, modified according to I. C. Hendershot and J. Forsaith (1959), J. Pharmacol. Exp. Ther. 125, 237-240. The corresponding literature description is hereby included as a reference and forms part of the disclosure.

To this end, male NMRI mice with a weight of from 25 to 30 g were used. Groups of 10 animals per compound dose received, 10 minutes after intravenous administration of the compounds to be tested, 0.3 ml/mouse of a 0.02% aqueous solution of phenylquinone (phenylbenzoquinone, from Sigma, Deisenhofen, Germany; preparation of the solution with addition of 5% by weight of ethanol and storage in a water bath at 45° C.) which was applied intraperitoneally. The animals were placed individually into observation cages. With the aid of a push-button counter, the number of pain-induced stretching motions (so-called writhing reactions=arching of the back with stretching-out of the rear extremities) was counted for from 5 to 20 minutes after the phenylquinone administration. The control employed was animals which had received only physiological saline. All compounds were tested in the standard dosage of 10 mg/kg.

V. Functional Study on the Human CB1 Receptor

Incubation and Washing Buffer:

50 mM TRIS (from Fluka, Cat. No. 93349); 2.5 mM EDTA (from Fluka Cat. No. 03680); 5 mM $MgCl_2$ (from Merck, Cat. No. 1.05833); 0.5 mg/ml BSA (from Sigma Cat. No. A-2153)

The pH of the buffer is adjusted to 7.4 at 4° C.

Medium for Softening the Filter Mats:

0.05% PEI (from Sigma, Cat. No. P-3143)

The membranes (RBHCB1M, from Perkin Elmer (human recombinant cell membranes)) were supplied in aliquots of 1 ml each in dry ice and stored at −80° C. The protein concentration of the batches was around 6 mg/ml. For the test, in each case 1 ml was thawed rapidly and diluted with 7 ml of incubation buffer (1:8). 20 µl of this dilution were used in the test. This corresponded to a protein content of approx. 15 µg in the batch.

Incubation Batch:

MTP from Costar® of the "U type" (assay MTP; Cat. No. 3794) was used. The pipetting sequence is reproduced in Table 1 below.

TABLE 1

| Substance | Molarity in the batch | µl | Protein in the batch |
|---|---|---|---|
| Incubatation buffer | — | 200 | — |
| Test substance or USB* | $10^{-5}$M | 5 | — |

TABLE 1-continued

| Substance | Molarity in the batch | μl | Protein in the batch |
|---|---|---|---|
| Membrane | — | 20 | approx. 15 μg |
| [³H]CP55,940 | 1 nM | 25 | — |

*USB (unspecific binding): WIN 55,212-mesylate (from Tocris, Cat. No. 1038) (10⁻⁶M in the batch)
[³H] CP-55,940 (from Perkin Elmer Cat. No. 1051)

After the pipetting operation had ended, a lid was placed on the MTP and the incubation was effected at 25° C. for 90 min.

Subsequently, the samples were removed by suction with the aid of a Brandel cell harvester (model MPXRI-96T) through a GF/B Unifilter MTP (from Packard, Cat. No. 6005177) presoftened with 0.05% PEI. The samples were washed twice with 200 ml of ice-cooled incubation buffer per 96-well MTP. Thereafter, the plate was dried in a drying cabinet +60° C. for 1 h. Subsequently, the bottom side of the MTP was sealed from the bottom exactly with a "back seal" from Packard. 35 μl of scintillator (Packard, "Ultima Gold"; Cat. No. 6013151) per well were pipetted thereto. In addition, the top side of the plate was now sealed with a "top seal" (from Packard; Cat. No. 6005185). After a wait time of 1 h, the plate was analyzed on a "Trilux" from Wallac.

VI. Determination of the Affinity for the Cannabinoid Receptor CB2 (CB2 Receptor):

To determine the affinity of the inventive compounds for the cannabinoid receptor, membranes from human recombinant HEK-293EBNA cells were used, which had been transfected stably with the human CB2 receptor. The radioligand used was tritium-labeled 5-(1,1-dimethylheptyl)-2-(5-hydroxypropyl)cyclohexyl)-1-alpha,2-beta,5-alpha)phenol ([3]H—CP 55,940 with 103.4 Ci/mmol, 1 mCi/ml). The determination was effected in a test buffer composed of 50 mM Tris-HCl, 2.5 mM EDTA, 5 mM MgCl$_2$ and 1.0 mg/ml of fatty acid-free BSA. The test substances were each dissolved in DMSO.

The affinity of the inventive compounds for the CB2 receptor is determined by their ability to displace [3]H—CP 55,940 from CB2 receptors in membranes from HEK-293EBNA cells. To this end, in each case 8 μg of the membranes (20 μl of a solution from membranes in a concentration of 400 μg/ml) are incubated in wells on a microtiter plate with a 0.33 nM solution of [³]H-CP 55,949 (120 Ci/mmol) in a total volume of test buffer of 200 μl at 30° C. for 90 minutes.

Subsequently, either the test substances or WIN 55212-2 to determine the unspecific binding, in each case dissolved in DMSO, are added to the wells so as to result in each case in a concentration of the corresponding substances of 10 μM.

Incubation at 30° C. is continued for a further 40 minutes. The binding reaction was ended by rapid filtration through GF/C filter paper which had been treated with 0.05% PEI using a Brandel cell harvester with 96 wells. The filters are washed nine times with 0.5 ml of ice-cooled washing buffer (50 nM Tris-HCl, 5 mM MgCl$_2$, 2.5 mM EDTA, 2% BSA, pH 7.4), air-dried and placed in scintillation fluid, and the radioactivity is determined with the aid of a scintillation counter.

The percentage displacement of the radioactive ligand [³]H-CP 55,940 from its binding to the CB2 receptor is reported as percent inhibition of the specific binding.

The invention will be illustrated hereinafter with reference to examples. These illustrations are merely by way of example and do not restrict the general concept of the invention.

EXAMPLES

The yields of the compounds prepared are not optimized. All temperatures are uncorrected.

The chemicals and solvents used were purchased commercially from the conventional suppliers (Acros, Avocado, Aldrich, Bachem, Fluka, Lancaster, Maybridge, Merck, Sigma, TCI, etc.) or synthesized by methods known to those skilled in the art.

The stationary phase used for the column chromatography was silica gel 60 (0.040-0.063 mm) from E. Merck, Darmstadt.

The thin layer chromatography analyses were carried out with ready-to-use HPTLC plates, silica gel 60 F 254, from E. Merck, Darmstadt.

The mixing ratios of solvents, eluents or for chromatographic analyses are always reported in volume/volume.

The analysis was effected by mass spectroscopy and NMR.

4-Hydroxymethyl-3,4-dihydro-2H-benzo[b]thiepin-5-one and 4,4-bis(hydroxymethyl)-3,4-dihydro-2H-benzo[b]thiepin-5-one To a solution of 3,4-dihydro-2H-benzo[b]thiepin-5-one (16.5 g; 92.6 mmol) in 275 ml of tetrahydrofuran were added, at room temperature, potassium carbonate (1.37 g) and formalin solution (55 ml; 36% solution in water). The reaction mixture was stirred at 40° C. for 7 days. The mixture was then diluted with 300 ml of water, and the phases were separated and extracted with ethyl acetate. The crude product was purified by column chromatography on silica gel (eluent: 9:1 hexane/ethyl acetate and 4:1 hexane/ethylacetate). This afforded 4-hydroxymethyl-3,4-dihydro-2H-benzo[b]thiepin-5-one (colorless oil; 5.1 g; 26.5%) and 4,4-bis(hydroxymethyl)-3,4-dihydro-2H-benzo[b]thiepin-5-one (colorless solid; 8.7 g; 39%).

6,6-Bis(hydroxymethyl)-6,7,8,9-tetrahydrobenzocyclohepten-5-one

To a solution of 6,7,8,9-tetrahydrobenzocyclohepten-5-one (50 g, 312 mmol) in 875 ml of tetrahydrofuran were added, at room temperature, potassium carbonate (4.4 g) and formalin solution (175 ml; 36% solution in water). The reaction mixture was stirred at 40° C. for 32 hours. The mixture was then diluted with 900 ml of water, and the phases were separated and extracted with ethyl acetate. The crude product was purified by column chromatography on silica gel (eluent: 9:1 hexane/ethyl acetate and 1:1 hexane/ethyl acetate). This gave 6,6-bis(hydroxymethyl)-6,7,8,9-tetrahydrobenzocyclohepten-5-one (colorless oil; 61.3 g; 89%).

4,4-Bis(hydroxymethyl)-3,4-dihydro-2H-benzo[b]oxepin-5-one

To a solution of 3,4-dihydro-2H-benzo[b]oxepin-5-one (12.0 g; 74 mmol) in 215 ml of tetrahydrofuran were added, at room temperature, potassium carbonate (1.01 g) and formalin solution (44 ml; 36% solution in water). The reaction mixture was stirred at 40° C. for 2 days. The mixture was then diluted with 250 ml of water, and the phases were separated and extracted with ethyl acetate. The crude product was purified by column chromatography on silica gel (eluent: 1:1 hexane/ethyl acetate and ethyl acetate). This gave 4,4-bis(hydroxymethyl)-3,4-dihydro-2H-benzo[b]oxepin-5-one (colorless crystals; 13.1 g; 80%).

Example Compound 1

Pentylcarbamic acid 5-oxo-2,3,4,5-tetrahydrobenzo[b]thiepin-4-ylmethyl ester

To a solution of 4-hydroxymethyl-3,4-dihydro-2H-benzo[b]thiepin-5-one (264 mg, 1.27 mmol) in 16 ml of tetrahydrofuran were added, at 0° C., triethylamine (0.2 ml, 1.4 mmol) and n-pentyl isocyanate (492 µl, 4.9 mmol). The mixture was heated under reflux for 15 hours, concentrated and purified by column chromatography on silica gel (eluent: 4:1 diisopropyl ether/hexane). The product was obtained in a yield of 145 mg (35%).

Example Compound 2

Phenylcarbamic acid 4-(phenylcarbamoyloxymethyl)-5-oxo-2,3,4,5-tetrahydro-benzo[b]thiepin-4-ylmethyl ester To a solution of 4,4-bis(hydroxymethyl)-3,4-dihydro-2H-benzo[b]thiepin-5-one (395 mg, 1.66 mmol) in 21 ml of tetrahydrofuran were added, at 0° C., triethylamine (0.25 ml, 1.8 mmol) and phenyl isocyanate (395 µl, 3.66 mmol). The mixture was stirred at room temperature for 24 hours, concentrated and purified by column chromatography on silica gel (eluent: dichloromethane). The product was obtained in a yield of 665 mg (84%).

Example Compound 3

Phenylcarbamic acid 5-oxo-2,3,4,5-tetrahydrobenzo[b]thiepin-4-ylmethyl ester

To a solution of 4-hydroxymethyl-3,4-dihydro-2H-benzo[b]thiepin-5-one (359 mg, 1.726 mmol) in 22 ml of tetrahydrofuran were added, at 0° C., triethylamine (0.26 ml, 1.9 mmol) and phenyl isocyanate (410 µl, 3.8 mmol). The mixture was stirred at room temperature for 2 hours, concentrated and purified by column chromatography on silica gel (eluent: 1:2 tert-butyl methyl ether/cyclohexane). The product was obtained in a yield of 350 mg (62%).

Example Compound 4

(3-Trifluoromethylphenyl)carbamic acid 5-oxo-2,3,4,5-tetrahydro-benzo[b]thiepin-4-ylmethyl ester To a solution of 4-hydroxymethyl-3,4-dihydro-2H-benzo[b]thiepin-5-one (256 mg, 1.23 mmol) in 15 ml of tetrahydrofuran were added, at room temperature, triethylamine (0.19 ml, 1.4 mmol) and α,α,α-trifluoro-m-tolyl isocyanate (345 µl, 2.46 mmol). The mixture was stirred at room temperature for 2 hours, concentrated and purified by column chromatography on silica gel (eluent: 1:2 tert-butyl methyl ether/cyclohexane). The product was obtained in a yield of 180 mg (37%).

Example Compound 5

(4-Bromophenyl)carbamic acid 5-oxo-2,3,4,5-tetrahydrobenzo[b]thiepin-4-ylmethyl ester To a solution of 4-hydroxymethyl-3,4-dihydro-2H-benzo[b]thiepin-5-one (224 mg, 1.08 mmol) in 14 ml of tetrahydrofuran were added, at room temperature, triethylamine (0.16 ml, 1.18 mmol) and 4-bromophenyl isocyanate (0.423 g, 2.15 mmol). The mixture was stirred at room temperature for 2 hours, concentrated and purified by column chromatography on silica gel (eluent: 1:2 tert-butyl methyl ether/cyclohexane). The product was obtained in a yield of 250 mg (57%).

Example Compound 6

Cyclohexylcarbamic acid 4-hydroxymethyl-5-oxo-2,3,4,5-tetrahydro-benzo[b]thiepin-4-ylmethyl ester To a solution of 4,4-bis(hydroxymethyl)-3,4-dihydro-2H-benzo[b]thiepin-5-one (424 mg, 1.78 mmol) in 22 ml of tetrahydrofuran were added, at 0° C., triethylamine (0.27 ml, 1.96 mmol) and cyclohexyl isocyanate (1.0 ml, 7.84 mmol). The mixture was stirred at 80° C. for 18 hours, concentrated and purified by column chromatography on silica (eluent: 1:2 tert-butyl methyl ether/cyclohexane). The product was obtained in a yield of 366 mg (57%).

Example Compound 7

Cyclohexylcarbamic acid 5-oxo-2,3,4,5-tetrahydrobenzo[b]thiepin-4-ylmethyl ester To a solution of 4-hydroxymethyl-3,4-dihydro-2H-benzo[b]thiepin-5-one (283 mg, 1.36 mmol) in 17 ml of tetrahydrofuran were added, at room temperature, triethylamine (0.21 ml, 1.5 mmol) and cyclohexyl isocyanate (682 µl, 5.56 mmol). The mixture was stirred at 80° C. for 24 hours, concentrated and purified by column chromatography on silica gel (eluent: 1:2 tert-butyl methyl ether/cyclohexane). The product was obtained in a yield of 190 mg (42%).

Example Compound 8

Cyclohexylcarbamic acid 6-(cyclohexylcarbamoyloxymethyl)-5-oxo-6,7,8,9-tetrahydro-5H-benzocyclohepten-6-ylmethyl ester To a solution of 6,6-bis(hydroxymethyl)-6,7,8,9-tetrahydrobenzocyclohepten-5-one (455 mg, 2.07 mmol) in 26 ml of tetrahydrofuran were added, at room temperature, triethylamine (0.31 ml, 2.27 mmol) and cyclohexyl isocyanate (1.76 g, 14.35 mmol). The mixture was stirred at 80° C. for 24 hours, concentrated and purified by column chromatography on silica gel (eluent: 1:2 tert-butyl methyl ether/cyclohexane). The product was obtained in a yield of 130 mg (13%).

Example Compound 9

Phenylthiocarbamic acid O-(4-hydroxymethyl-5-oxo-2,3,4,5-tetrahydro-benzo[b]thiepin-4-ylmethyl) ester To a solution of 4,4-bis(hydroxymethyl)-3,4-dihydro-2H-benzo[b]thiepin-5-one (252 mg, 1.06 mmol) in 13 ml of tetrahydrofuran were added, at room temperature, triethylamine (0.16 ml, 1.16 mmol) and phenyl isothiocyanate (277 µl, 2.3 mmol). The mixture was stirred at 80° C. for 36 hours, concentrated and purified by column chromatography on silica gel (eluent: 4:1 diisopropyl ether/hexane). The product was obtained in a yield of 48 mg (12%).

Example Compound 10

N-(4-Methylphenylsulfonyl)carbamic acid 5-oxo-2,3,4,5-tetrahydro-benzo[b]thiepin-4-ylmethyl ester To a solution of 4-hydroxymethyl-3,4-dihydro-2H-benzo[b]thiepin-5-one (300 mg, 1.44 mmol) in 7 ml of tetrahydrofuran were added, at room temperature, triethylamine (0.22 ml, 1.6 mmol) and p-toluenesulfonyl isocyanate (312 mg, 1.586 mmol). The mixture was stirred at room temperature for 1.5 hours, concentrated and purified by column chromatography on silica gel (eluent: 1:9 tert.butyl methyl ether/dichloromethane). The product was obtained in a yield of 250 mg (43%).

Example Compound 11

Naphthalen-1-ylthiocarbamic acid O-(4-hydroxymethyl-5-oxo-2,3,4,5-tetrahydrobenzo[b]thiepin-4-ylmethyl)ester To a solution of 4,4-bis(hydroxymethyl)-3,4-dihydro-2H-benzo[b]thiepin-5-one (476 mg, 2.0 mmol) in 15 ml of tetrahydrofuran were added, at room temperature, triethylamine (0.31 ml, 2.2 mmol) and 1-naphthyl isothiocyanate (407 mg, 2.2 mmol). The mixture was heated to reflux for 24 hours, concentrated and purified by column chromatography on silica gel (eluent: 1:19 tert-butyl methyl ether/dichloromethane). The product was obtained in a yield of 87 mg (9%).

Example Compound 12

Pentylcarbamic acid 4-hydroxymethyl-5-oxo-2,3,4,5-tetrahydrobenzo[b]oxepin-4-ylmethyl ester To a solution of 4,4-bis(hydroxymethyl)-3,4-dihydro-2H-benzo[b]oxepin-5-one (260 mg, 1.17 mmol) in 15 ml of tetrahydrofuran were added, at room temperature, triethylamine (0.18 ml, 1.3 mmol) and n-pentyl isocyanate (332 µl, 2.57 mmol). The mixture was heated to reflux for 24 hours, concentrated and purified by column chromatography on silica gel (eluent: 1:2 ethyl acetate/hexane). The product was obtained in a yield of 210 mg (54%).

Example Compounds 13 and 14

Pentylcarbamic acid 4-hydroxymethyl-5-oxo-2,3,4,5-tetrahydrobenzo[b]thiepin-4-ylmethyl ester and pentylcarbamic acid 4-(pentylcarbamoyloxymethyl)-5-oxo-2,3,4,5-tetrahydrobenzo[b]thiepin-4-ylmethyl ester To a solution of 4,4-bis(hydroxymethyl)-3,4-dihydro-2H-benzo[b]thiepin-5-one (264 mg, 1.11 mmol) in 14 ml of tetrahydrofuran were added, at room temperature, triethylamine (0.17 ml, 1.2 mmol) and n-pentyl isocyanate (314 µl, 2.44 mmol). The mixture was heated to reflux for 30 hours, concentrated and purified by column chromatography on silica gel (eluent: 1:2 ethyl acetate/hexane). This afforded pentylcarbamic acid 4-hydroxymethyl-5-oxo-2,3,4,5-tetrahydrobenzo[b]thiepin-4-ylmethyl ester (Example 13) in a yield of 200 mg (51%) and pentylcarbamic acid 4-(pentylcarbamoyloxymethyl)-5-oxo-2,3,4,5-tetrahydrobenzo[b]thiepin-4-yl methyl ester (Example 14) in a yield of 188 mg (37%).

Example Compound 15

Phenylthiocarbamic acid O-(4-hydroxymethyl-5-oxo-2,3,4,5-tetrahydro-benzo[b]oxepin-4-ylmethyl)ester To a solution of 4,4-bis(hydroxymethyl)-3,4-dihydro-2H-benzo[b]oxepin-5-one (500 mg, 2.25 mmol) in 28 ml of tetrahydrofuran were added, at room temperature, triethylamine (0.34 ml, 2.5 mmol) and phenyl isothiocyanate (672 µl, 5.63 mmol). The mixture was heated to reflux for 72 hours, concentrated and purified by column chromatography on silica gel (eluent: 1:1 tert-butyl methyl ether/cyclohexane). The product was obtained in a yield of 149 mg (19%).

Example Compound 16

2,4-Difluorophenylcarbamic acid 4-(2,4-difluorophenylcarbamoyloxymethyl)-5-oxo-2,3,4,5-tetrahydrobenzo[b]oxepin-4-ylmethyl ester To a solution of 4,4-bis(hydroxymethyl)-3,4-dihydro-2H-benzo[b]oxepin-5-one (399 mg, 1.795 mmol) in 22 ml of tetrahydrofuran were added, at 0° C., triethylamine (0.27 ml, 1.98 mmol) and 2,4-difluorophenyl isocyanate (535 µl, 4.49 mmol). The mixture was stirred at room temperature for 18 hours, concentrated and purified by column chromatography on silica gel (eluent: 1:2 tert-butyl methyl ether/cyclohexane). The product was obtained in a yield of 110 mg (12%).

Example Compound 17

(3-Trifluoromethylphenyl)thiocarbamic acid O-(4-hydroxymethyl-5-oxo-2,3,4,5-tetrahydrobenzo[b]thiepin-4-ylmethyl)ester To a solution of 4,4-bis(hydroxymethyl)-3,4-dihydro-2H-benzo[b]thiepin-5-one (555 mg, 2.33 mmol) in 29 ml of tetrahydrofuran were added, at room temperature, triethylamine (0.35 ml, 2.56 mmol) and 3-(trifluoromethyl)phenyl isothiocyanate (885 µl, 5.82 mmol). The mixture was heated to reflux for 72 hours, concentrated and purified by column chromatography on silica gel (eluent: 1:2 ethyl acetate/hexane). The product was obtained in a yield of 320 mg (31%).

Example Compound 18

(3-Trifluoromethylphenyl)thiocarbamic acid O-(4-hydroxymethyl-5-oxo-2,3,4,5-tetrahydrobenzo[b]oxepin-4-ylmethyl)ester To a solution of 4,4-bis(hydroxymethyl)-3,4-dihydro-2H-benzo[b]oxepin-5-one (510 mg, 2.3 mmol) in 29 ml tetrahydrofuran were added, at room temperature, triethylamine (0.35 ml, 2.5 mmol) and 3-(trifluoromethyl)phenyl isothiocyanate (872 µl, 5.74 mmol). The mixture was heated to reflux for 72 hours, concentrated and purified by column chromatography on silica gel (eluent: 1:2 ethyl acetate/hexane). The product was obtained in a yield of 483 mg (50%).

Example Compound 19

Benzoylcarbamic acid 4-benzoylcarbamoyloxymethyl-5-oxo-2,3,4,5-tetrahydro-benzo[b]oxepin-4-ylmethyl ester To a solution of 4,4-bis(hydroxymethyl)-3,4-dihydro-2H-benzo[b]oxepin-5-one (400 mg, 1.8 mmol) in 22 ml of tetrahydrofuran were added, at room temperature, triethylamine (0.27 ml, 1.98 mmol) and benzoyl isothiocyanate (678 µl, 5.4 mmol). The mixture was stirred at room temperature for 7 days, concentrated and purified by column chromatography on silica gel (eluent: 1:1 ethyl acetate/hexane). The product was obtained in a yield of 393 mg (42%).

Example Compound 20

(2,4-Difluorophenyl)carbamic acid 4-hydroxymethyl-5-oxo-2,3,4,5-tetrahydro-benzo[b]thiepin-4-ylmethyl ester To a solution of 4,4-bis(hydroxymethyl-3,4-dihydro-2H-benzo[b]thiepin-5-one (100 mg, 0.42 mmol) in 5 ml of tetrahydrofuran was added, at room temperature, 2,4-difluorophenyl isocyanate (124 µl, 1.05 mmol). The mixture was stirred at room temperature for 72 hours, concentrated and purified by column chromatography on silica gel (eluent: 1:2 ethyl acetate/hexane). The product was obtained in a yield of 50 mg (30%).

Example Compound 21

(2,4-Difluorophenyl)thiocarbamic acid O-(4-hydroxymethyl-5-oxo-2,3,4,5-tetrahydrobenzo[b]thiepin-4-ylmethyl)ester To a solution of 4,4-bis(hydroxymethyl)-3,4-dihydro-2H-benzo[b]thiepin-5-one (720 mg, 3.02 mmol) in 38 ml of tetrahydrofuran were added, at room temperature, triethylamine (0.46 ml, 3.32 mmol) and 2,4-difluorophenyl isothiocyanate (985 µl, 7.55 mmol). The mixture was heated to reflux for 72 hours, concentrated and purified by column chromatography on silica gel (eluent: 1:2 ethyl acetate/hexane). The product was obtained in a yield of 170 mg (14%).

Example Compound 22

(3-Trifluoromethylphenyl)thiocarbamic acid O-(6-hydroxymethyl-5-oxo-6,7,8,9-tetrahydro-5H-benzocyclohepten-6-ylmethyl)ester To a solution of 6,6-bis(hydroxymethyl)-6,7,8,9-tetrahydrobenzocyclohepten-5-one (500 mg, 2.27 mmol) in 28 ml of tetrahydrofuran were added, at room temperature, triethylamine (0.35 ml, 2.5 mmol) and 3-(trifluoromethyl)phenyl isothiocyanate (862 µl, 5.68 mmol). The mixture was heated to reflux for 72 hours, concentrated and purified by column chromatography on silica gel (eluent: 1:2 ethyl acetate/hexane). The product was obtained in a yield of 284 mg (30%).

Example Compound 23

(2,4-Difluorophenyl)thiocarbamic acid O-(4-hydroxymethyl-5-oxo-2,3,4,5-tetrahydrobenzo[b]oxepin-4-ylmethyl)ester To a solution of 4,4-bis(hydroxymethyl)-3,4-dihydro-2H-benzo[b]oxepin-5-one (500 mg, 2.25 mmol) in 28 ml of tetrahydrofuran were added, at room temperature, triethylamine (0.34 ml, 2.48 mmol) and 2,4-difluorophenyl isothiocyanate (734 µl, 5.63 mmol). The mixture was heated to reflux for 72 hours, concentrated and purified by column chromatography on silica gel (eluent: 1:2 tert-butyl methyl ether/cyclohexane). The product was obtained in a yield of 376 mg (43%).

Example Compound 24

(2,4-Difluorophenyl)thiocarbamic acid O-(6-hydroxymethyl-5-oxo-6,7,8,9-tetrahydro-5H-benzocyclohepten-6-ylmethyl)ester To a solution of 6,6-bis(hydroxymethyl)-6,7,8,9-tetrahydrobenzocyclohepten-5-one (500 mg, 2.27 mmol) in 28 ml of tetrahydrofuran were added, at room temperature, triethylamine (0.35 ml, 2.50 mmol) and 2,4-difluorophenyl isothiocyanate (740 µl, 5.68 mmol). The mixture was heated to reflux for 72 hours, concentrated and purified by column chromatography on silica gel (eluent: 1:2 tert-butyl methyl ether/cyclohexane). The product was obtained in a yield of 234 mg (26%).

Example Compound 25

(3-Trifluoromethyl phenyl)carbamic acid 4-(3-trifluoromethyl phenyl)-carbamoyloxymethyl-5-oxo-2,3,4,5-tetrahydrobenzo[b]oxepin-4-ylmethyl ester To a solution of 4,4-bis(hydroxymethyl)-3,4-dihydro-2H-benzo[b]oxepin-5-one (500 mg, 2.25 mmol) in 28 ml of tetrahydrofuran were added, at room temperature, triethylamine (0.34 ml, 2.48 mmol) and 3-(trifluoromethyl)phenyl isocyanate (944 µl, 6.75 mmol). The mixture was stirred at room temperature for 18 hours, concentrated and purified by column chromatography on silica gel (eluent: 1:2 tert-butyl methyl ether/cyclohexane). The product was obtained in a yield of 35 mg (2.6%).

Example Compounds 26 and 27

Butylcarbamic acid 4-hydroxymethyl-5-oxo-2,3,4,5-tetrahydrobenzo[b]thiepin-4-ylmethyl ester and butylcarbamic acid 4-(butylcarbamoyloxymethyl)-5-oxo-2,3,4,5-tetrahydrobenzo[b]thiepin-4-ylmethyl ester To a solution of 4,4-bis(hydroxymethyl)-3,4-dihydro-2H-benzo[b]thiepin-5-one (500 mg, 2.098 mmol) in 26 ml of tetrahydrofuran were added, at room temperature, triethylamine (0.32 ml, 2.31 mmol) and n-butyl isocyanate (542 µl, 4.62 mmol). The mixture was heated to reflux for 24 hours, concentrated and purified by column chromatography on silica gel (eluent: 1:2 ethyl acetate/hexane). The two products were obtained in a yield of 265 mg (37%, Example 26) and 381 mg (42%, Example 27) respectively.

Example Compound 28

(4-Trifluoromethoxyphenyl)carbamic acid 4-hydroxymethyl-5-oxo-2,3,4,5-tetrahydrobenzo[b]thiepin-4-ylmethyl ester To a solution of 4,4-bis(hydroxymethyl-3,4-dihydro-2H-benzo[b]thiepin-5-one (500 mg, 2.098 mmol) in 26 ml of tetrahydrofuran were added, at room temperature, triethylamine (0.32 ml, 2.31 mmol) and 4-trifluoromethoxyphenyl isocyanate (696 µl, 4.62 mmol). The mixture was heated to reflux for 1 hour and stirred at RT for 72 hours, concentrated and purified by column chromatography on silica gel (eluent: 1:4 ethyl acetate/hexane). The product was obtained in a yield of 238 mg (26%).

Pharmacological Data

The affinity of the inventive substituted benzofused cycloheptanone derivatives for vanilloid receptor 1 (VR1/TRPV1 receptor) or for cannabinoid receptor CB1 and for cannabinoid receptor CB2 was determined as described above.

The inventive substituted benzofused cycloheptanone derivatives have a high affinity for the receptors mentioned.

| | VR1 (human) (% inhibition compared to 10 μM CP) | VR1 (rat) (% stimulation compared to 10 μM CP) | VR1 (rat) (% inhibition compared to 10 μM CP) | CB1 inhibition (10 μM, % inhibition) | CB2 inhibition (10 μM, % inhibition) |
|---|---|---|---|---|---|
| 1 | | | | | 42.2 |
| 2 | | | | 42 | 74.6 |
| 5 | 53.8 | | | | 36.2 |
| 6 | 26.7 | | | | 53.6 |
| 8 | | | | 47 | 76.2 |
| 9 | 51.3 | | 52.8 | | 28.3 |
| 14 | | | | | 61.8 |
| 16 | | | | | 63.4 |
| 17 | 17.1 | | 46.6 | | 3.8 |
| 18 | 31.5 | | 52.1 | | 15.6 |
| 19 | 13.3 | | 32.2 | | 40.3 |
| 20 | 21.8 | | 17.1 | | 41.0 |
| 21 | 36.3 | | 34.6 | | |
| 22 | 67.5 | 77.9 | 59.7 | | |
| 25 | 62 | 105 | 64.7 | | |

The invention claimed is:

1. A compound of the general formula I

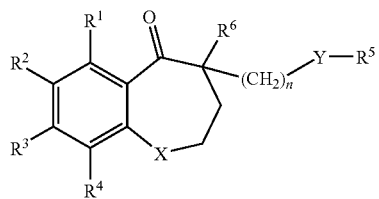

in which n is 1, 2 or 3;

X is $CH_2$, O, S, S(=O), S(=O)$_2$, N(H), N(R$^7$), N[C(=O)—R$^8$] or N[C(=O)—O—R$^9$];

Y is O, O—C(=O), O—C(=O)—O, O—S(=O)$_2$, O—C(=O)—N(H), O—C(=S)—N(H), N(H)—C(=O)—N(H) or N(H)—C(=S)—N(H); where the atom which binds to R$^5$ is always stated last;

R$^1$, R$^2$, R$^3$ and R$^4$ are each independently H, F, Cl, Br, I, —SF$_5$, —CN, —NC, —NO$_2$, —SO$_3$H, —NH$_2$, —OH, —SH, —OR$^{10}$, —SR$^{11}$, —NR$^{12}$R$^{13}$, —NH—R$^{14}$, —NH—C(=O)—R$^{15}$, —NR$^{16}$—C(=O)—R$^{17}$, —C(=O)—NH$_2$, —C(=O)—NH—R$^{18}$, —C(=O)—NR$^{19}$R$^{20}$, —C(=O)—H, —C(=O)—R$^{21}$, —C(=O)—OH, —C(=O)—OR$^{22}$, —O—C(=O)—R$^{23}$ or a linear or branched, saturated or unsaturated, unsubstituted or at least monosubstituted aliphatic group;

R$^5$ is a —C(=O)—R$^{24}$ group;
is a —S(=O)$_2$—R$^{25}$ group;
is a linear or branched, saturated or unsaturated, unsubstituted or at least monosubstituted aliphatic group;
is an unsubstituted or at least monosubstituted, unsaturated or saturated cycloaliphatic group optionally having at least one heteroatom as a ring member;
or an unsubstituted or at least monosubstituted aryl or heteroaryl group which may be bonded via a linear or branched, unsubstituted or at least monosubstituted alkylene, alkenylene or alkynylene group, and/or fused to an unsubstituted or at least monosubstituted mono- or polycyclic ring system;

R$^6$ is a hydrogen;
is —(CH$_2$)$_p$—Z—R$^{26}$ where p=1, 2 or 3;
or is —(CH$_2$)$_q$—OR$^{27}$ where q=1, 2 or 3;

R$^7$, R$^8$ and R$^9$ are each independently
a linear or branched, saturated or unsaturated, unsubstituted or at least monosubstituted aliphatic group;
or an unsubstituted or at least monosubstituted aryl or heteroaryl group which is bonded via a linear or branched, unsubstituted or at least monosubstituted alkylene, alkenylene or alkynylene group;

R$^{10}$, R$^{11}$, R$^{12}$, R$^{13}$, R$^{14}$, R$^{15}$, R$^{16}$, R$^{17}$, R$^{18}$, R$^{19}$, R$^{20}$, R$^{21}$, R$^{22}$ and R$^{23}$ are each independently
a linear or branched, saturated or unsaturated, unsubstituted or at least monosubstituted aliphatic group;
an unsubstituted or at least monosubstituted, unsaturated or saturated cycloaliphatic group optionally having at least one heteroatom as a ring member;
or an unsubstituted or at least monosubstituted aryl or heteroaryl group which may be bonded via a linear or branched, unsubstituted or at least monosubstituted alkylene, alkenylene or alkynylene group and/or may be fused to an unsubstituted or at least monosubstituted mono- or polycyclic ring system;

Z is O, O—C(=O), O—C(=O)—O, O—S(=O)$_2$, O—C(=O)—N(H), O—C(=S)—N(H), N(H), N(H)—C(=O)—N(H) or N(H)—C(=S)—N(H); where the atom which binds to R$^{26}$ is always stated last;

R$^{24}$, R$^{25}$, R$^{28}$ and R$^{29}$ are each independently
an unsubstituted or at least monosubstituted, unsaturated or saturated cycloaliphatic group optionally having at least one heteroatom as a ring member;
or an unsubstituted or at least monosubstituted aryl or heteroaryl group which may be fused to an unsubstituted or at least monosubstituted mono- or polycyclic ring system;

R$^{26}$ is a —C(=O)—R$^{28}$ group;
is a —S(=O)$_2$—R$^{29}$ group;
is a linear or branched, saturated or unsaturated, unsubstituted or at least monosubstituted aliphatic group;
is an unsubstituted or at least monosubstituted, unsaturated or saturated cycloaliphatic group optionally having at least one heteroatom as a ring member;
is an unsubstituted or at least monosubstituted aryl or heteroaryl group which may be bonded via a linear or branched, unsubstituted or at least monosubstituted alkylene, alkenylene or alkynylene group and/or may be fused to an unsubstituted or at least monosubstituted mono- or polycyclic ring system; and R$^{27}$ is a hydrogen;

in each case, as appropriate, in the form of one of its pure stereoisomers, of its racemates or in the form of a mixture of stereoisomers in any mixing ratio, or in each case in the form of corresponding salts.

2. A compound as claimed in claim 1, characterized in that
n is 1, 2 or 3;
X is $CH_2$, O, S, $S(=O)$, $S(=O)_2$, $N(H)$, $N(R^7)$, $N[C(=O)-R^8]$ or $N[C(=O)-O-R^9]$;
Y is O, $O-C(=O)$, $O-C(=O)-O$, $O-S(=O)_2$, $O-C(=O)-N(H)$, $O-C(=S)-N(H)$, $N(H)-C(=O)-N(H)$ or $N(H)-C(=S)-N(H)$; where the atom which binds to $R^5$ is always stated last;
$R^1$, $R^2$, $R^3$ and $R^4$ are each independently H, F, Cl, Br, I, $-SF_5$, $-CN$, $-NC$, $-NO_2$, $-SO_3H$, $-NH_2$, $-OH$, $-SH$, $-OR^{10}$, $-SR^{11}$, $-NR^{12}R^{13}$, $-NH-R^{14}$, $-NH-C(=O)-R^{15}$, $-NR^{16}-C(=O)-R^{17}$, $-C(=O)-NH_2$, $-C(=O)-NH-R^{18}$, $-C(=O)-NR^{19}R^{20}$, $-C(=O)-H$, $-C(=O)-R^{21}$, $-C(=O)-OH$, $-C(=O)-OR^{22}$, $-O-C(=O)-R^{23}$ or a linear or branched, saturated or unsaturated, optionally substituted $C_{1-10}$ aliphatic group;
$R^5$ is a $-C(=O)-R^{24}$ group;
is a $-S(=O)_2-R^{25}$ group;
is an unsaturated or saturated, optionally substituted 3-, 4-, 5-, 6-, 7-, 8- or 9-membered cycloaliphatic group;
is a linear or branched, saturated or unsaturated, optionally substituted $C_{1-10}$ aliphatic group;
or is an optionally substituted 5- to 14-membered aryl or heteroaryl group which may be fused to a saturated or unsaturated, optionally substituted mono- or polycyclic ring system and/or may be bonded via a $-(CH_2)-$, $-(CH_2)-(CH_2)-$ or $-(CH_2)-(CH_2)-(CH_2)-$ group;
$R^6$ is a hydrogen;
is $-(CH_2)_p-Z-R^{26}$ where p=1, 2 or 3;
or is $-(CH_2)_q-OR^{27}$ where q=1, 2 or 3;
$R^7$, $R^8$ and $R^9$ are each independently
a linear or branched, saturated or unsaturated, optionally substituted $C_{1-10}$ aliphatic group;
or an optionally substituted 5- to 14-membered aryl or heteroaryl group which is bonded via a $-(CH_2)-$, $-(CH_2)-(CH_2)-$ or $-(CH_2)-(CH_2)-(CH_2)-$ group;
$R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ are each independently
a linear or branched, saturated or unsaturated, optionally substituted $C_{1-10}$ aliphatic group;
an unsaturated or saturated, optionally substituted 3-, 4-, 5-, 6-, 7-, 8- or 9-membered cycloaliphatic group;
or an optionally substituted 5- to 14-membered aryl or heteroaryl group which may be fused to a saturated or unsaturated, optionally substituted mono- or polycyclic ring system and/or may be bonded via a $-(CH_2)-$, $-(CH_2)-(CH_2)-$ or $-(CH_2)-(CH_2)-(CH_2)-$ group;
Z is O, $O-C(=O)$, $O-C(=O)-O$, $O-S(=O)_2$, $O-C(=O)-N(H)$, $O-C(=S)-N(H)$, $N(H)-C(=O)-N(H)$ or $N(H)-C(=S)-N(H)$; where the atom which binds to $R^{26}$ is always stated last;
$R^{24}$, $R^{25}$, $R^{28}$ and $R^{29}$ are each independently
an unsaturated or saturated, optionally substituted 3-, 4-, 5-, 6-, 7-, 8- or 9-membered cycloaliphatic group;
or an optionally substituted 5- to 14-membered aryl- or heteroaryl group which may be fused to a saturated or unsaturated, optionally substituted mono- or polycyclic ring system;
$R^{26}$ is a $-C(=O)-R^{28}$ group;
is a $-S(=O)_2-R^{29}$ group;
is an unsaturated or saturated, optionally substituted 3-, 4-, 5-, 6-, 7-, 8- or 9-membered cycloaliphatic group;
is a linear or branched, saturated or unsaturated, optionally substituted $C_{1-10}$ aliphatic group;
or an optionally substituted 5- to 14-membered aryl or heteroaryl group, which may be fused to a saturated or unsaturated, optionally substituted mono- or polycyclic ring system and/or may be bonded via a $-(CH_2)-$, $-(CH_2)-(CH_2)-$ or $-(CH_2)-(CH_2)-(CH_2)-$ group;
and
$R^{27}$ is a hydrogen;
where
the aforementioned $C_{1-10}$ aliphatic groups may each optionally be substituted by 1, 2, 3, 4, 5, 6, 7, 8 or 9 substituents selected independently from the group consisting of F, Cl, Br, I, $-CN$, $-NO_2$, $-OH$, $-SH$ and $-NH_2$;
the aforementioned aryl or heteroaryl groups may each optionally be substituted by 1, 2, 3, 4 or 5 substituents selected independently from the group consisting of F, Cl, Br, I, $-CN$, $-CF_3$, $-SF_5$, $-OH$, $-O-C_{1-5}$-alkyl, $-NH_2$, $-NO_2$, $-O-CF_3$, $-S-CF_3$, $-SH$, $-S-C_{1-5}$-alkyl, $-C_{1-10}$-alkyl, $-C(=O)-OH$, $-C(=O)-O-C_{1-5}$-alkyl, $-O-C(=O)-C_{1-5}$-alkyl, $-NH-C_{1-5}$-alkyl, $-N(C_{1-5}$-alkyl$)_2$, $-NH-C(=O)-O-C_{1-5}$-alkyl, $-C(=O)-H$, $-C(=O)-C_{1-5}$-alkyl, $-C(=O)-NH_2$, $-C(=O)-NH-C_{1-5}$-alkyl, $C(=O)-N-(C_{1-5}$-alkyl$)_2$, $-S(=O)_2-C_{1-5}$-alkyl, $-S(=O)_2$-phenyl, $-NH-S(=O)_2-C_{1-5}$-alkyl, $-S(=O)_2-NH-C_{1-5}$-alkyl, cyclohexyl, cyclopentyl, pyridinyl, pyridazinyl, $-(CH_2)$-benzo[b]furanyl, $-O$-phenyl, $-O$-benzyl, phenyl and benzyl, where the cyclic moiety of the pyridinyl, cyclopentyl, cyclohexyl, pyridazinyl, $-S(=O)_2$-phenyl, $-O$-phenyl, $-O$-benzyl, phenyl, $-(CH_2)$-benzo[b]furanyl and benzyl groups may in each case be substituted by 1, 2, 3, 4 or 5 substituents selected independently from the group consisting of F, Cl, Br, $-OH$, $-CF_3$, $-SF_5$, $-CN$, $-NO_2$, $-C_{1-5}$-alkyl, $-O-C_{1-5}$-alkyl, $-O-CF_3$, $-S-CF_3$, phenyl and $-O$-benzyl,
and the aforementioned heteroaryl groups may each optionally have 1, 2, 3, 4 or 5 heteroatom(s) selected independently from the group consisting of oxygen, nitrogen and sulfur as ring member(s);
the rings of the aforementioned mono- or polycyclic ring systems may each be optionally substituted by 1, 2, 3, 4 or 5 substituents selected independently from the group consisting of oxo $(=O)$, thioxo $(=S)$, F, Cl, Br, I, $-CN$, $-CF_3$, $-SF_5$, $-OH$, $-O-C_{1-5}$-alkyl, $-NH_2$, $-NO_2$, $-O-CF_3$, $-S-CF_3$, $-SH$, $-S-C_{1-5}$-alkyl, $-C_{1-5}$-alkyl, $-C(=O)-OH$, $-C(=O)-O-C_{1-5}$-alkyl, $-O-C(=O)-C_{1-5}$-alkyl, $-NH-C_{1-5}$-alkyl, $-N(C_{1-5}$-alkyl$)_2$, $-NH-C(=O)-O-C_{1-5}$-alkyl, $-C(=O)-H$, $-C(=O)-C_{1-5}$-alkyl, $-C(=O)-NH_2$, $-C(=O)-NH-C_{1-5}$-alkyl, $C(=O)-N-(C_{1-5}$-alkyl$)_2$, $-S(=O)_2-C_{1-5}$-alkyl, $-S(=O)_2$-phenyl, $-NH-S(=O)_2-C_{1-5}$-alkyl, $-S(=O)_2-NH-C_{1-5}$-alkyl, cyclohexyl, cyclopentyl, pyridinyl, pyridazinyl, $-(CH_2)$-benzo[b]furanyl, $-O$-phenyl, $-O$-benzyl, phenyl and benzyl, where the cyclic moiety of the pyridinyl, cyclopentyl, cyclohexyl, pyridazinyl, $-S(=O)_2$-phenyl, $-O$-phenyl, $-O$-benzyl, phenyl, $-(CH_2)$-benzo[b]furanyl and benzyl groups may in each case be substituted by 1, 2, 3, 4 or 5 substituents selected independently from the group consisting of F, Cl, Br, $-OH$, $-CF_3$, $-SF_5$, $-CN$, $-NO_2$, $-C_{1-5}$-alkyl, $-O-C_{1-5}$-alkyl, $-O-CF_3$, $-S-CF_3$, phenyl and $-O$-benzyl, and the rings of the aforementioned mono- or polycyclic ring systems are each 5-, 6- or 7-membered and may each optionally have 1, 2, 3, 4 or 5 heteroatom(s) as ring member(s) which are independently selected from the group consisting of oxygen, nitrogen and sulfur;

the aforementioned cycloaliphatic groups may each optionally be substituted by 1, 2, 3, 4 or 5 substituents selected independently from the group consisting of oxo (=O), thioxo (=S), F, Cl, Br, I, —CN, —CF$_3$, —SF$_5$, —OH, —O—C$_{1-5}$-alkyl, —NH$_2$, —NO$_2$, —O—CF$_3$, —S—CF$_3$, —SH, —S—C$_{1-5}$-alkyl, —C$_{1-5}$-alkyl, —C(=O)—OH, —C(=O)—O—C$_{1-5}$-alkyl, —O—C(=O)—C$_{1-5}$-alkyl, —N(C$_{1-5}$-alkyl)$_2$, —NH—C(=O)—O—C$_{1-5}$-alkyl, —C(=O)—H, —C(=O)—C$_{1-5}$-alkyl, —C(=O)—NH$_2$, —C(=O)—NH—C$_{1-5}$-alkyl, C(=O)—N—(C$_{1-5}$-alkyl)$_2$, —S(=O)$_2$—C$_{1-5}$-alkyl, —S(=O)$_2$-phenyl, —NH—S(=O)$_2$—C$_{1-5}$-alkyl, —S(=O)$_2$—NH—C$_{1-5}$-alkyl, cyclohexyl, cyclopentyl, pyridinyl, pyridazinyl, —(CH$_2$)-benzo[b]furanyl, —O-phenyl, —O-benzyl, phenyl and benzyl, where the cyclic moiety of the pyridinyl, cyclopentyl, cyclohexyl, pyridazinyl, —S(=O)$_2$-phenyl, —O-phenyl, —O-benzyl, phenyl, —(CH$_2$)-benzo[b]furanyl and benzyl groups may in each case be substituted by 1, 2, 3, 4 or 5 substituents selected independently from the group consisting of F, Cl, Br, —OH, —CF$_3$, —SF$_5$, —CN, —NO$_2$, —C$_{1-5}$-alkyl, —O—C$_{1-5}$-alkyl, —O—CF$_3$, —S—CF$_3$, phenyl and —O-benzyl, and the aforementioned cycloaliphatic groups may each optionally have 1, 2, 3, 4 or 5 heteroatom(s) selected independently from the group consisting of oxygen, nitrogen and sulfur as ring member(s), in each case, as appropriate, in the form of one of its pure stereoisomers, of its racemates or in the form of a mixture of stereoisomers in any mixing ratio, or in each case in the form of corresponding salts.

3. A compound as claimed in claim 1, characterized in that n is 1.

4. A compound as claimed in claim 1, characterized in that Y is O, O—C(=O), O—C(=O)—O, O—S(=O)$_2$, O—C(=S)—N(H) or O—C(=O)—N(H).

5. A compound as claimed in claim 1, characterized in that R$^1$, R$^2$, R$^3$ and R$^4$ are each independently H, F, Cl, Br, I, —SF$_5$, —CN, —NC, —NO$_2$, —SO$_3$H, —NH$_2$, —OH, —SH, —OR$^{10}$, —SR$^{11}$, —NR$^{12}$R$^{13}$, —NH—R$^{14}$, —NH—C(=O)—R$^{15}$, —C(=O)—OH, —C(=O)—OR$^{22}$, —O—C(=O)—R$^{23}$ or a group selected form the group consisting of methyl, ethyl, n-propyl, isopropyl, n-butyl, sec-butyl, isobutyl, tert-butyl, 1,1-dimethylpropyl, n-pentyl, sec-pentyl, n-hexyl and n-heptyl; in each case optionally substituted by 1, 2, 3, 4 or 5 substituents selected independently from the group consisting of F, Cl, Br, I, —CN, —NO$_2$, —OH, —SH and —NH$_2$.

6. A compound as claimed in claim 1, characterized in that R$^5$ is a —C(=O)—R$^{24}$ group;
is a —S(=O)$_2$—R$^{25}$ group;
is a group selected from the group consisting of methyl, ethyl, n-propyl, isopropyl, n-butyl, sec-butyl, isobutyl, tert-butyl, 1,1-dimethylpropyl, n-pentyl, sec-pentyl, n-hexyl and n-heptyl; in each case optionally substituted by 1, 2, 3, 4 or 5 substituents selected independently from the group consisting of F, Cl, Br, I, —CN, —NO$_2$, —OH, —SH and —NH$_2$;
is a group selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl and thiomorpholinyl; in each case optionally substituted by 1, 2, 3, 4 or 5 substituents selected independently from the group consisting of oxo (=O), thioxo (=S), F, Cl, Br, I, —CN, —CF$_3$, —SF$_5$, —OH, —O—CH$_3$, —O—C$_2$H$_5$, —NH$_2$, —NO$_2$, —O—CF$_3$, —S—CF$_3$, —SH, —S—CH$_3$, —S—C$_2$H$_5$, methyl, ethyl, n-propyl, isopropyl, n-butyl, sec-butyl, isobutyl, tert-butyl, —C(=O)—OH, —C(=O)-β-CH$_3$, —C(=O)—O—C$_2$H$_5$, —C(=O)—O—C(CH$_3$)$_3$, —O—C(=O)—CH$_3$, —O—C(=O)—C$_2$H$_5$, —O—C(=O)—C(CH$_3$)$_3$, —N(CH$_3$)$_2$, —N(C$_2$H$_5$)$_2$, —NH—CH$_3$, —NH—C$_2$H$_5$, —NH—C(=O)—O—CH$_3$, —NH—C(=O)—O—C$_2$H$_5$, —NH—C(=O)—O—C(CH$_3$)$_3$, —C(=O)—H, —C(=O)—CH$_3$, —C(=O)—C$_2$H$_5$, —C(=O)—C(CH$_3$)$_3$, —C(=O)—NH$_2$, —C(=O)—NH—CH$_3$, —C(=O)—NH—C$_2$H$_5$, —C(=O)—N—(CH$_3$)$_2$, —C(=O)—N—(C$_2$H$_5$)$_2$, —S(=O)$_2$—CH$_3$ and —S(=O)$_2$—C$_2$H$_5$;

or is a group selected from the group consisting of phenyl, naphthyl, (1,3)-benzodioxolyl, (1,4)-benzodioxanyl, thiophenyl, furanyl, pyrrolyl, pyrazolyl, pyranyl, pyridinyl, imidazolyl, indolyl, isoindolyl, benzo[b]furanyl, benzo[b]thiophenyl, thiazolyl, oxazolyl, isoxazolyl, pyridazinyl, pyrazinyl, pyrimidinyl, indazolyl, quinazolinyl, quinolinyl, isoquinolinyl, benzimidazolinyl, benzoxazolyl, benzisoxazolyl and benzothiazolyl, optionally bonded via a —(CH$_2$)—, —(CH$_2$)—(CH$_2$)— or —(CH$_2$)—(CH$_2$)—(CH$_2$)— group and in each case optionally substituted by 1, 2, 3, 4 or 5 substituents selected independently from the group consisting of F, Cl, Br, I, —CN, —CF$_3$, —SF$_5$, —OH, —O—CH$_3$, —O—C$_2$H$_5$, —NH$_2$, —NO$_2$, —O—CF$_3$, —S—CF$_3$, —SH, —S—CH$_3$, —S—C$_2$H$_5$, methyl, ethyl, n-propyl, isopropyl, n-butyl, sec-butyl, isobutyl, tert-butyl, —C(=O)—OH, —C(=O)—O—CH$_3$, —C(=O)—O—C$_2$H$_5$, —C(=O)—O—C(CH$_3$)$_3$, —O—C(=O)—CH$_3$, —O—C(=O)—C$_2$H$_5$, —O—C(=O)—C(CH$_3$)$_3$, —N(CH$_3$)$_2$, —N(C$_2$H$_5$)$_2$, —NH—CH$_3$, —NH—C$_2$H$_5$, —NH—C(=O)—O—CH$_3$, —NH—C(=O)—O—C$_2$H$_5$, —NH—C(=O)—O—C(CH$_3$)$_3$, —C(=O)—H, —C(=O)—CH$_3$, —C(=O)—C$_2$H$_5$, —C(=O)—C(CH$_3$)$_3$, —C(=O)—NH$_2$, —C(=O)—NH—CH$_3$, —C(=O)—NH—C$_2$H$_5$, —C(=O)—N—(CH$_3$)$_2$, —C(=O)—N—(C$_2$H$_5$)$_2$, —S(=O)$_2$—CH$_3$, —S(=O)$_2$—C$_2$H$_5$, —S(=O)$_2$-phenyl, —NH—S(=O)$_2$—CH$_3$, —NH—S(=O)$_2$—C$_2$H$_5$, —S(=O)$_2$—NH—CH$_3$, —S(=O)$_2$—NH—C$_2$H$_5$, cyclohexyl, cyclopentyl, pyridinyl, pyridazinyl, —(CH$_2$)-benzo[b]furanyl, —O-phenyl, —O-benzyl, phenyl and benzyl where the cyclic moiety of the pyridinyl, cyclopentyl, cyclohexyl, pyridazinyl, —S(=O)$_2$-phenyl, —O-phenyl, —O-benzyl, phenyl, —(CH$_2$)-benzo[b]furanyl and benzyl groups may in each case optionally be substituted by 1, 2, 3, 4 or 5 substituents selected independently from the group consisting of F, Cl, Br, —OH, —CF$_3$, —SF$_5$, —CN, —NO$_2$, methyl, ethyl, n-propyl, isopropyl, n-butyl, sec-butyl, isobutyl, tert-butyl, —O—CH$_3$, —O—C$_2$H$_5$, —O—CF$_3$, —S—CF$_3$, phenyl and —O-benzyl.

7. A compound as claimed in claim 1, characterized in that $R^6$ is a hydrogen;
   is $-(CH_2)_p Z-R^{26}$
   or is $-(CH_2)-OR^{27}$.

8. A compound as claimed in claim 1, characterized in that $R^7$, $R^8$ and $R^9$ are each independently
   a group selected from the group consisting of methyl, ethyl, n-propyl, isopropyl, n-butyl, sec-butyl, isobutyl, tert-butyl, 1,1-dimethylpropyl, n-pentyl, sec-pentyl, n-hexyl and n-heptyl; in each case optionally substituted by 1, 2, 3, 4 or 5 substituents selected independently from the group consisting of F, Cl, Br, I, $-CN$, $-NO_2$, $-OH$, $-SH$ and $-NH_2$;
   or a group selected from the group consisting of phenyl, naphthyl, thiophenyl, furanyl, pyridinyl, thiazolyl and oxazolyl, in each case optionally substituted by 1, 2, 3, 4 or 5 substituents selected independently from the group consisting of F, Cl, Br, I, $-CN$, $-CF_3$, $-SF_5$, $-OH$, $-O-CH_3$, $-O-C_2H_5$, $-NH_2$, $-NO_2$, $-O-CF_3$, $-S-CF_3$, $-SH$, $-S-CH_3$, $-S-C_2H_5$, methyl, ethyl, n-propyl, isopropyl, n-butyl, sec-butyl, isobutyl, tert-butyl, $-C(=O)-OH$, $-C(=O)-O-CH_3$, $-C(=O)-O-C_2H_5$, $-C(=O)-O-C(CH_3)_3$, $-O-C(=O)-CH_3$, $-O-C(=O)-C_2H_5$, $-O-C(=O)-C(CH_3)_3$, $-N(CH_3)_2$, $-N(C_2H_5)_2$, $-NH-CH_3$, $-NH-C_2H_5$, $-NH-C(=O)-O-CH_3$, $-NH-C(=O)-O-C_2H_5$, $-NH-C(=O)-O-C(CH_3)_3$, $-C(=O)-H$, $-C(=O)-CH_3$, $-C(=O)-C_2H_5$, $-C(=O)-C(CH_3)_3$, and may be bonded via a $-(CH_2)-$, $-(CH_2)-(CH_2)-$ or $-(CH_2)-(CH_2)-(CH_2)-$ group.

9. A compound as claimed in claim 1, characterized in that $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ are each independently
   a group selected from the group consisting of methyl, ethyl, n-propyl, isopropyl, n-butyl, sec-butyl, isobutyl, tert-butyl, 1,1-dimethylpropyl, n-pentyl, sec-pentyl, n-hexyl and n-heptyl; in each case optionally substituted by 1, 2, 3, 4 or 5 substituents selected independently from the group consisting of F, Cl, Br, I, $-CN$, $-NO_2$, $-OH$, $-SH$ and $-NH_2$;
   a group selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl and thiomorpholinyl;
   or a group selected from the group consisting of phenyl, naphthyl, (1,3)-benzodioxolyl, (1,4)-benzodioxanyl, thiophenyl, furanyl, pyrrolyl, pyrazolyl, pyranyl, pyridinyl, imidazolyl, indolyl, isoindolyl, benzo[b]furanyl, benzo[b]thiophenyl, thiazolyl, oxazolyl, isoxazolyl, pyridazinyl, pyrazinyl, pyrimidinyl, indazolyl, quinazolinyl, quinolinyl, isoquinolinyl, benzimidazolinyl, benzoxazolyl, benzisoxazolyl and benzothiazolyl, optionally bonded via a $-(CH_2)-$, $-(CH_2)-(CH_2)-$ or $-(CH_2)-(CH_2)-(CH_2)-$ group and in each case optionally substituted by 1, 2, 3, 4 or 5 substituents selected independently from the group consisting of F, Cl, Br, I, $-CN$, $-CF_3$, $-SF_5$, $-OH$, $-O-CH_3$, $-O-C_2H_5$, $-NH_2$, $-NO_2$, $-O-CF_3$, $-S-CF_3$, $-SH$, $-S-CH_3$, $-S-C_2H_5$, methyl, ethyl, n-propyl, isopropyl, n-butyl, sec-butyl, isobutyl, tert-butyl, $-C(=O)-OH$, $-C(=O)-O-CH_3$, $-C(=O)-O-C_2H_5$, $-C(=O)-O-C(CH_3)_3$, $-O-C(=O)-CH_3$, $-O-C(=O)-C_2H_5$, $-O-C(=O)-C(CH_3)_3$, $-N(CH_3)_2$, $-N(C_2H_5)_2$, $-NH-CH_3$, $-NH-C_2H_5$, $-NH-C(=O)-O-CH_3$, $-NH-C(=O)-O-C_2H_5$, $-NH-C(=O)-O-C(CH_3)_3$, $-C(=O)-H$, $-C(=O)-CH_3$, $-C(=O)-C_2H_5$, $-C(=O)-C(CH_3)_3$, $-C(=O)-NH_2$, $-C(=O)-NH-CH_3$, $-C(=O)-NH-C_2H_5$, $-C(=O)-N-(CH_3)_2$, and $-C(=O)-N-(C_2H_5)_2$.

10. A compound as claimed in claim 1, characterized in that $R^{24}$, $R^{25}$, $R^{28}$ and $R^{29}$ are each independently
    a group selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl and thiomorpholinyl;
    or a group selected from the group consisting of phenyl, naphthyl, (1,3)-benzodioxolyl, (1,4)-benzodioxanyl, thiophenyl, furanyl, pyrrolyl, pyrazolyl, pyranyl, pyridinyl, imidazolyl, indolyl, isoindolyl, benzo[b]furanyl, benzo[b]thiophenyl, thiazolyl, oxazolyl, isoxazolyl, pyridazinyl, pyrazinyl, pyrimidinyl, indazolyl, quinazolinyl, quinolinyl, isoquinolinyl, benzimidazolinyl, benzoxazolyl, benzisoxazolyl and benzothiazolyl, in each case optionally substituted by 1, 2, 3, 4 or 5 substituents selected independently from the group consisting of F, Cl, Br, I, $-CN$, $-CF_3$, $-SF_5$, $-OH$, $-O-CH_3$, $-O-C_2H_5$, $-NH_2$, $-NO_2$, $-O-CF_3$, $-S-CF_3$, $-SH$, $-S-CH_3$, $-S-C_2H_5$, methyl, ethyl, n-propyl, isopropyl, n-butyl, sec-butyl, isobutyl, tert-butyl, $-C(=O)-OH$, $-C(=O)-O-CH_3$, $-C(=O)-O-C_2H_5$, $-C(=O)-O-C(CH_3)_3$, $-O-C(=O)-CH_3$, $-O-C(=O)-C_2H_5$, $-O-C(=O)-C(CH_3)_3$, $-N(CH_3)_2$, $-N(C_2H_5)_2$, $-NH-CH_3$, $-NH-C_2H_5$, $-NH-C(=O)-O-CH_3$, $-NH-C(=O)-O-C_2H_5$, $-NH-C(=O)-O-C(CH_3)_3$, $-C(=O)-H$, $-C(=O)-CH_3$, $-C(=O)-C_2H_5$, $-C(=O)-C(CH_3)_3$, $-C(=O)-NH_2$, $-C(=O)-NH-CH_3$, $-C(=O)-NH-C_2H_5$, $-C(=O)-N-(CH_3)_2$, and $-C(=O)-N-(C_2H_5)_2$.

11. A compound as claimed in claim 1, characterized in that $R^{26}$ is a $-C(=O)-R^{28}$ group;
    is a $-S(=O)_2-R^{29}$ group;
    is a group selected from the group consisting of methyl, ethyl, n-propyl, isopropyl, n-butyl, sec-butyl, isobutyl, tert-butyl, 1,1-dimethylpropyl, n-pentyl, sec-pentyl, n-hexyl and n-heptyl; in each case optionally substituted by 1, 2, 3, 4 or 5 substituents selected independently from the group consisting of F, Cl, Br, I, $-CN$, $-NO_2$, $-OH$, $-SH$ and $-NH_2$;
    is a selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl and thiomorpholinyl; in each case optionally substituted by 1, 2, 3, 4 or 5 substituents selected independently from the group consisting of oxo ($=O$), thioxo ($=S$), F, Cl, Br, I, $-CN$, $-CF_3$, $-SF_5$, $-OH$, $-O-CH_3$, $-O-C_2H_5$, $-NH_2$, $-NO_2$, $-O-CF_3$, $-S-CF_3$, $-SH$, $-S-CH_3$, $-S-C_2H_5$, methyl, ethyl, n-propyl, isopropyl, n-butyl, sec-butyl, isobutyl, tert-butyl, $-C(=O)-OH$, $-C(=O)-O-CH_3$, $-C(=O)-O-C_2H_5$, —C(=O)—O—C(CH₃)₃, —O—C(=O)—CH₃, —O—C(=O)—C₂H₅, —O—C(=O)—C(CH₃)₃, —N(CH₃)₂, —N(C₂H₅)₂, —NH—CH₃, —NH—C₂H₅, —NH—C(=O)—O—CH₃, —NH—C(=O)—O—C₂H₅, —NH—C(=O)—O—C(CH₃)₃, —C(=O)—H, —C(=O)—CH₃, —C(=O)—C₂H₅, —C(=O)—C(CH₃)₃, —C(=O)—NH₂, —C(=O)—NH—CH₃, —C(=O)—NH—C₂H₅, —C(=O)—N—(CH₃)₂, —C(=O)—N—(C₂H₅)₂, —S(=O)₂—CH₃ and —S(=O)₂—C₂H₅;

or a group selected from the group consisting of phenyl, naphthyl, (1,3)-benzodioxolyl, (1,4)-benzodioxanyl, thiophenyl, furanyl, pyrrolyl, pyrazolyl, pyranyl, pyridinyl, imidazolyl, indolyl, isoindolyl, benzo[b]furanyl, benzo[b]thiophenyl, thiazolyl, oxazolyl, isoxazolyl, pyridazinyl, pyrazinyl, pyrimidinyl, indazolyl, quinazolinyl, quinolinyl, isoquinolinyl, benzimidazolinyl, benzoxazolyl, benzisoxazolyl and benzothiazolyl, optionally bonded via a —(CH₂)—, —(CH₂)—(CH₂)— or —(CH₂)—(CH₂)—(CH₂)— group and in each case optionally substituted by 1, 2, 3, 4 or 5 substituents selected independently from the group consisting of F, Cl, Br, I, —CN, —CF₃, —SF₅, —OH, —O—CH₃, —O—C₂H₅, —NH₂, —NO₂, —O—CF₃, —S—CF₃, —SH, —S—CH₃, —S—C₂H₅, methyl, ethyl, n-propyl, isopropyl, n-butyl, sec-butyl, isobutyl, tert-butyl, —C(=O)—OH, —C(=O)—O—CH₃, —C(=O)—O—C₂H₅, —C(=O)—O—C(CH₃)₃, —O—C(=O)—CH₃, —O—C(=O)—C₂H₅, —O—C(=O)—C(CH₃)₃, —N(CH₃)₂, —N(C₂H₅)₂, —NH—CH₃, —NH—C₂H₅, —NH—C(=O)—O—CH₃, —NH—C(=O)—O—C₂H₅, —NH—C(=O)—O—C(CH₃)₃, —C(=O)—H, —C(=O)—CH₃, —C(=O)—C₂H₅, —C(=O)—C(CH₃)₃, —C(=O)—NH₂, —C(=O)—NH—CH₃, —C(=O)—NH—C₂H₅, —C(=O)—N—(CH₃)₂, —C(=O)—N—(C₂H₅)₂, —S(=O)₂—CH₃, —S(=O)₂—C₂H₅, —S(=O)₂-phenyl, —NH—S(=O)₂—CH₃, —NH—S(=O)₂—C₂H₅, —S(=O)₂—NH—CH₃, —S(=O)₂—NH—C₂H₅, cyclohexyl, cyclopentyl, pyridinyl, pyridazinyl, —(CH₂)-benzo[b]furanyl, —O-phenyl, —O-benzyl, phenyl and benzyl; where the cyclic moiety of the pyridinyl, cyclopentyl, cyclohexyl, pyridazinyl, —S(=O)₂-phenyl, —O-phenyl, —O-benzyl, phenyl, —(CH₂)-benzo[b]furanyl and benzyl groups may in each case be substituted by 1, 2, 3, 4 or 5 substituents selected independently from the group consisting of F, Cl, Br, —OH, —CF₃, —SF₅, —CN, —NO₂, methyl, ethyl, n-propyl, isopropyl, n-butyl, sec-butyl, isobutyl, tert-butyl, —O—CH₃, —O—C₂H₅, —O—CF₃, —S—CF₃, phenyl and —O-benzyl.

12. A compound as claimed in claim 1, characterized in that n is 1;

X is CH₂, O, S, S(=O), S(=O)₂, N(H), N(R⁷), N[C(=O)—R⁸] or N[C(=O)—O—R⁹];

Y is O, O—C(=O), O—C(=O)—O, O—S(=O)₂, O—C(=S)—N(H) or O—C(=O)—N(H);

R¹, R², R³ and R⁴ are each independently
H, F, Cl, Br, I, —SF₅, —CN, —NC, —NO₂, —OH, —SH, —OR¹⁰, —SR¹¹, —NR¹²R¹³, or a group selected from the group consisting of methyl, —CF₃, —CHF₂, —CH₂F, —CCl₃, —CBr₃, —CH₂—CN, —CH₂—NO₂, ethyl, —CF₂—CF₃, —CH₂—CF₃, —CCl₂—CCl₃, —CF₂—CH₃, —CH₂—CH₂—CN, —CH₂—CH₂—NO₂, n-propyl, —CF₂—CF₂—CF₃, —CH₂—CH₂—CH₂—CN, —CH₂—CH₂—CH₂—NO₂, isopropyl, n-butyl, sec-butyl, isobutyl, tert-butyl, 1,1-dimethylpropyl, n-pentyl, sec-pentyl, n-hexyl and n-heptyl;

R⁵ is a —C(=O)—R²⁴ group;
is a —S(=O)₂—R²⁵ group;
is a group selected from the group consisting of methyl, ethyl, n-propyl, isopropyl, n-butyl, sec-butyl, isobutyl, tert-butyl, 1,1-dimethylpropyl, n-pentyl, sec-pentyl, n-hexyl and n-heptyl;
is a group selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl and thiomorpholinyl;
or is a group selected from the group consisting of phenyl, benzyl, phenethyl, naphthyl, (1,3)-benzodioxolyl, (1,4)-benzodioxanyl, thiophenyl, furanyl, pyrrolyl, pyrazolyl, pyranyl, pyridinyl, imidazolyl, indolyl, isoindolyl, benzo[b]furanyl, benzo[b]thiophenyl, thiazolyl, oxazolyl, isoxazolyl, pyridazinyl, pyrazinyl, pyrimidinyl, indazolyl, quinazolinyl, quinolinyl, isoquinolinyl, benzimidazolinyl, benzoxazolyl, benzisoxazolyl and benzothiazolyl, optionally bonded via a —(CH₂)—, —(CH₂)—(CH₂)— or —(CH₂)—(CH₂)—(CH₂)— group and in each case optionally substituted by 1, 2, 3, 4 or 5 substituents selected independently from the group consisting of F, Cl, Br, I, —CN, —CF₃, —SF₅, —OH, —O—CH₃, —O—C₂H₅, —NH₂, —NO₂, —O—CF₃, —S—CF₃, —SH, —S—CH₃, —S—C₂H₅, methyl, ethyl, n-propyl, isopropyl, n-butyl, sec-butyl, isobutyl, tert-butyl, —C(=O)—OH, —C(=O)—O—CH₃, —C(=O)—O—C₂H₅, —C(=O)—O—C(CH₃)₃, —O—C(=O)—CH₃, —O—C(=O)—C₂H₅, —O—C(=O)—C(CH₃)₃, —N(CH₃)₂, —N(C₂H₅)₂, —NH—CH₃, —NH—C₂H₅, —NH—C(=O)—O—CH₃, —NH—C(=O)—O—C₂H₅, —NH—C(=O)—O—C(CH₃)₃, —C(=O)—H, —C(=O)—CH₃, —C(=O)—C₂H₅, —C(=O)—C(CH₃)₃, —C(=O)—NH₂, —C(=O)—NH—CH₃, —C(=O)—NH—C₂H₅, —C(=O)—N—(CH₃)₂, —C(=O)—N—(C₂H₅)₂, —S(=O)₂—CH₃, —S(=O)₂—C₂H₅, —NH—S(=O)₂—CH₃, —NH—S(=O)₂—C₂H₅, —S(=O)₂—NH—CH₃ and —S(=O)₂—NH—C₂H₅;

R⁶ is a hydrogen;
is —(CH₂)—Z—R²⁶;
or is —(CH₂)—OR²⁷;

R⁷, R⁸ and R⁹ are each independently a group selected from the group consisting of methyl, ethyl, n-propyl, isopropyl, n-butyl, sec-butyl, isobutyl, tert-butyl, 1,1-dimethylpropyl, n-pentyl, sec-pentyl, n-hexyl and n-heptyl;
or a group selected from the group consisting of benzyl and phenethyl, in each case optionally substituted by 1, 2, 3, 4 or 5 substituents selected independently from the group consisting of F, Cl, Br, I, —CN, —CF₃, —SF₅, —OH, —O—CH₃, —O—C₂H₅, —NH₂, —NO₂, —O—CF₃, —S—CF₃, —SH, —S—CH₃, —S—C₂H₅, methyl, ethyl, n-propyl, isopropyl, n-butyl, sec-butyl, isobutyl and tert-butyl;

R¹⁰, R¹¹, R¹² and R¹³, are each independently
a group selected from the group consisting of methyl, —CF₃, —CHF₂, —CH₂F, —CCl₃, —CBr₃, —CH₂—CN, —CH₂—NO₂, ethyl, —CF₂—CF₃, —CH₂—CF₃, —CCl₂—CCl₃, —CF₂—CH₃, —CH$_2$—CH$_2$—CN, —CH$_2$—CH$_2$—NO$_2$, n-propyl, isopropyl, n-butyl, sec-butyl, isobutyl, tert-butyl, 1,1-dimethylpropyl, n-pentyl, sec-pentyl, n-hexyl and n-heptyl;

or a group selected from the group consisting of phenyl, benzyl and phenethyl, in each case optionally substituted by 1, 2, 3, 4 or 5 substituents selected independently from the group consisting of F, Cl, Br, I, —CN, —CF$_3$, —SF$_5$, —OH, —O—CH$_3$, —O—C$_2$H$_5$, —NH$_2$, —NO$_2$, —O—CF$_3$, —S—CF$_3$, —SH, —S—CH$_3$, —S—C$_2$H$_5$, methyl, ethyl, n-propyl, isopropyl, n-butyl, sec-butyl, isobutyl and tert-butyl;

Z is O, O—C(=O), O—C(=O)—O, O—S(=O)$_2$, O—C(=S)—N(H) or O—C(=O)—N(H);

$R^{24}$ and $R^{25}$ are each independently a group selected from the group consisting of phenyl, naphthyl, thiophenyl, furanyl and pyridinyl, in each case optionally substituted by 1, 2, 3, 4 or 5 substituents selected independently from the group consisting of F, Cl, Br, I, —CN, —CF$_3$, —SF$_5$, —OH, —O—CH$_3$, —O—C$_2$H$_5$, —NH$_2$, —NO$_2$, —O—CF$_3$, —S—CF$_3$, —SH, —S—CH$_3$, —S—C$_2$H$_5$, methyl, ethyl, n-propyl, isopropyl, n-butyl, sec-butyl, isobutyl, tert-butyl, —N(CH$_3$)$_2$, —N(C$_2$H$_5$)$_2$, —NH—CH$_3$ and —NH—C$_2$H$_5$;

$R^{26}$ is a —C(=O)—$R^{28}$ group;

is a —S(=O)$_2$—$R^{29}$ group;

is a group selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl and thiomorpholinyl;

is a group selected from the group consisting of methyl, ethyl, n-propyl, isopropyl, n-butyl, sec-butyl, isobutyl, tert-butyl, 1,1-dimethylpropyl, n-pentyl, sec-pentyl, n-hexyl and n-heptyl;

or is a group selected from the group consisting of phenyl, benzyl, phenethyl, naphthyl, (1,3)-benzodioxolyl, (1,4)-benzodioxanyl, thiophenyl, furanyl, pyrrolyl, pyrazolyl, pyranyl, pyridinyl, imidazolyl, indolyl, isoindolyl, benzo[b]furanyl, benzo[b]thiophenyl, thiazolyl, oxazolyl, isoxazolyl, pyridazinyl, pyrazinyl, pyrimidinyl, indazolyl, quinazolinyl, quinolinyl, isoquinolinyl, benzimidazolinyl, benzoxazolyl, benzisoxazolyl and benzothiazolyl, optionally bonded via a —(CH$_2$)—, —(CH$_2$)—(CH$_2$)— or —(CH$_2$)—(CH$_2$)—(CH$_2$)— group and in each case optionally substituted by 1, 2, 3, 4 or 5 substituents selected independently from the group consisting of F, Cl, Br, I, —CN, —CF$_3$, —SF$_5$, —OH, —O—CH$_3$, —O—C$_2$H$_5$, —NH$_2$, —NO$_2$, —O—CF$_3$, —S—CF$_3$, —SH, —S—CH$_3$, —S—C$_2$H$_5$, methyl, ethyl, n-propyl, isopropyl, n-butyl, sec-butyl, isobutyl, tert-butyl, —C(=O)—OH, —C(=O)—O—CH$_3$, —C(=O)—O—C$_2$H$_5$, —C(=O)—O—C(CH$_3$)$_3$, —O—C(=O)—CH$_3$, —O—C(=O)—C$_2$H$_5$, —O—C(=O)—C(CH$_3$)$_3$, —N(CH$_3$)$_2$, —N(C$_2$H$_5$)$_2$, —NH—CH$_3$, —NH—C$_2$H$_5$, —NH—C(=O)—O—CH$_3$, —NH—C(=O)—O—C$_2$H$_5$, —NH—C(=O)—O—C(CH$_3$)$_3$, —C(=O)—H, —C(=O)—CH$_3$, —C(=O)—C$_2$H$_5$, —C(=O)—C(CH$_3$)$_3$, —C(=O)—NH$_2$, —C(=O)—NH—CH$_3$, —C(=O)—NH—C$_2$H$_5$, —C(=O)—N—(CH$_3$)$_2$, —C(=O)—N—(C$_2$H$_5$)$_2$, —S(=O)$_2$—CH$_3$, —S(=O)$_2$—C$_2$H$_5$, —NH—S(=O)$_2$—CH$_3$, —NH—S(=O)$_2$—C$_2$H$_5$, —S(=O)$_2$—NH—CH$_3$ and —S(=O)$_2$—NH—C$_2$H$_5$;

$R^{27}$ is a hydrogen;

and $R^{28}$ and $R^{29}$ are each independently a group selected from the group consisting of phenyl, naphthyl, thiophenyl, furanyl and pyridinyl, in each case optionally substituted by 1, 2, 3, 4 or 5 substituents selected independently from the group consisting of F, Cl, Br, I, —CN, —CF$_3$, —SF$_5$, —OH, —O—CH$_3$, —O—C$_2$H$_5$, —NH$_2$, —NO$_2$, —O—CF$_3$, —S—CF$_3$, —SH, —S—CH$_3$, —S—C$_2$H$_5$, methyl, ethyl, n-propyl, isopropyl, n-butyl, sec-butyl, isobutyl, tert-butyl, —N(CH$_3$)$_2$, —N(C$_2$H$_5$)$_2$, —NH—CH$_3$ and —NH—C$_2$H$_5$;

in each case, as appropriate, in the form of one of its pure stereoisomers, of its racemates or in the form of a mixture of stereoisomers in any mixing ratio, or in each case in the form of corresponding salts.

13. A compound as claimed in claim 1, characterized in that n is 1;

X is CH$_2$, O, S, S(=O) or S(=O)$_2$;

Y is O, O—C(=O), O—C(=O)—O, O—S(=O)$_2$, O—C(=S)—N(H) or O—C(=O)—N(H);

$R^1$, $R^2$, $R^3$ and $R^4$, are each independently

H, F, Cl, Br, —SF$_5$, —OH, —OR$^{10}$, —SR$^{11}$, —NR$^{12}$R$^{13}$, or a group selected from the group consisting of methyl, —CF$_3$, —CHF$_2$, —CH$_2$F, —CCl$_3$, —CBr$_3$, —CH$_2$—CN, —CH$_2$—NO$_2$, ethyl, —CF$_2$—CF$_3$, —CH$_2$—CF$_3$, n-propyl, isopropyl, n-butyl, sec-butyl, isobutyl, tert-butyl, 1,1-dimethylpropyl and n-pentyl;

$R^5$ is a —C(=O)—$R^{24}$ group;

is a —S(=O)$_2$—$R^{25}$ group;

is a group selected from the group consisting of methyl, ethyl, n-propyl, isopropyl, n-butyl, sec-butyl, isobutyl, tert-butyl, 1,1-dimethylpropyl, n-pentyl, sec-pentyl, n-hexyl and n-heptyl;

is a group selected from the group consisting of cyclopropyl, cyclobutyl, cyclopentyl, cyclohexyl, cycloheptyl, cyclopentenyl, cyclohexenyl and cycloheptenyl;

or is a group selected from the group consisting of phenyl, naphthyl, thiophenyl, furanyl, pyridinyl, indolyl, thiazolyl and oxazolyl, in each case optionally substituted by 1, 2, 3, 4 or 5 substituents selected independently from the group consisting of F, Cl, Br, —SF$_5$, —CF$_3$, —O—CH$_3$, —O—C$_2$H$_5$, —SCH$_3$, —SC$_2$H$_5$, —O—CF$_3$, —S—CF$_3$, methyl, ethyl, n-propyl, isopropyl, n-butyl, sec-butyl, isobutyl and tert-butyl;

$R^6$ is a hydrogen;

is —(CH$_2$)—Z—$R^{26}$;

or is —(CH$_2$)—OR$^{27}$;

$R^{10}$, $R^{11}$, $R^{12}$ and $R^{13}$ are each independently a group selected from the group consisting of methyl, —CF$_3$, —CH$_2$F, —CF$_2$H, ethyl, —C$_2$F$_5$, n-propyl, isopropyl, n-butyl, sec-butyl, isobutyl, tert-butyl, 1,1-dimethylpropyl, n-pentyl, sec-pentyl, n-hexyl and n-heptyl;

Z is O, O—C(=O), O—C(=O)—O, O—S(=O)$_2$, O—C(=S)—N(H) or O—C(=O)—N(H);

$R^{24}$ and $R^{25}$ are each independently a group selected from the group consisting of phenyl, naphthyl, thiophenyl, furanyl and pyridinyl, in each case optionally substituted by 1, 2, 3, 4 or 5 substituents selected independently from the group consisting of F, Cl, Br, I, —CF$_3$, —SF$_5$, —O—CH$_3$, —O—C$_2$H$_5$, —S—CF$_3$, methyl, ethyl, n-propyl, isopropyl, n-butyl, sec-butyl, isobutyl and tert-butyl;

R$^{26}$ is a —C(=O)—R$^{28}$ group;
is a —S(=O)$_2$—R$^{29}$ group;
is a group selected from the group consisting of methyl, ethyl, n-propyl, isopropyl, n-butyl, sec-butyl, isobutyl, tert-butyl, 1,1-dimethylpropyl, n-pentyl, sec-pentyl, n-hexyl and n-heptyl;
is a group selected from the group consisting of cyclopropyl, cyclobutyl, cyclopentyl, cyclohexyl, cycloheptyl, cyclopentenyl, cyclohexenyl and cycloheptenyl;
or is a group selected from the group consisting of phenyl, naphthyl, thiophenyl, furanyl, pyridinyl, indolyl, thiazolyl and oxazolyl, where the radical may in each case optionally be substituted by 1, 2, 3, 4 or 5 substituents selected independently from the group consisting of F, Cl, Br, —SF$_5$, —CF$_3$, —O—CH$_3$, —O—C$_2$H$_5$, —SCH$_3$, —SC$_2$H$_5$, —O—CF$_3$, —S—CF$_3$, methyl, ethyl, n-propyl, isopropyl, n-butyl, sec-butyl, isobutyl and tert-butyl;

R$^{27}$ is a hydrogen;
and
R$^{28}$ and R$^{29}$ are each independently
a group selected from the group consisting of phenyl, naphthyl, thiophenyl, furanyl and pyridinyl, where the radical may in each case optionally be substituted by 1, 2, 3, 4 or 5 substituents selected independently from the group consisting of F, Cl, Br, I, —CF$_3$, —SF$_5$, —O—CH$_3$, —O—C$_2$H$_5$, —S—CF$_3$, methyl, ethyl, n-propyl, isopropyl, n-butyl, sec-butyl, isobutyl and tert-butyl;

in each case, as appropriate, in the form of one of its pure stereoisomers, of its racemates or in the form of a mixture of stereoisomers in any mixing ratio, or in each case in the form of corresponding salts.

14. A compound as claimed in claim 1, selected from the group consisting of
[1] 1 pentylcarbamic acid 5-oxo-2,3,4,5-tetrahydrobenzo[b]thiepin-4-ylmethyl ester
[2] phenylcarbamic acid 4-(phenylcarbamoyloxymethyl)-5-oxo-2,3,4,5-tetrahydrobenzo[b]thiepin-4-ylmethyl ester
[3] phenylcarbamic acid 5-oxo-2,3,4,5-tetrahydrobenzo[b]thiepin-4-ylmethyl ester
[4] (3-trifluoromethylphenyl)carbamic acid 5-oxo-2,3,4,5-tetrahydro-benzo[b]thiepin-4-ylmethyl ester
[5] (4-bromophenyl)carbamic acid 5-oxo-2,3,4,5-tetrahydro-benzo[b]thiepin-4-ylmethyl ester
[6] cyclohexylcarbamic acid 4-hydroxymethyl-5-oxo-2,3,4,5-tetrahydro-benzo[b]thiepin-4-ylmethyl ester
[7] cyclohexylcarbamic acid 5-oxo-2,3,4,5-tetrahydrobenzo[b]thiepin-4-ylmethyl ester
[8] cyclohexylcarbamic acid 6-(cyclohexylcarbamoyloxymethyl)-5-oxo-6,7,8,9-tetrahydro-5H-benzocyclohepten-6-ylmethyl ester
[9] phenylthiocarbamic acid O-(4-hydroxymethyl-5-oxo-2,3,4,5-tetrahydro-benzo[b]thiepin-4-ylmethyl) ester
[10] N-(4-methylphenylsulfonyl)carbamic acid 5-oxo-2,3,4,5-tetrahydro-benzo[b]thiepin-4-ylmethyl ester
[11] naphthalen-1-ylthiocarbamic acid O-(4-hydroxymethyl-5-oxo-2,3,4,5-tetrahydrobenzo[b]thiepin-4-ylmethyl) ester
[12] pentylcarbamic acid 4-hydroxymethyl-5-oxo-2,3,4,5-tetrahydro-benzo[b]oxepin-4-ylmethyl ester
[13] pentylcarbamic acid 4-hydroxymethyl-5-oxo-2,3,4,5-tetrahydro-benzo[b]thiepin-4-ylmethyl ester
[14] pentylcarbamic acid 4-(pentylcarbamoyloxymethyl)-5-oxo-2,3,4,5-tetrahydrobenzo[b]thiepin-4-ylmethyl ester
[15] phenylthiocarbamic acid O-(4-hydroxymethyl-5-oxo-2,3,4,5-tetrahydro-benzo[b]oxepin-4-ylmethyl) ester
[16] 2,4-difluorophenylcarbamic acid 4-(2,4-difluorophenylcarbamoyloxymethyl)-5-oxo-2,3,4,5-tetrahydrobenzo[b]oxepin-4-ylmethyl ester
[17] (3-trifluoromethylphenyl)thiocarbamic acid O-(4-hydroxymethyl-5-oxo-2,3,4,5-tetrahydrobenzo[b]thiepin-4-ylmethyl) ester
[18] (3-trifluoromethylphenyl)thiocarbamic acid O-(4-hydroxymethyl-5-oxo-2,3,4,5-tetrahydrobenzo[b]oxepin-4-ylmethyl) ester
[19] benzoylcarbamic acid 4-benzoylcarbamoyloxymethyl-5-oxo-2,3,4,5-tetrahydrobenzo[b]oxepin-4-ylmethyl ester
[20] (2,4-difluorophenyl)carbamic acid 4-hydroxymethyl-5-oxo-2,3,4,5-tetrahydrobenzo[b]thiepin-4-ylmethyl ester
[21] (2,4-difluorophenyl)thiocarbamic acid O-(4-hydroxymethyl-5-oxo-2,3,4,5-tetrahydrobenzo[b]thiepin-4-ylmethyl) ester
[22] (3-trifluoromethylphenyl)thiocarbamic acid O-(6-hydroxymethyl-5-oxo-6,7,8,9-tetrahydro-5H-benzocyclohepten-6-ylmethyl) ester
[23] (2,4-difluorophenyl)thiocarbamic acid O-(4-hydroxymethyl-5-oxo-2,3,4,5-tetrahydrobenzo[b]oxepin-4-ylmethyl) ester
[24] (2,4-difluorophenyl)thiocarbamic acid O-(6-hydroxymethyl-5-oxo-6,7,8,9-tetrahydro-5H-benzocyclohepten-6-ylmethyl) ester
[25] (3-trifluoromethylphenyl)carbamic acid 4-(3-trifluoromethylphenyl)-carbamoyloxymethyl-5-oxo-2,3,4,5-tetrahydrobenzo[b]oxepin-4-ylmethyl ester
[26] butylcarbamic acid 4-hydroxymethyl-5-oxo-2,3,4,5-tetrahydro-benzo[b]thiepin-4-ylmethyl ester
[27] butylcarbamic acid 4-(butylcarbamoyloxymethyl)-5-oxo-2,3,4,5-tetrahydrobenzo[b]thiepin-4-ylmethyl ester, and
[28] (4-trifluoromethoxyphenyl)carbamic acid 4-hydroxymethyl-5-oxo-2,3,4,5-tetrahydrobenzo[b]thiepin-4-ylmethyl ester;

in each case, as appropriate, in the form of one of its pure stereoisomers, of its racemates or in the form of a mixture of stereoisomers in any mixing ratio, or in each case in the form of corresponding salts.

15. A process for preparing a compound of formula I as claimed in claim 1, characterized in that at least one compound of the general formula II

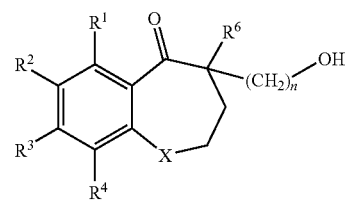

in which X, n and R$^1$ to R$^4$ are each as defined in claim 1 and R$^6$ is a hydrogen, —(CH$_2$)$_q$—NH$_2$ or —(CH$_2$)$_q$—OR$^{27}$, where q and R$^{27}$ are each as defined in claim 1, in a reaction medium, optionally in the presence of at least one base, is reacted with at least one compound of the general formula $R^5$—N=C=O and optionally at least one compound of the general formula $R^{26}$—N=C=O, where $R^5$ and $R^{26}$ may be defined identically according to claim 1, to give at least one compound of the general formula Ia

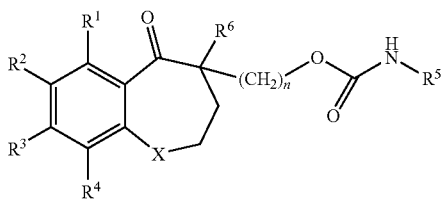

Ia in which X, n and $R^1$ to $R^5$ are each as defined in claim 1 and $R^6$ is a hydrogen, is —$(CH_2)_p$—O—C(=O)—N(H)—$R^{26}$, is —$(CH_2)_p$—N(H)—C(=O)—N(H)—$R^{26}$ or is —$(CH_2)_q$—$OR^{27}$; where p, q, $R^{26}$ and $R^{27}$ are each as defined in claim 1; and the latter is optionally purified and/or isolated;

or at least one compound of the general formula II in which X, n and $R^1$ to $R^4$ are each as defined in claim 1 and $R^6$ is a hydrogen or —$(CH_2)_q$—$OR^{27}$, where q and $R^{27}$ are each as defined in claim 1; in a reaction medium, optionally in the presence of at least one base, is reacted with at least one compound of the general formula $R^5$—S(=O)$_2$-LG and optionally at least one compound of the general formula $R^{26}$—S(=O)$_2$-LG, where $R^5$ and $R^{26}$ may be defined identically according to claim 1 and LG is a leaving group, to give at least one compound of the general formula Ib,

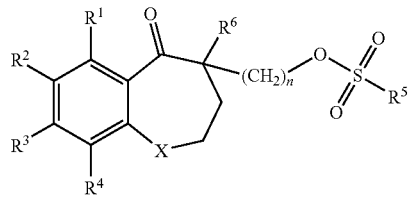

Ib in which X, n and $R^1$ to $R^5$ are each as defined in claim 1 and $R^6$ is a hydrogen, is —$(CH_2)_p$—O—S(=O)$_2$—$R^{26}$ or is —$(CH_2)_q$—$OR^{27}$; where p, q, $R^{26}$ and $R^{27}$ may each be as defined in claim 1; and the latter is optionally purified and/or isolated;

or at least one compound of the general formula II in which X, n and $R^1$ to $R^4$ are each as defined in claim 1 and $R^6$ is a hydrogen or —$(CH_2)_q$—$OR^{27}$ where q and $R^{27}$ are each as defined in claim 1; in a reaction medium, optionally in the presence of a base, is reacted with at least one compound of the general formula $R^5$—C(=O)-LG and optionally at least one compound of the general formula $R^{26}$—C(=O)-LG, where $R^5$ and $R^{26}$ are optionally defined identically according to claim 1 and LG is a leaving group, to give at least one compound of the general formula Ic

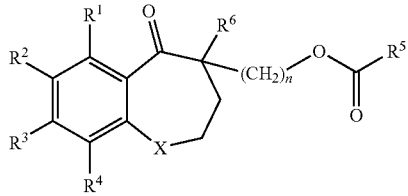

Ic in which X, n and $R^1$ to $R^5$ are each as defined in claim 1 and $R^6$ is a hydrogen, is —$(CH_2)_p$—O—C(=O)—$R^{26}$ or is —$(CH_2)_q$—$OR^{27}$; where p, q, $R^{26}$ and $R^{27}$ are each as defined in claim 1; and the latter is optionally purified and/or isolated;

or at least one compound of the general formula II in which X, n and $R^1$ to $R^4$ are each as defined in claim 1 and $R^6$ is a hydrogen or —$(CH_2)_q$—$OR^{27}$ where q and $R^{27}$ are each as defined in claim 1; in a reaction medium, optionally in the presence of at least one base, is reacted with at least one compound of the general formula $R^5$—O—C(=O)-LG and optionally at least one compound of the general formula $R^{26}$—O—C(=O)-LG, where $R^5$ and $R^{26}$ may be defined identically according to claim 1 and LG is a leaving group, to give at least one compound of the general formula Id

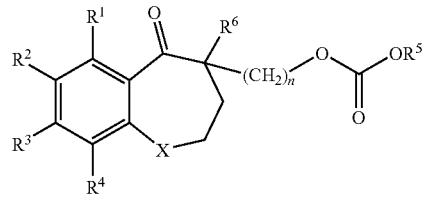

Id in which X, n and $R^1$ to $R^5$ are each as defined in claim 1 and $R^6$ is a hydrogen, is —$(CH_2)_p$—O—C(=O)—O—$R^{26}$ or is —$(CH_2)_q$—$OR^{27}$; where p, q, $R^{26}$ and $R^{27}$ are each as defined in claim 1; and the latter is optionally purified and/or isolated;

or at least one compound of the general formula II in which X, n and $R^1$ to $R^4$ are each as defined in claim 1 and $R^6$ is a hydrogen, —$(CH_2)_q$—$NH_2$ or —$(CH_2)_q$—$OR^{27}$, where q and $R^{27}$ are each as defined in claim 1; in a reaction medium, in the presence of at least one base, is reacted with at least one compound of the general formula $R^5$-LG and optionally at least one compound of the general formula $R^{26}$-LG, where $R^5$ and $R^{26}$ may be defined identically according to claim 1 and LG is a leaving group, to give at least one compound of the general formula Ie,

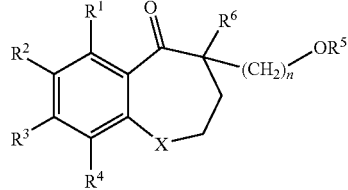

Ie in which X, n and $R^1$ to $R^5$ are each as defined in claim 1 and $R^6$ is a hydrogen, is —$(CH_2)_p$—$OR^{26}$, is —$(CH_2)_p$—$NHR^{26}$ or is —$(CH_2)_q$—$OR^{27}$; where p, q, $R^{26}$ and $R^{27}$ are each as defined in claim 1; and the latter is optionally purified and/or isolated;

or at least one compound of the general formula II in which X, n and $R^1$ to $R^4$ are each as defined in claim 1 and $R^6$ is a hydrogen, —$(CH_2)_q$—$NH_2$ or —$(CH_2)_q$—$OR^{27}$, where q and $R^{27}$ are each as defined in claim 1, in a reaction medium, optionally in the presence of at least one base, is reacted with at least one compound of the general formula $R^5$—N=C=S and optionally at least one compound of the general formula $R^{26}$—N=C=S, where $R^5$ and $R^{26}$ may be defined identically according to claim 1, to give at least one compound of the general formula If

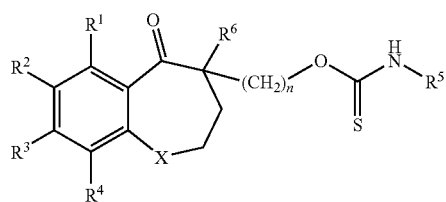

in which X, n and $R^1$ to $R^5$ are each as defined in claim 1, and $R^6$ is a hydrogen, is —$(CH_2)_p$—O—C(=S)—N(H)—$R^{26}$, is —$(CH_2)_p$—N(H)—C(=S)—N(H)—$R^{26}$ or is —$(CH_2)_q$—$OR^{27}$; where p, q, $R^{26}$ and $R^{27}$ are each as defined in claim 1; and the latter is optionally purified and/or isolated;

and optionally at least one compound of the general formula Ia, Ib, Ic, Id, Ie or If in which X, n and $R^1$ to $R^5$ are each as defined in claim 1 and Y is O, O—C(=O), O—C(=O)—O, O—S(=O)$_2$, o—C(=S)—N(H) or O—C(=O)—N(H) and $R^6$ is —$(CH_2)_q$—$OR^{27}$ where $R^{27}$ is a hydrogen; in a reaction medium, optionally in the presence of at least one base, is reacted with at least one compound of the general formula $R^{26}$—N=C=O to give at least one compound of the general formula Ia, Ib, Ic, Id or Ie in which X, n and $R^1$ to $R^5$ are each as defined in claim 1, and Y is O, O—C(=O), O—C(=O)—O, O—S(=O)$_2$, O—C(=S)—N(H) or O—C(=O)—N(H) and $R^6$ is —$(CH_2)_p$—O—C(=O)—N(H)—$R^{26}$; and the latter is optionally purified and/or isolated;

or optionally at least one compound of the general formula Ia, Ib, Ic, Id, Ie or If in which X, n and $R^1$ to $R^5$ are each as defined in claim 1, and Y is O, O—C(=O), O—C(=O)—O, O—S(=O)$_2$, O—C(=S)—N(H) or O—C(=O)—N(H) and $R^6$ is —$(CH_2)_q$—$OR^{27}$ where $R^{27}$ is a hydrogen; in a reaction medium, optionally in the presence of at least one base, is reacted with at least one compound of the general formula $R^{26}$—S(=O)$_2$-LG to give at least one compound of the general formula Ia, Ib, ic, Id or Ie in which X, n and $R^1$ to $R^5$ are each as defined in claim 1 and Y is O, O—C(=O), O—C(=O)—O, O—S(=O)$_2$, O—C(=S)—N(H) or O—C(=O)—N(H) and $R^6$ is —$(CH_2)_p$—O—S(=O)$_2$—$R^{26}$; and the latter is optionally purified and/or isolated;

or or optionally at least one compound of the general formula Ia, Ib, Ic, Id, Ie or If in which X, n and $R^1$ to $R^5$ are each as defined in claim 1, and Y is O, O—C(=O), O—C(=O)—O, O—S(=O)$_2$, O—C(=S)—N(H) or O—C(=O)—N(H) and $R^6$ is —$(CH_2)_q$—$OR^{27}$ where $R^{27}$ is a hydrogen; in a reaction medium, optionally in the presence of at least one base, is reacted with at least one compound of the general formula $R^{26}$—C(=O)-LG to give at least one compound of the general formula Ia, Ib, Ic, Id or Ie in which X, n and $R^1$ to $R^5$ are each as defined in claim 1, and Y is O, O—C(=O), O—C(=O)—O, O—S(=O)$_2$, O—C(=S)—N(H) or O—C(=O)—N(H) and $R^6$ is —$(CH_2)_p$—O—C(=O)—$R^{26}$; and the latter is optionally purified and/or isolated;

or optionally at least one compound of the general formula Ia, Ib, Ic, Id, Ie or If in which X, n and $R^1$ to $R^5$ are each as defined in claim 1, and Y is O, O—C(=O), O—C(=O)—O, O—S(=O)$_2$, O—C(=S)—N(H) or O—C(=O)—N(H) and $R^6$ is —$(CH_2)_q$—$OR^{27}$ where $R^{27}$ is a hydrogen; in a reaction medium, optionally in the presence of at least one base, is reacted with at least one compound of the general formula $R^{26}$—O—C(=O)-LG to give at least one compound of the general formula Ia, Ib, Ic, Id or Ie in which X, n and $R^1$ to $R^5$ are each as defined in claim 1, and Y is O, O—C(=O), O—C(=O)—O, O—S(=O)$_2$, O—C(=S)—N(H) or O—C(=O)—N(H) and $R^6$ is —$(CH_2)_p$—O—C(=O)—O—$R^{26}$; and the latter is optionally purified and/or isolated;

or optionally at least one compound of the general formula Ia, Ib, Ic, Id, Ie or If in which X, n and $R^1$ to $R^5$ are each as defined in claim 1, and Y is O, O—C(=O), O—C(=O)—O, O—S(=O)$_2$, o—C(=S)—N(H) or O—C(=O)—N(H) and $R^6$ is —$(CH_2)_q$—$OR^{27}$ where $R^{27}$ is a hydrogen; in a reaction medium, in the presence of at least one base, is reacted with at least one compound of the general formula $R^{26}$-LG to give at least one compound of the general formula Ia, Ib, Ic, Id or Ie in which X, n and $R^1$ to $R^5$ are each as defined in claim 1, and Y is O, O—C(=O), O—C(=O)—O, O—S(=O)$_2$, O—C(=S)—N(H) or O—C(=O)—N(H) and $R^6$ is —$(CH_2)_p$—O—$R^{26}$; and the latter is optionally purified and/or isolated;

or optionally at least one compound of the general formula Ia, Ib, Ic, Id, Ie or If in which X, n and $R^1$ to $R^5$ are each as defined in claim 1, and Y is O, O—C(=O), O—C(=O)—O, O—S(=O)$_2$, O—C(=S)—N(H) or O—C(=O)—N(H) and $R^6$ is —$(CH_2)_q$—$OR^{27}$ where $R^{27}$ is a hydrogen; in a reaction medium, optionally in the presence of at least one base, is reacted with at least one compound of the general formula $R^{26}$—N=C=S to give at least one compound of the general formula Ia, Ib, Ic, Id or Ie; in which X, n and $R^1$ to $R^5$ are each as defined in claim 1, and Y is O, O—C(=O), O—C(=O)—O, O—S(=O)$_2$, O—C(=S)—N(H) or O—C(=O)—N(H) and $R^6$ is —$(CH_2)_p$—O—C(=S)—N(H)—$R^{26}$; and the latter is optionally purified and/or isolated;

or optionally at least one compound of the general formula Ia, Ib, Ic, Id, Ie or If in which X, n and $R^1$ to $R^5$ are each as defined in claim 1, and Y is O, O—C(=O), O—C(=O)—O, O—S(=O)$_2$, O—C(=S)—N(H) or O—C(=O)—N(H) and $R^6$ is —$(CH_2)_p$—$NH_2$; in a reaction medium, optionally in the presence of at least one base, is reacted with at least one compound of the general formula $R^{26}$—N=C=S to give at least one compound of the general formula Ia, Ib, Ic, Id or Ie in which X, n and $R^1$ to $R^5$ are each as defined in claim 1, and Y is O, O—C(=O), O—C(=O)—O, O—S(=O)$_2$, O—C (=S)—N(H) or O—C(=O)—N(H) and R⁶ is —(CH₂)ₚ—N—C(=S)—N(H)—R²⁶; and the latter is optionally purified and/or isolated;

or optionally at least one compound of the general formula Ia, Ib, Ic, Id, Ie or If in which X, n and R¹ to R⁵ are each as defined in claim 1, and Y is O, O—C(=O), O—C(=O)-0, O—S(=O)₂, O—C(=S)—N(H) or O—C(=O)—N(H) and R⁶ is —(CH₂)ₚ—NH₂; in a reaction medium, optionally in the presence of at least one base, is reacted with at least one compound of the general formula R²⁶—N=C=O to give at least one compound of the general formula Ia, Ib, Ic, Id or Ie in which X, n and R¹ to R⁵ are each as defined in claim 1, and Y is O, O—C(=O), O—C(=O)—O, O—S(=O)₂, O—C(=S)—N(H) or O—C(=O)—N(H) and R⁶ is —(CH₂)ₚ—N—C(=O)—N(H)—R²⁶; and the latter is optionally purified and/or isolated;

or optionally at least one compound of the general formula Ia, Ib, Ic, Id, Ie or If in which X, n and R¹ to R⁵ are each as defined in claim 1 and Y is O, O—C(=O), O—C(=O)—O, O—S(=O)₂, O—C(=S)—N(H) or O—C(=O)—N(H) and R⁶ is —(CH₂)ₚ—NH₂; in a reaction medium, in the presence of at least one base, is reacted with at least one compound of the general formula R²⁶-LG to give at least one compound of the general formula Ia, Ib, ic, Id or Ie; in which X, n and R¹ to R⁵ are each as defined in claim 1, and Y is O, O—C(=O), O—C(=O)—O, O—S(=O)₂, O—C(=S)—N(H) or O—C(=O)—N(H) and R⁶ is —(CH₂)ₚ—N(H)—R²⁶; and the latter is optionally purified and/or isolated;

and optionally at least one compound of the general formula Ia, Ib, Ic, Id, Ie or If in which n, R¹ to R⁶ and Y are each as defined above and X is S in a reaction medium, in the presence of sodium metaperiodate, is converted to at least one compound of the general formula Ia, Ib, Ic, Id or Ie in which n, R¹ to R⁶ and Y are each as defined in claim 1, and X is S(=O); and the latter is optionally purified and/or isolated;

and optionally at least one compound of the general formula Ia, Ib, Ic, Id, Ie or If, in which n, R¹ to R⁶ and Y are each as defined in claim 1, and X is S in a reaction medium, in the presence of hydrogen peroxide and acetic acid, is converted to at least one compound of the general formula Ia, Ib, Ic, Id or Ie in which n, R¹ to R⁶ and Y are each as defined in claim 1, and X is S(=O)₂; and the latter is optionally purified and/or isolated.

16. A process for preparing a compound of formula I as claimed in claim 1, characterized in that at least one compound of the general formula III,

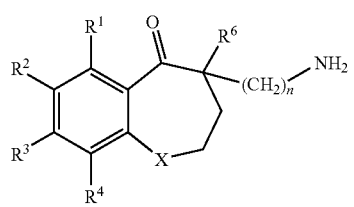

III in which X, n and R¹ to R⁴ are each as defined in claim 1, and R⁶ is a hydrogen or is —(CH₂)ₚ—NH₂ where q is as defined in claim 1, in a reaction medium, optionally in the presence of at least one base, is reacted with at least one compound of the general formula R⁵—N=C=O and optionally at least one compound of the general formula R²⁶—N=C=O, where R⁵ and R²⁶ may be defined identically according to claim 1 to give at least one compound of the general formula Ig

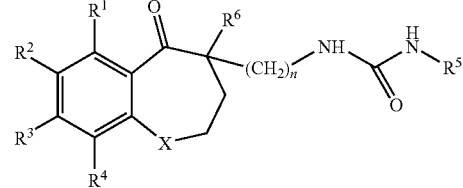

Ig in which X, n and R¹ to R⁵ are each as defined in claim 1, and R⁶ is a hydrogen or is —(CH₂)ₚ—N(H)—C(=O)—N(H)—R²⁶ where p and R²⁶ are each as defined in claim 1; and the latter is optionally purified and/or isolated;

or at least one compound of the general formula III in a reaction medium, optionally in the presence of at least one base, is reacted with at least one compound of the general formula R⁵—N=C=S and optionally at least one compound of the general formula R²⁶—N=C=S, where R⁵ and R²⁶ may be defined identically according to claim 1, to give at least one compound of the general formula Ih

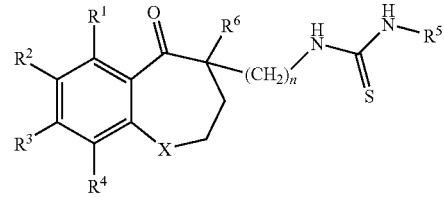

Ih in which X, n and R¹ to R⁵ are each as defined in claim 1, and R⁶ is a hydrogen or is —(CH₂)ₚ—N(H)—C(=S)—N(H)—R²⁶ where p and R²⁶ are each as defined in claim 1; and the latter is optionally purified and/or isolated;

or at least one compound of the general formula III in a reaction medium, in the presence of at least one base, is reacted with a least one compound of the general formula R⁵-LG and optionally at least one compound of the general formula R²⁶-LG, where R⁵ and R²⁶ may be defined identically according to claim 1, and LG is a leaving group, to give at least one compound of the general formula Ik

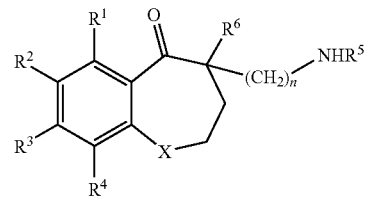

Ik in which X, n and R¹ to R⁵ are each as defined in claim 1, and R⁶ is a hydrogen or is —(CH₂)ₚ—R²⁶ where p and R²⁶ are each as defined in claim 1;

and the latter is optionally purified and/or isolated;

or optionally at least one compound of the general formula Ig, Ih or Ik in which X, n and R¹ to R⁵ are each as defined in claim 1, and Y is N(H)—C(=O)—N(H) or N(H)—C(=S)—N(H) and R⁶ is —(CH₂)ₚ—NH₂; in a reaction medium, optionally in the presence of at least one base, is reacted with at least one compound of the general formula $R^{26}$—N=C=O to give at least one compound of the general formula Ig, Ih or Ik in which X, n and $R^1$ to $R^5$ are each as defined in claim 1, and Y is N(H)—C(=O)—N(H) or N(H)—C(=S)—N(H) and $R^6$ is —$(CH_2)_p$—N(H)—C(=O)—N(H)—$R^{26}$; and the latter is optionally purified and/or isolated;

or optionally at least one compound of the general formula Ig, Ih or Ik in which X, n and $R^1$ to $R^5$ are each as defined in claim 1, and Y is N(H)—C(=O)—N(H) or N(H)—C(=S)—N(H) and $R^6$ is —$(CH_2)_p$—$NH_2$; in a reaction medium, optionally in the presence of at least one base, is reacted with at least one compound of the general formula $R^{26}$—N=C=S to give at least one compound of the general formula Ig, Ih or Ik in which X, n and $R^3$ to $R^5$ are each as defined in claim 1, and Y is N(H)—C(=O)—N(H) or N(H)—C(=S)—N(H) and $R^6$ is —$(CH_2)_p$—N(H)—C(=S)—N(H)—$R^{26}$; and the latter is optionally purified and/or isolated;

or optionally at least one compound of the general formula Ig, Ih or Ik in which X, n and $R^1$ to $R^5$ are each as defined in claim 1, and Y is N(H)—C(=O)—N(H) or N(H)—C(=S)—N(H) and $R^6$ is —$(CH_2)_p$—$NH_2$; in a reaction medium, in the presence of at least one base, is reacted with at least one compound of the general formula $R^{26}$-LG to give at least one compound of the general formula Ig, Ih or Ik in which X, n and $R^1$ to $R^5$ are each as defined in claim 1, and Y is N(H)—C(=O)—N(H) or N(H)—C(=S)—N(H) and $R^6$ is —$(CH_2)_p$—N(H)—$R^{26}$; and the latter is optionally purified and/or isolated;

and optionally at least one compound of the general formula Ig, Ih or Ik in which n, $R^1$ to $R^6$ and Y are each as defined in claim 1, and X is S in a reaction medium in the presence of sodium metaperiodate is converted to at least one compound of the general formula Ia, Ib, Ic, Id or Ie in which n, $R^1$ to $R^6$ and Y are each as defined in claim 1, and X is S(=O); and the latter is optionally purified and/or isolated;

and optionally at least one compound of the general formula Ig, Ih or Ik in which n, $R^1$ to $R^6$ and Y are each as defined in claim 1, and X is S in a reaction medium in the presence of hydrogen peroxide and acetic acid is converted to at least one compound of the general formula Ia, Ib, Ic, Id or Ie in which n, $R^1$ to $R^6$ and Y are each as defined in claim 1, and X is $S(=O)_2$; and the latter is optionally purified and/or isolated.

17. A pharmaceutical composition comprising at least one compound as claimed in claim 1 and one or more physiologically compatible excipients.

18. A method of treating or inhibiting pain in a subject in need thereof, said method comprising administering to said subject a pharmacologically effective amount of a compound as claimed in claim 1.

19. A method according to claim 18, wherein said pain is pain selected from the group consisting of acute pain, chronic pain, neuropathic pain and visceral pain.

* * * * *